(12) United States Patent
Sharp et al.

(10) Patent No.: US 8,657,824 B2
(45) Date of Patent: Feb. 25, 2014

(54) UNIVERSAL DOUBLE OFFSET SURGICAL INSTRUMENT

(75) Inventors: Jeffrey A. Sharp, Memphis, TN (US); Luke A. Gibson, Southaven, MS (US); David C. Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 502 days.

(21) Appl. No.: 12/623,030

(22) Filed: Nov. 20, 2009

(65) Prior Publication Data
US 2010/0121331 A1 May 13, 2010

Related U.S. Application Data

(63) Continuation-in-part of application No. 12/412,527, filed on Apr. 27, 2009, now Pat. No. 8,096,993, which is a continuation of application No. 10/991,641, filed on Nov. 18, 2004, now Pat. No. 7,591,821.

(60) Provisional application No. 60/520,970, filed on Nov. 18, 2003.

(51) Int. Cl.
*A61B 17/00* (2006.01)
(52) U.S. Cl.
USPC ................................. 606/84; 606/80; 606/99
(58) Field of Classification Search
USPC .......................................... 606/79, 84–85, 95
See application file for complete search history.

(56) References Cited

U.S. PATENT DOCUMENTS

| | | | |
|---|---|---|---|
| 3,029,811 A | 4/1962 | Yost | |
| 3,815,599 A | 6/1974 | Deyerle | |
| 3,955,568 A | 5/1976 | Neufeld | |
| 4,306,500 A | 12/1981 | Castanien et al. | |
| 4,306,550 A | 12/1981 | Forte | |
| D272,764 S | 2/1984 | Dohogne | |
| 4,457,307 A | 7/1984 | Stillwell | |
| 4,565,192 A | 1/1986 | Shapiro | |
| 4,574,794 A | 3/1986 | Cooke et al. | |
| 4,583,270 A | 4/1986 | Kenna | |

(Continued)

FOREIGN PATENT DOCUMENTS

| | | |
|---|---|---|
| DE | 2732325 | 1/1979 |
| DE | 19850980 | 5/2000 |

(Continued)

OTHER PUBLICATIONS

International Search Report and Written Opinion dated May 23, 2011 in related Application No. PCT/US2010/057326.

(Continued)

*Primary Examiner* — Andrew Yang
(74) *Attorney, Agent, or Firm* — Fish & Richardson P.C.

(57) ABSTRACT

Instruments for use in anterior approach total hip arthroplasty. Instruments according to certain embodiments of the invention connect to a shaping member such as a broach, reamer or osteotome that is used to prepare the intramedullary canal of a desired femur or other bone for total hip arthroplasty. Such an instrument according to such embodiments can be configurable to allow operation on either the left or right leg, and in doing so to provide lateral offset and anterior offset of the instrument handle relative to the shaping member so that the patient's gut, musculature or other bodily portions may be avoided while still providing desired leverage and control over the shaping member to prepare the intramedullary canal.

34 Claims, 66 Drawing Sheets

(56) References Cited

U.S. PATENT DOCUMENTS

| | | | |
|---|---|---|---|
| 4,587,964 A | 5/1986 | Walker et al. |
| 4,703,751 A | 11/1987 | Pohl |
| 4,765,328 A | 8/1988 | Keller et al. |
| 4,921,493 A | 5/1990 | Webb, Jr. et al. |
| 4,938,762 A | 7/1990 | Wehrli |
| 4,952,213 A | 8/1990 | Bowman et al. |
| 4,990,149 A | 2/1991 | Fallin |
| 5,049,149 A | 9/1991 | Schmidt |
| 5,089,003 A | 2/1992 | Fallin et al. |
| 5,089,004 A | 2/1992 | Averill et al. |
| 5,129,909 A | 7/1992 | Sutherland |
| 5,190,549 A | 3/1993 | Miller et al. |
| 5,190,550 A | 3/1993 | Miller et al. |
| 5,261,915 A | 11/1993 | Durlacher et al. |
| 5,324,293 A | 6/1994 | Rehmann |
| 5,352,230 A | 10/1994 | Hood |
| 5,364,401 A | 11/1994 | Ferrante et al. |
| 5,443,471 A * | 8/1995 | Swajger | 606/99 |
| 5,445,642 A | 8/1995 | McNulty et al. |
| 5,486,178 A | 1/1996 | Hodge |
| 5,569,260 A | 10/1996 | Petersen |
| 5,581,892 A | 12/1996 | Dean |
| 5,607,431 A | 3/1997 | Dudasik et al. |
| 5,676,668 A | 10/1997 | McCue et al. |
| 5,681,315 A | 10/1997 | Szabo |
| 5,683,395 A | 11/1997 | Mikhail |
| 5,683,397 A | 11/1997 | Vendrelv et al. |
| 5,688,279 A | 11/1997 | McNulty et al. |
| 5,693,056 A | 12/1997 | Carls et al. |
| 5,704,941 A | 1/1998 | Jacober et al. |
| 5,709,689 A | 1/1998 | Ferrante et al. |
| 5,810,827 A | 9/1998 | Haines et al. |
| 5,810,830 A | 9/1998 | Noble et al. |
| 5,897,559 A | 4/1999 | Masini |
| 5,919,195 A | 7/1999 | Wilson et al. |
| 5,935,128 A | 8/1999 | Carter et al. |
| 5,938,665 A | 8/1999 | Martin |
| 5,993,455 A | 11/1999 | Noble |
| D433,506 S | 11/2000 | Asfora |
| 6,187,006 B1 | 2/2001 | Keller |
| 6,224,605 B1 | 5/2001 | Anderson et al. |
| 6,258,095 B1 | 7/2001 | Lombardo et al. |
| 6,273,915 B1 | 8/2001 | Grimes |
| D454,952 S | 3/2002 | Ku et al. |
| D455,212 S | 4/2002 | Albrektsson et al. |
| 6,409,768 B1 | 6/2002 | Tepic et al. |
| 6,554,837 B1 | 4/2003 | Hauri et al. |
| 6,558,391 B2 | 5/2003 | Axelson, Jr. et al. |
| 6,595,997 B2 | 7/2003 | Axelson, Jr. et al. |
| 6,626,913 B1 | 9/2003 | McKinnon et al. |
| 6,676,706 B1 | 1/2004 | Mears et al. |
| 6,685,711 B2 | 2/2004 | Axelson, Jr. et al. |
| 6,692,503 B2 | 2/2004 | Foley et al. |
| 6,695,850 B2 | 2/2004 | Diaz |
| 7,105,028 B2 | 9/2006 | Murphy |
| 7,396,357 B2 | 7/2008 | Tornier et al. |
| D598,096 S | 8/2009 | Petersen |
| D599,479 S | 9/2009 | Petersen |
| D600,346 S | 9/2009 | Petersen |
| 7,591,821 B2 | 9/2009 | Kelman |
| D648,850 S | 11/2011 | Kelman |
| 8,096,993 B2 | 1/2012 | Kelman |
| 2002/0099446 A1 | 7/2002 | MacArthur |
| 2002/0198531 A1 | 12/2002 | Millard et al. |
| 2003/0050645 A1 | 3/2003 | Parker et al. |
| 2003/0069591 A1 | 4/2003 | Carson et al. |
| 2003/0187449 A1 | 10/2003 | McCleary et al. |
| 2003/0220698 A1 | 11/2003 | Mears |
| 2004/0010261 A1 | 1/2004 | Hoag |
| 2004/0127887 A1 | 7/2004 | Zinkel |
| 2004/0153062 A1 | 8/2004 | McGinley et al. |
| 2004/0153191 A1 | 8/2004 | Grimm et al. |
| 2005/0048853 A1 | 3/2005 | Kelman et al. |
| 2005/0107801 A1 | 5/2005 | Davies et al. |
| 2005/0171548 A1 | 8/2005 | Kelman |
| 2005/0181548 A1 | 8/2005 | Yanagisawa et al. |
| 2005/0216022 A1 | 9/2005 | Lechot et al. |
| 2005/0234462 A1 | 10/2005 | Hershberger |
| 2005/0234463 A1 | 10/2005 | Hershberger et al. |
| 2007/0093897 A1 | 4/2007 | Gerbec et al. |
| 2007/0233134 A1 | 10/2007 | Bastian et al. |
| 2007/0293871 A1 | 12/2007 | Ackermann |
| 2007/0299451 A1 | 12/2007 | Tulkis |
| 2008/0033444 A1 | 2/2008 | Bastian et al. |
| 2008/0255565 A1 | 10/2008 | Fletcher |
| 2009/0275948 A1 | 11/2009 | Kelman |
| 2011/0247633 A1 | 10/2011 | Kelman |
| 2011/0295259 A1 | 12/2011 | Kelman |

FOREIGN PATENT DOCUMENTS

| | | |
|---|---|---|
| DE | 202008017200 | 3/2009 |
| EP | 380451 A2 | 8/1990 |
| EP | 380451 A3 | 8/1990 |
| EP | 380450 A3 | 9/1990 |
| EP | 415837 A2 | 3/1991 |
| EP | 415837 A3 | 3/1991 |
| EP | 0359097 | 8/1992 |
| EP | 0 619 097 A1 | 10/1994 |
| EP | 0 645 127 A1 | 3/1995 |
| EP | 1566147 | 8/2005 |
| FR | 2742334 B1 | 5/1998 |
| FR | 2796261 A | 1/2001 |
| FR | 2854786 A | 11/2004 |
| JP | 4044759 | 2/1992 |
| WO | WO0051530 A1 | 9/2000 |
| WO | WO 03/026517 | 4/2003 |
| WO | WO 03/065906 A2 | 8/2003 |
| WO | WO 03/092513 A1 | 11/2003 |
| WO | WO 2004/024007 A1 | 3/2004 |

OTHER PUBLICATIONS

Office Action dated Apr. 28, 2011 in related U.S. Appl. No. 12/412,527.

Response dated Jun. 29, 2011 in related U.S. Appl. No. 12/412,527.

Multi/Reference 4/in/1 Femoral Knee Instrumentation http://www/zimmer.com/ctl?op=global&action=1&id=1650&template=MP Oct. 13, 2004, two pages.

HSS/HSS/Newsroom: New Knee Replacement Reduce s Recovery Time http://www/hss/edu/Newsroom/New/Knee/Replacement/Reduces/Recover/Time, Mar. 5, 2003, two pages.

Mobile Bearing Knee, Genesis II and Profix Acufex EndoButton CL Brochure, three pages, undated.

Posterior Reference NexGen System Complete Knee Solution Multi/Reference™ 4/in/1 Femoral Instrumentation, Posterior Reference Surgical Technique for NexGen Cruciate Retaining & Legacy® Posterior Stabilized Kneess Zimmer Brochure pp. 1/16 (1996).

Xcelerate™ 4/in/1 Ceramic Cutting Blocks Extemely accurate cutting with the potention for reduced intraoperative wear debris Stryker Howmedica Osteonics Brochure Two pages, undated.

BioRCI/HA Bioabsorbable Screws with Hydroxylapatite, The Innovative Choice for Exceptional Strength and Selection Smith & Nephew Brochure pp. 3/10, undated.

Matrix Opti/Fix Plus, Surgical Technique developed in conjunction with John M. Cuckler, M.D., University of Alabama, Birmingham, Alabama Smith & Nephew Brochure, pp. 1/36, Dec. 1996.

Miller, Steve "Echelon Instrumentation Options," OrthoUpdate, Smith+Nephew, 2 pages, undated.

Smith & Nephew Brochure entitled 'Surgical Technique, Innovations in Minimally Invasive Joint Surgery, Minimally Invasive Hip Replacement Through the Posterior Approach,' 20 pages, Oct. 2003.

Paralign Hip Instrument MIS Systems, Orthogroup, 4 pages, undated.

Deirmengian, et al., "A Technique for the Minimally Invasive, Watson-Jones Approach to Total Hip Arthroplasty," Operative Techniques in Orthopaedics, 2006, pp. 126-134.

(56) References Cited

OTHER PUBLICATIONS

Nogler, et al., "A Double Offset Broach Handle for Preparation of the Femoral Cavity in Minimally Invasive Direct Anterior Total Hip Arthroplasty," The Journal of Arthroplasty, vol. 21, No. 8, 2006, pp. 1206-1208.

International Preliminary Report on Patentability for International Application No. PCT/US2010/057326, mailed May 22, 2012.
Notice of Allowance for U.S. Appl. No. 29/395,763, mailed Oct. 15, 2012.
Office Action for U.S. Appl. No. 13/019,635, mailed Oct. 16, 2012.
Office Action for U.S. Appl. No. 13/019,635, mailed Jun. 6, 2013.

* cited by examiner

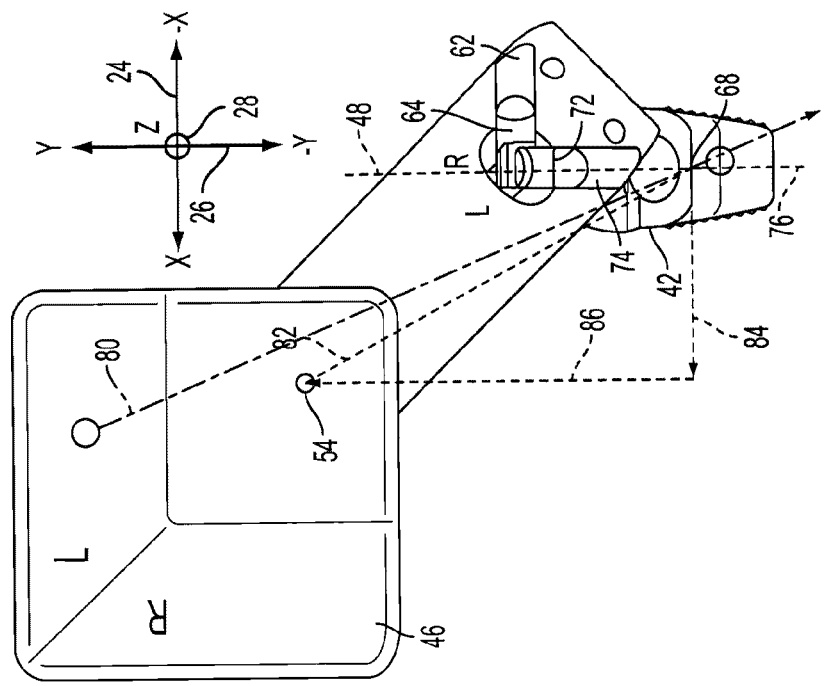
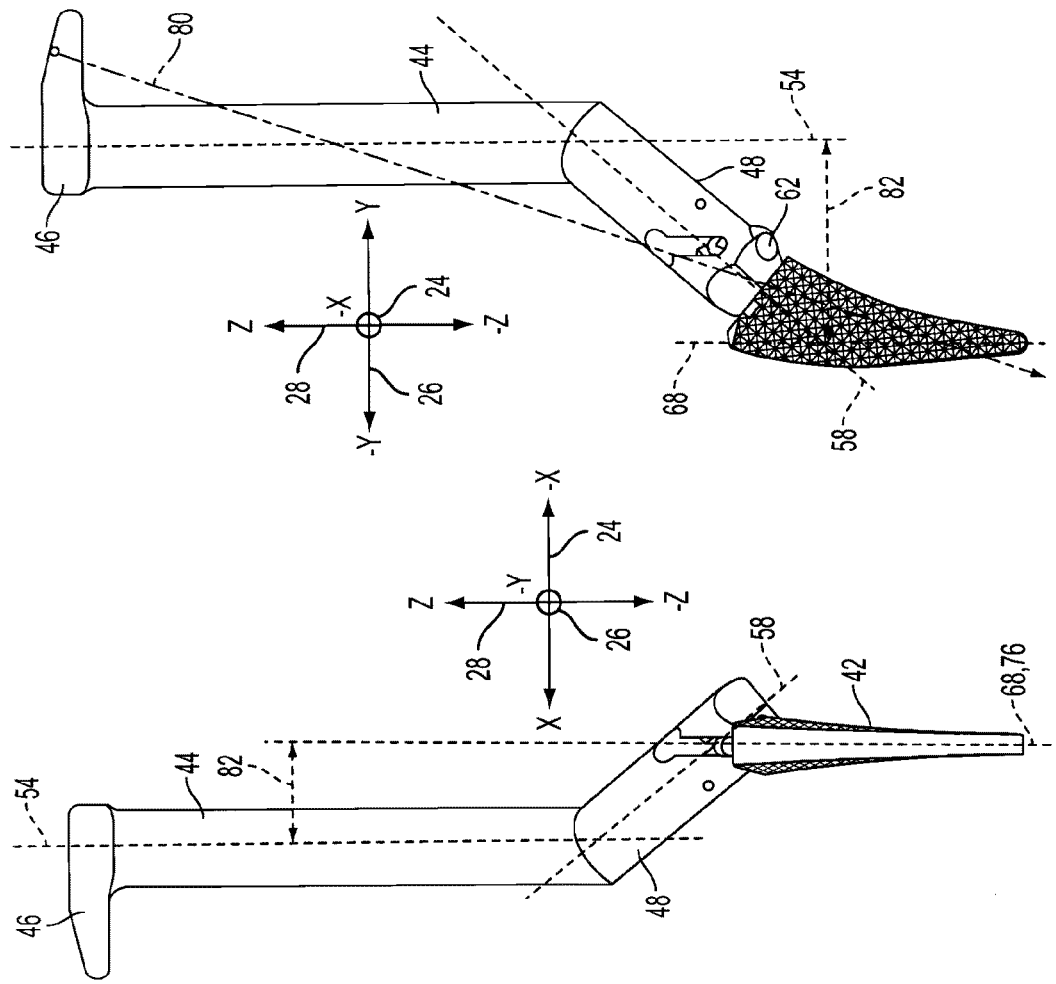

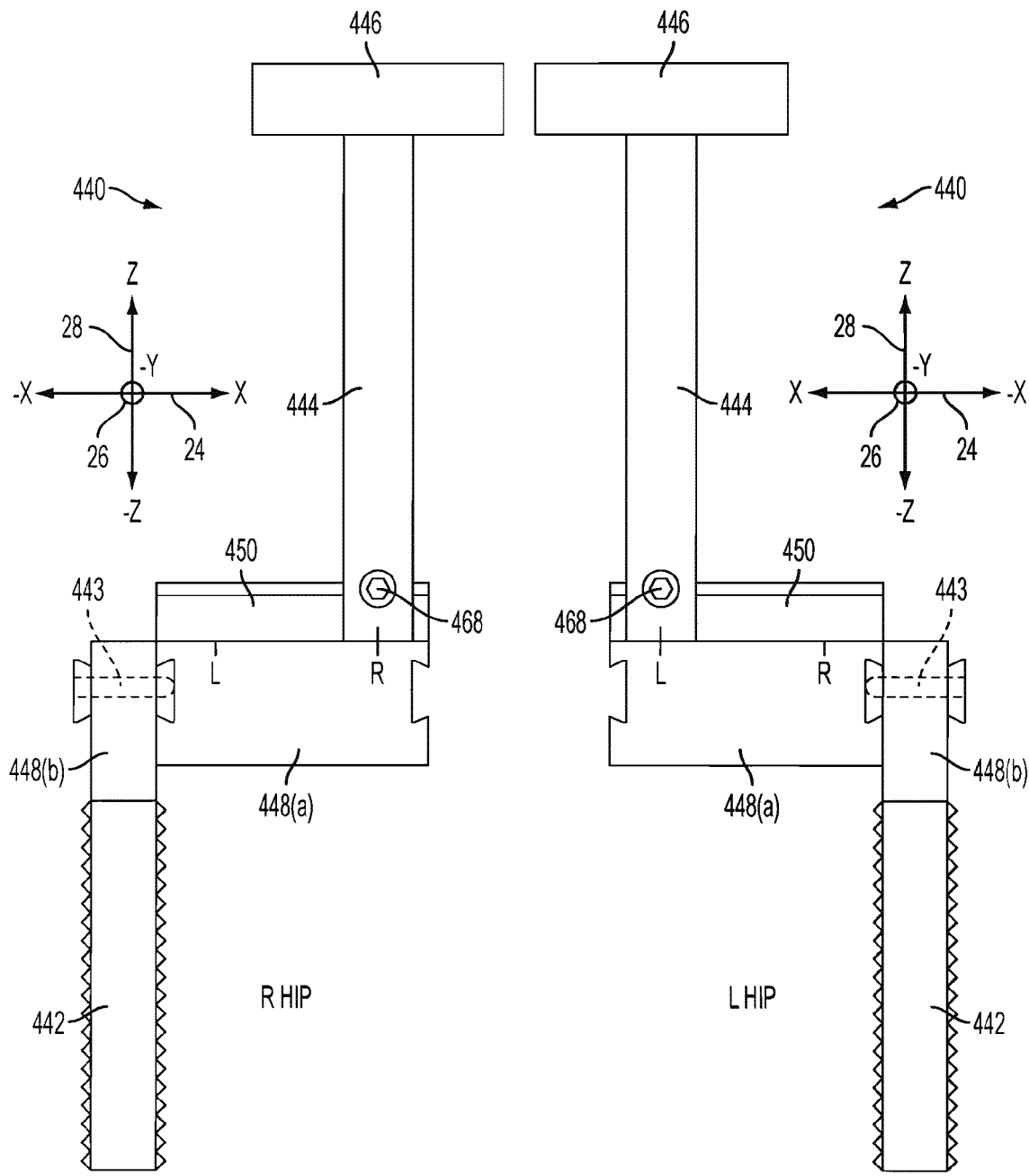

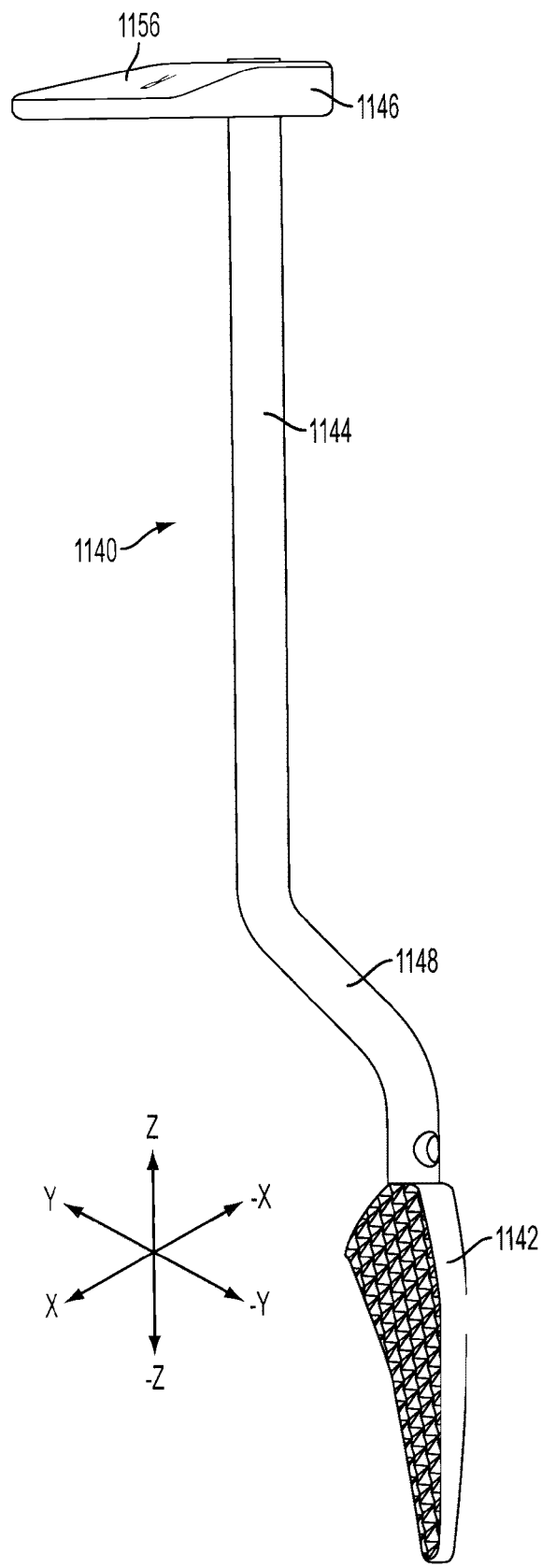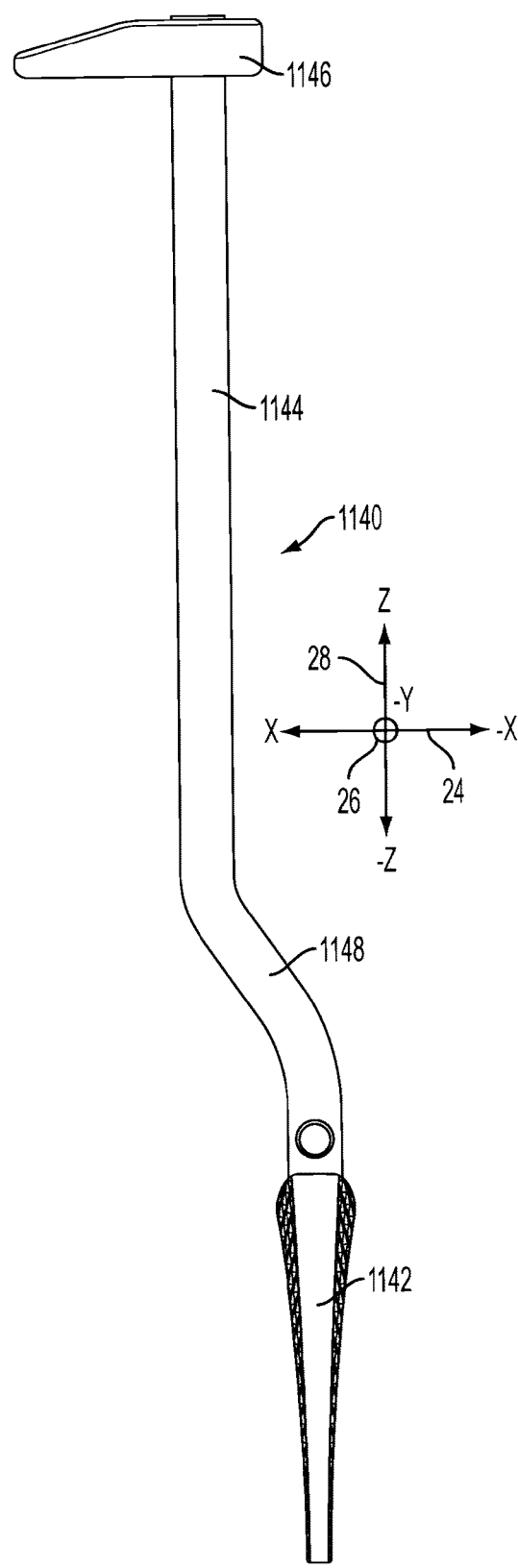
FIG. 47A
FIG. 47B

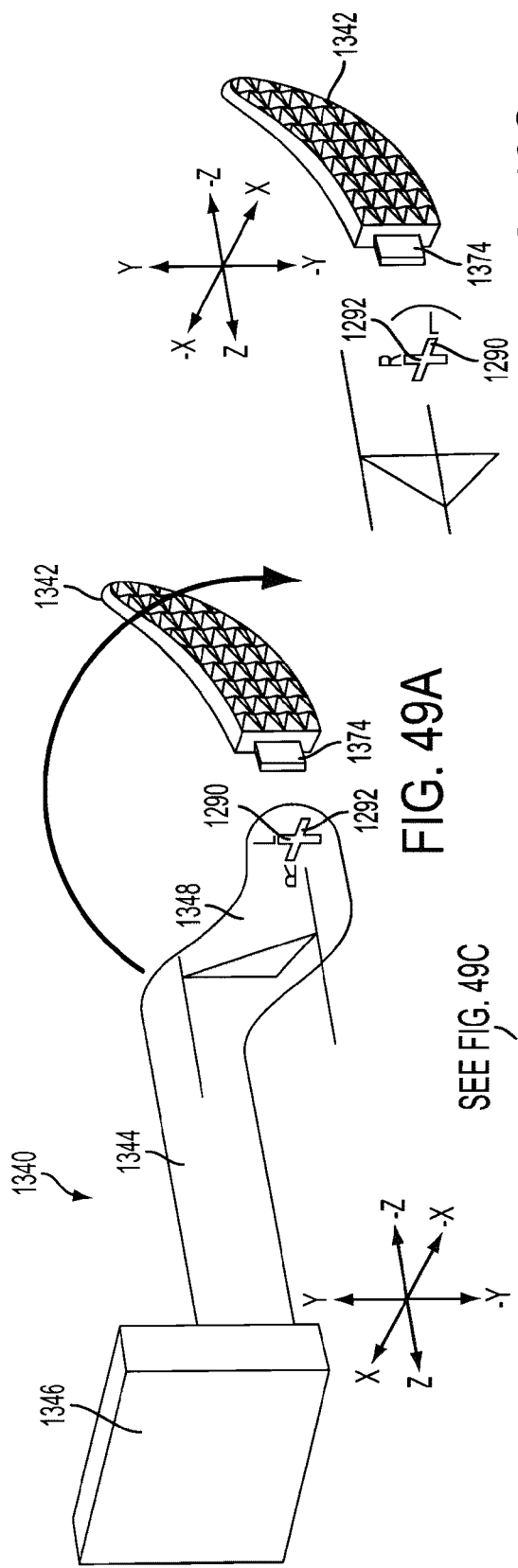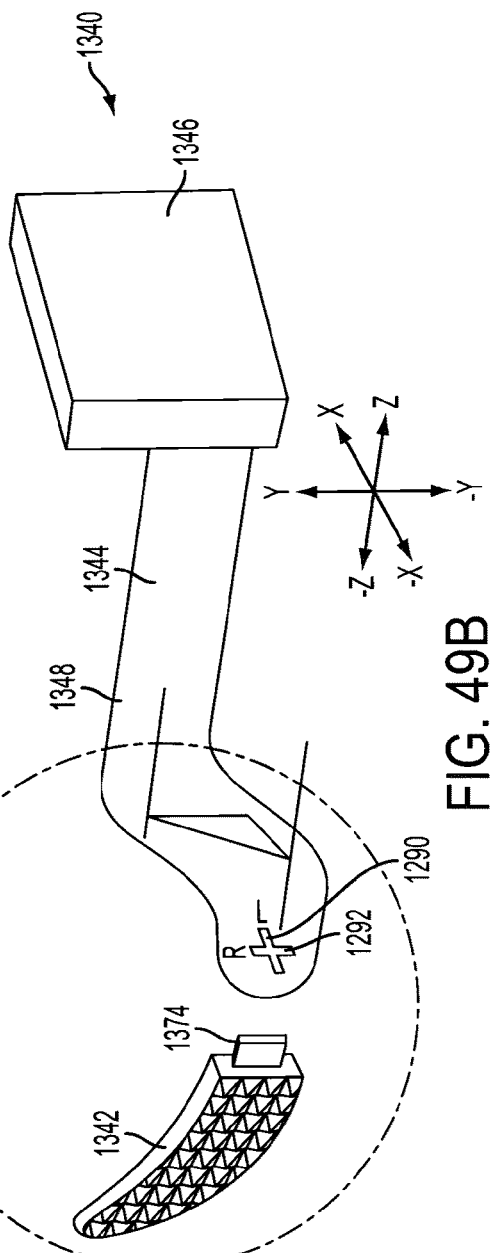

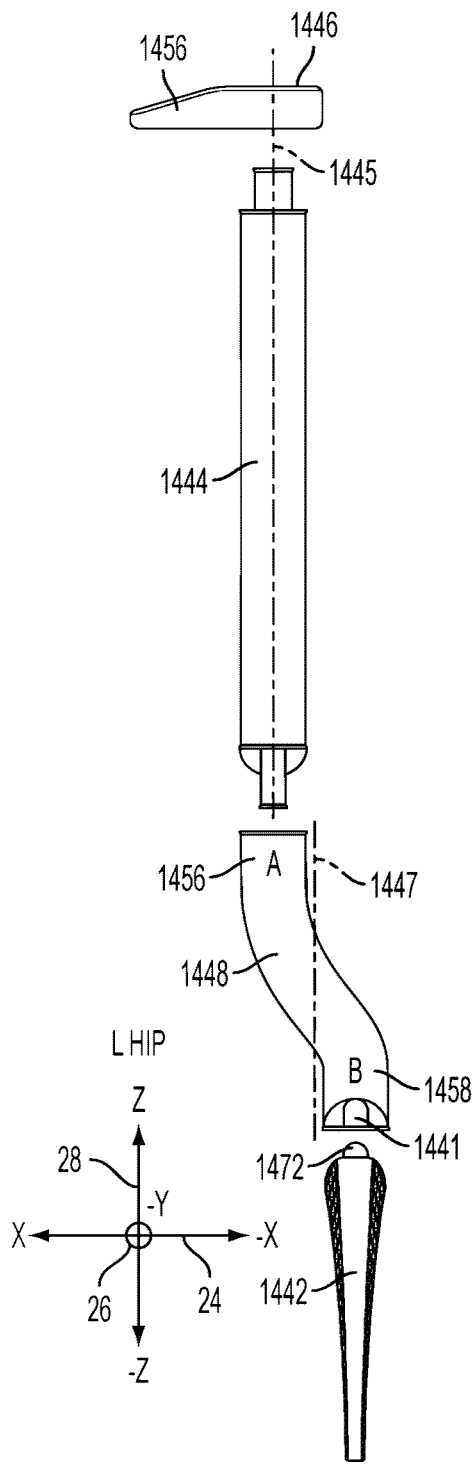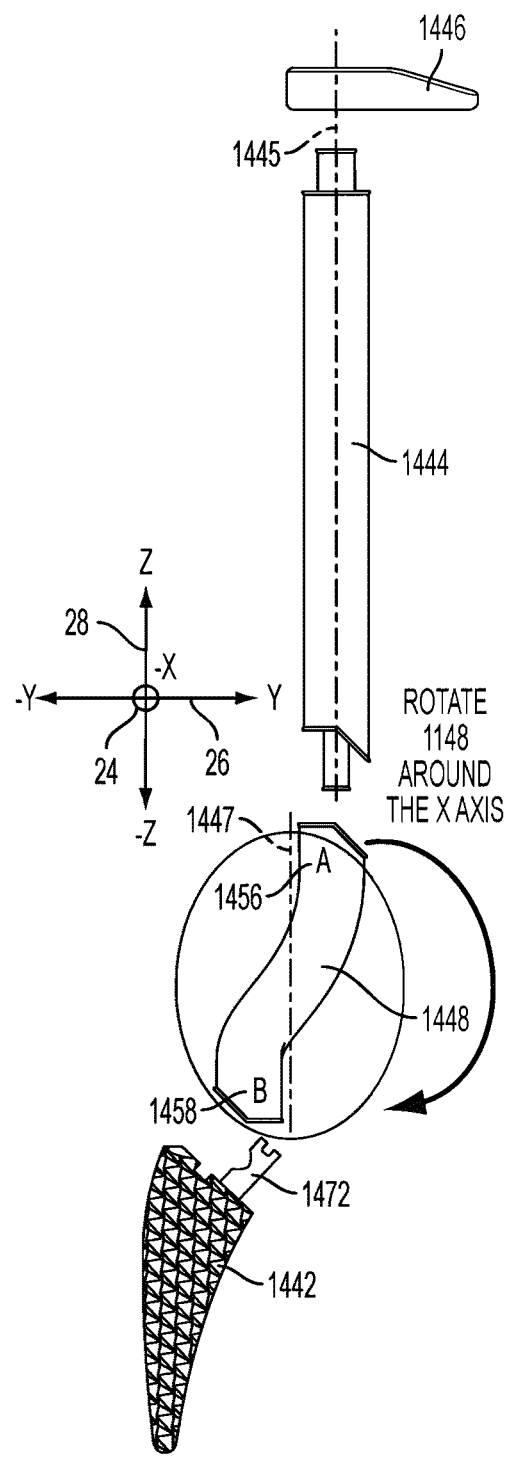
FIG. 50F
FIG. 50G

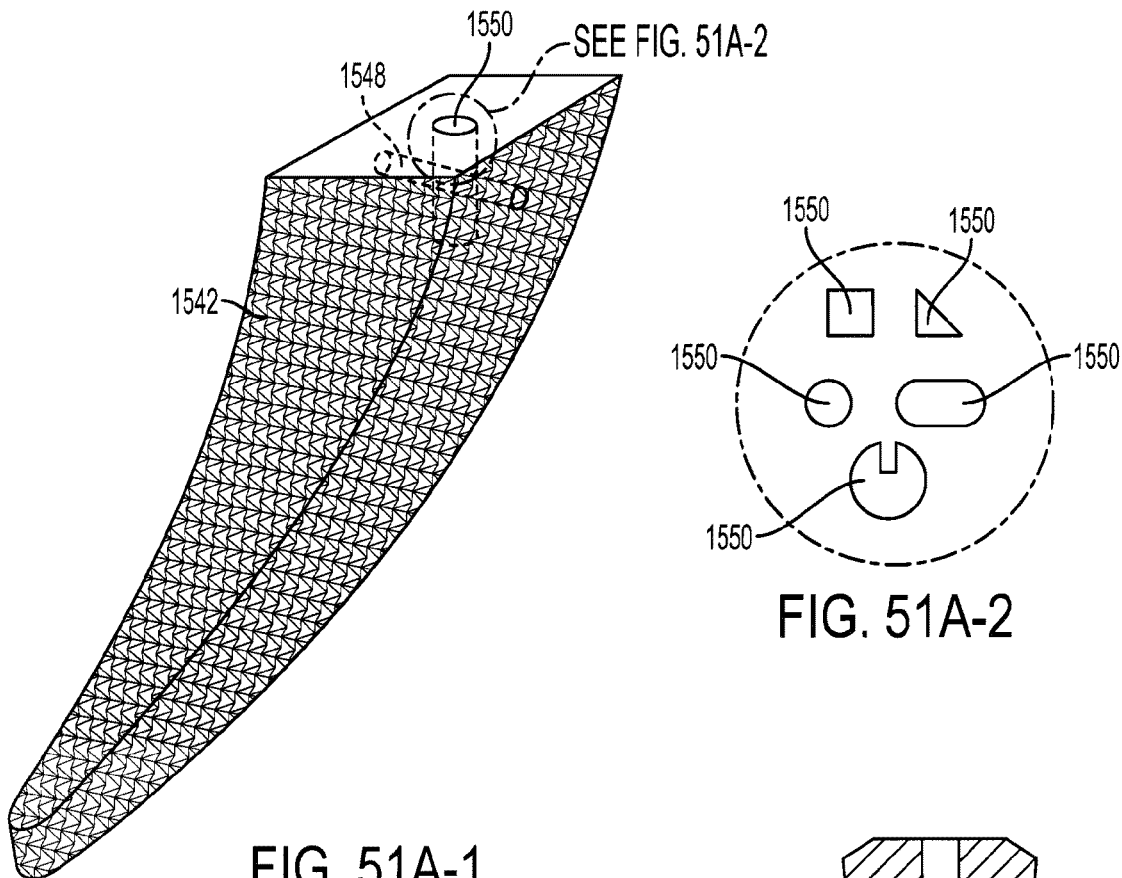
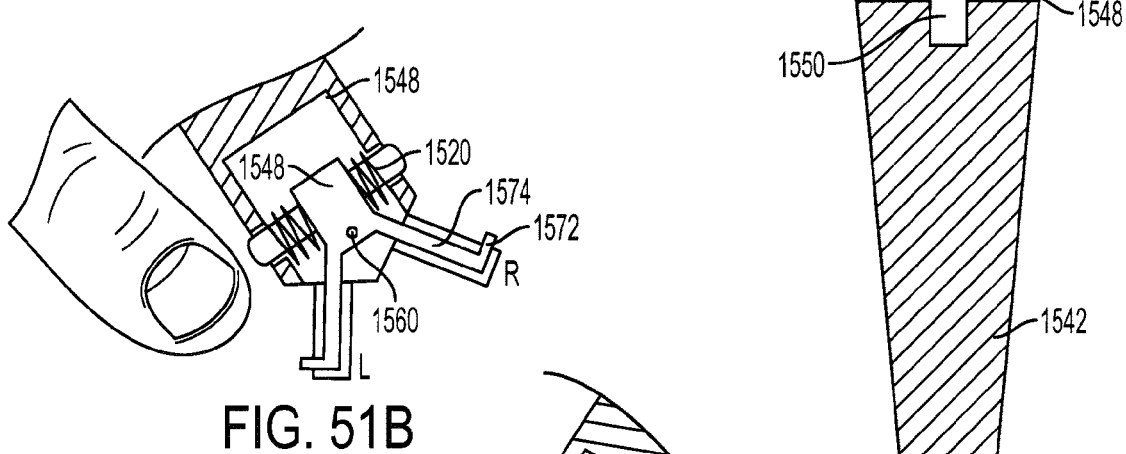
FIG. 51A-1　　FIG. 51A-2
FIG. 51B　　FIG. 51C　　FIG. 51D

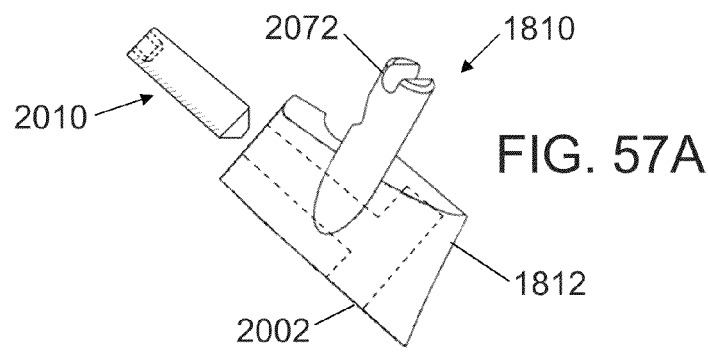
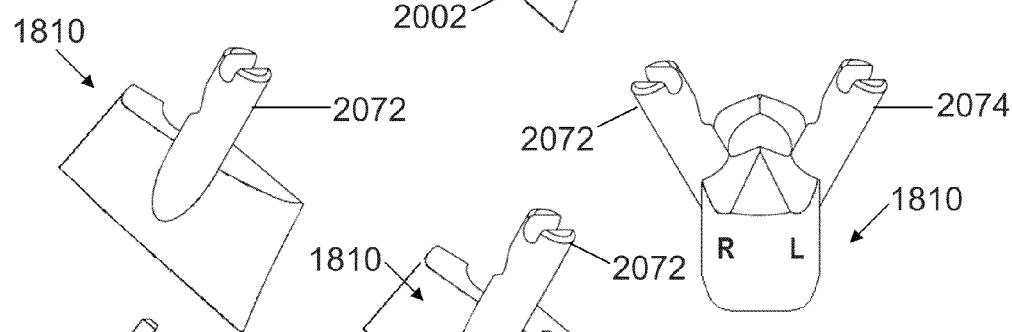
FIG. 57A
FIG. 57B    FIG. 57C    FIG. 57D

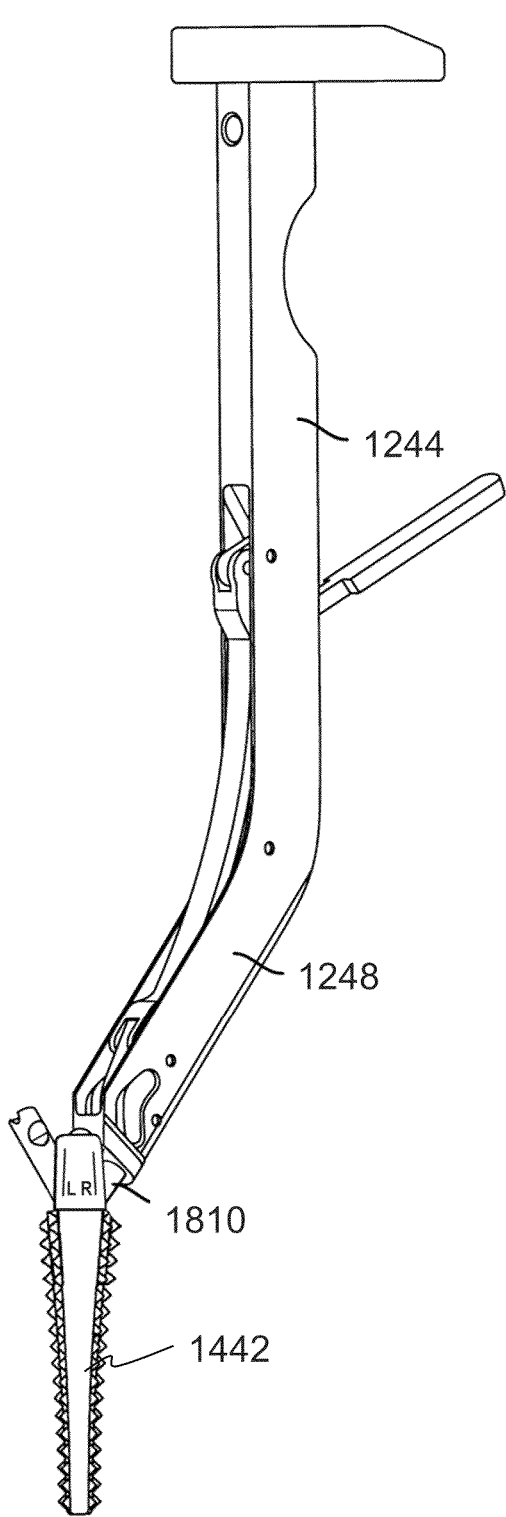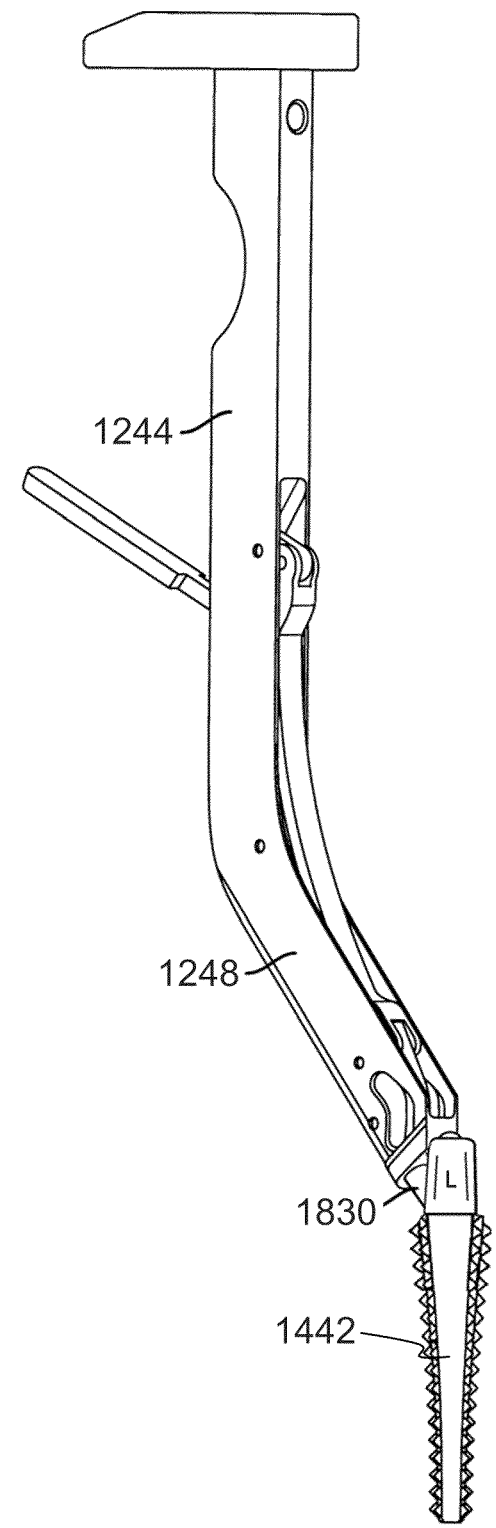
FIG. 57E                                    FIG. 59B

United States Patent US 8,657,824 B2

UNIVERSAL DOUBLE OFFSET SURGICAL INSTRUMENT

CROSS-REFERENCE TO RELATED APPLICATIONS

This application is a continuation-in-part application of U.S. application Ser. No. 12/412,527 filed Apr. 27, 2009 entitled, "Surgical Technique and Instrumentation for Minimal Incision Hip Arthroplasty," which is a continuation application of U.S. application Ser. No. 10/991,641 filed Nov. 18, 2004 entitled, "Surgical Technique and Instrumentation for Minimal Incision Hip Arthroplasty" and which issued on Sep. 22, 2009 as U.S. Pat. No. 7,591,821, which claims priority to U.S. Application Ser. No. 60/520,970 filed Nov. 18, 2003 entitled "Surgical Technique and Instrumentation for Minimal Hip Arthroplasty," all of which are incorporated herein by this reference.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

Embodiments of the invention relate generally to instruments for use in orthopedic surgery, and more particularly to instruments for use in total hip arthroplasty.

2. Background of the Invention

Minimally invasive surgery techniques have become popular in total hip arthroplasty (THA) surgery. Advantages include minimizing soft tissue damage, reducing recovery and healing time, and reducing the length of stay in hospital. One version of such minimally invasive THA techniques is the so-called "anterior approach" or "direct anterior approach" which uses, for instance, a portal between the tensor fascia latae muscle and the rectus femoris muscle. This approach can exploit the interval between those muscles for both acetabular and femoral preparation, allow for primary exposure of the hip joint capsule with minimization of muscle damage, limit incision length, and leverage other advantages.

Exposure of the proximal femoral intramedullary canal in order to prepare the canal to receive the femoral stem can be problematic in such anterior approach THA's, however. Generally, the subject leg can be positioned in extension, external rotation and adduction. The proximal femur can be levered using wing retractors for further exposure of the intramedullary canal to access through the generally shorter than conventional incision. Anatomical features of some patients, such as gut or muscle tissue, can nevertheless present problems in accessing and preparing the femoral canal through the smaller incision. More particularly, leverage of the proximal femur to correct orientation relative to the incision and levering of an instrument directly through the incision to prepare the intramedullary canal can be obstructed by the gut or musculature of some obese or muscular patients. Special instrument handles have been developed for such cases which include anterior and lateral offsets. The bone shaping member, such as a broach or an osteotome, may be connected to the distal end of such a handle, inserted through the incision into the intramedullary canal of the femur, and manipulated to avoid the gut or other musculature by virtue of the anterior and lateral offsets of the handle. See, e.g., M. Nogler, et al., *A Double Offset Shaping Member Handle for Preparation of the Femoral Cavity in Minimally Invasive Direct Anterior Total Hip Arthroplasty*, 21 *J. Arthroplasty*, pp. 1206-1208 (No. 8, 2006); U.S. Ser. No. 10/991,641 filed Nov. 18, 2004 entitled "Surgical Technique and Instrumentation for Minimal Incision Hip Arthroplasty Surgery;" and U.S. Ser. No. 12/412,527 filed Mar. 27, 2009 entitled "Surgical Technique and Instrumentation for Minimal Incision Hip Arthroplasty Surgery." All three of these documents are incorporated herein by this reference.

Such instruments are physically large and heavy however, and separate instruments are required for each of the right and left femurs in order to provide the required lateral offset. Consequent issues include those related to, among other things, logistics, inventory requirement, and expense.

SUMMARY OF THE INVENTION

The present invention relates to instruments for THA and other similar surgeries, which can be used in connection with surgery on the left or right body member, such as a femur.

There is provided:

In one embodiment, an instrument for shaping a medullary canal of both a patient's left leg and right leg, comprising: (a) a handle that includes a handle longitudinal axis; (b) a shaping member including: structure configured to shape bone; a shaping member longitudinal axis, and a connecting structure that includes an interpositional cooperation structure; (c) an offset member that physically connects the handle to the shaping member, the offset member extending in an offset direction that includes a first directional component in a first direction orthogonal to the longitudinal axis of the shaping member, and a second directional component in the direction of the shaping member longitudinal axis; (d) the offset member including: (i) a first opening adapted to receive the shaping member connecting structure, the first opening configured to receive the shaping member connecting structure in a manner whereby the shaping member longitudinal axis is substantially parallel to the handle longitudinal axis; (ii) a second opening adapted to receive the shaping member connecting structure, the second opening configured to receive the shaping member connecting structure in a manner whereby the shaping member longitudinal axis is substantially parallel to the handle longitudinal axis; and (e) a retention device or member comprising an actuator and at last one interpositional structure, the retention device or member configured to interpose the at least one interpositional structure relative to the interpositional cooperation structure of the shaping member connecting structure when the actuator is actuated.

In certain other embodiments, there is provided an instrument wherein the shaping member comprises a reference plane and the first and second openings are configured to receive the shaping member connecting structure in a manner such that the first direction orthogonal to the longitudinal axis of the shaping member bisects the angle formed by the shaping member reference plane when the shaping member is connected to the first opening and the shaping member reference plane when the shaping member is connected to the second opening.

In certain other embodiments, there is provided an instrument wherein the shaping member comprises a reference plane and the first and second openings are configured to receive the shaping member connecting structure in a manner such that when the shaping member is connected to the first opening, the shaping member reference plane is substantially orthogonal to the shaping member reference plane when the shaping member is connected to the second opening.

In certain other embodiments, there is provided an instrument wherein the shaping member is a broach.

In certain other embodiments, there is provided an instrument wherein the shaping member is a femoral shaping member for preparation of a central femoral cavity for receiving a stem of a femoral component of a prosthetic hip.

In certain other embodiments, there is provided an instrument further comprising a strike plate with a first beveled surface that corresponds to the first opening on the offset member and a second beveled surface that corresponds to the second opening on the offset member.

In certain other embodiments, there is provided an instrument wherein the offset member extends in at least two offset directions.

In certain other embodiments, there is provided an instrument wherein the offset direction includes a third directional component that is orthogonal to the first directional component, the second directional component, and the longitudinal axis of the shaping member.

In certain other embodiments, there is provided an instrument wherein the offset member includes a first abutment surface and a second abutment surface, the first abutment surface corresponding to the first opening and configured to abut a proximal surface of the shaping member, the second abutment surface corresponding to the second opening and configured to abut a proximal surface of the shaping member.

In certain other embodiments, there is provided an instrument wherein the actuator of the retention device or member includes an over-center linkage configured to lock the interpositional structure in place when interposed with the interpositional cooperation structure of the shaping member connecting structure, and wherein the interpositional structure comprises at least one pawl.

In certain other embodiments, there is provided an instrument wherein the actuator of the retention device or member includes a wedge, the interpositional structure includes at least one claw, and the wedge is configured to urge the at least one claw into interposed position with the interpositional cooperation structure of the shaping member connecting structure.

In yet another embodiment, there is provided an instrument for operating on a medullary canal for installation of a prosthetic stem component in a patient, comprising: a handle including an elongated shaft extending approximately in a negative z-direction; a first offset capable of extending in a first direction that includes an x-directional component or a negative x-directional component; a second offset extending in a second direction that includes a negative y-directional component; the handle connected to either the first or second offset; an insertion member extending from either the first offset or the second offset in an insertion member direction that includes a negative z-directional component; wherein the negative y-directional component and negative z-directional components are orthogonal to each other and orthogonal to the x-directional component and the negative x-directional component, and wherein the handle and the insertion member are positioned with respect to one another in a non-planar relationship.

In another embodiment, there is provided an instrument wherein one of the offsets is connected to the handle via a pivot capable of rotating relative to the handle such that one of the offsets extends in approximately an x-direction or a negative x-direction in order to configure the instrument for use with a right leg or a left leg of the patient.

In another embodiment, there is provided an instrument wherein the handle is configured to connect to the second offset on either a first side of the handle that faces the x direction or a second side of the handle that faces the negative x direction in order to form the first offset.

In another embodiment, there is provided an instrument wherein the insertion member further comprises cutting elements.

In another embodiment, there is provided an instrument for operating on a medullary canal for installation of a prosthetic stem component in a patient, comprising: a handle including an elongated shaft extending in an approximately negative z-direction; an offset connected to the handle, the offset extending in a first direction that includes a negative y-directional component and capable of extending in a second direction that includes an x-directional component or a negative x-directional component; a shaping member extending from the offset in a shaping member direction that includes a negative z-directional component, wherein the negative y-directional component and negative z-directional components are orthogonal to each other and orthogonal to the x-directional component and the negative x-directional component, wherein the handle and the shaping member are positioned with respect to one another in a non-coplanar relationship, and wherein the shaping member further comprises cutting elements.

In another embodiment, there is provided an instrument wherein the offset is connected to the handle via a pivot, and the handle and pivot are capable of rotating relative to each other such that the offset extends in a direction that includes an x-directional component or a negative x-directional component in order to configure the instrument for use with a right leg or a left leg of the patient.

In another embodiment, there is provided an instrument for operating on a medullary canal for installation of a prosthetic stem component in a patient, comprising: a handle member including a first section that extends in a negative z-direction; a second section that extends in a direction having an x-directional component or a negative x-directional component and a negative y-directional component; and a third section that extends in a direction that includes a negative z-directional component wherein the negative y-directional component and the negative z-directional components are orthogonal to each other and the negative y-directional component and the negative z-directional components are orthogonal to the x-directional component and the negative x-directional component; a strike plate configured to connect to the first section or the third section of the handle member; and a shaping member configured to connect to the first section or the third section of the handle member; wherein when the strike plate is connected to the first section of the handle member and the shaping member is connected to the third section of the handle member, the instrument is configured for operating on a first leg of the patient, and when the strike plate is connected to the third section of the handle member and the shaping member is connected to the first section of the handle member, the instrument is configured for operating on a second leg of the patient.

In another embodiment, there is provided an instrument wherein the shaping member is a femoral shaping member.

In another embodiment, there is provided an instrument wherein the shaping member is a broach.

According to another embodiment, there is provided a method of installing a prosthetic stem component into the medullary canal of a right leg or a left leg of a patient, comprising the steps of: obtaining an instrument capable of shaping a medullary canal of both a patient's left leg and right leg, comprising: (a) a handle that includes a handle longitudinal axis; (b) a shaping member including: structure configured to shape bone; a shaping member longitudinal axis, and a connecting structure that includes an interpositional cooperation structure; (c) an offset member that physically connects the handle to the shaping member, the offset member extending in an offset direction that includes a first directional component in a first direction orthogonal to the longitudinal axis of the shaping member, and a second directional component in the direction of the shaping member longitudinal axis; (d) the offset member including: (i) a first opening adapted to receive the shaping member connecting structure, the first opening configured to receive the shaping member connecting structure in a manner whereby the shaping member longitudinal axis is substantially parallel to the handle longitudinal axis; (ii) a second opening adapted to receive the shaping member connecting structure, the second opening configured to receive the shaping member connecting structure in a manner whereby the shaping member longitudinal axis is substantially parallel to the handle longitudinal axis; and (e) a retention device or member comprising an actuator and at last one interpositional structure, the retention device or member configured to interpose the at least one interpositional structure relative to the interpositional cooperation structure of the shaping member connecting structure when the actuator is actuated; selecting either the left leg or the right leg of the patient as the leg for installation of the prosthetic stem component; configuring the instrument to operate on the selected leg by connecting the shaping member to the first opening or the second opening; inserting the instrument into the medullary canal of the selected leg through a surgical incision; operating on the medullary canal of the selected leg with the instrument; removing the instrument from the medullary canal of the selected leg; installing the prosthetic stem component in the medullary canal of the selected leg; and completing the surgery.

In another embodiment, there is provided a method of installing a prosthetic stem component comprising the step of obtaining an instrument capable of shaping a medullary canal of both a patient's left leg or a right leg includes obtaining an instrument that includes a strike plate connected to the handle, the strike plate including a first beveled surface that corresponds to the first opening on the offset member and a second beveled surface that corresponds to the second opening on the offset member; and the step of operating on the medullary canal of the selected leg with the instrument includes striking the instrument on a predetermined one of the first beveled surface and the second beveled surface.

In another embodiment, there is provided a method of installing a prosthetic stem component into the medullary canal of a right leg or a left leg of a patient, comprising the steps of: obtaining an instrument capable of operating on the medullary canal of the right leg or the left leg of the patient for installation of a prosthetic stem component, comprising a handle including a shaft extending downward approximately in a negative z-direction, a first offset configured to extend from a bottom of the elongated shaft in a first direction that includes an x-directional component or a negative x-directional component, a second offset extending from the first offset in a second direction that includes a negative y-directional component, and a shaping member including structure configured to shape bone, the shaping member extending downward from the second offset in a shaping member direction that includes a negative z-directional component, wherein the negative y-directional component and the negative z-directional component are orthogonal to each other, and the negative y-directional component and the negative z-directional component are orthogonal to the x-directional component and the negative x-directional component, and wherein the handle and the shaping member are positioned with respect to one another in a non-planar relationship; selecting either the left leg or the right leg of the patient as the leg for installation of the prosthetic stem component; configuring the instrument to operate on the selected leg by causing the first offset to extend from the handle in either the direction that includes the x-directional component or the direction that includes the negative-x directional component; inserting the instrument into the medullary canal of the selected leg through a surgical incision; operating on the medullary canal of the selected leg with the instrument; removing the instrument from the medullary canal of the selected leg; installing the prosthetic stem component in the medullary canal of the selected leg; and completing the surgery.

In another embodiment, there is provided a method of installing a prosthetic stem component into the medullary canal of a right leg or a left leg of a patient comprising the step of obtaining an instrument capable of operating on the medullary canal of the right leg or the left leg of the patient includes obtaining an instrument that includes a strike plate connected to the handle, the strike plate including a first beveled surface that corresponds to the first opening on the offset member and a second beveled surface that corresponds to the second opening on the offset member; and the step of operating on the medullary canal of the selected leg with the instrument includes striking the instrument on a predetermined one of the first beveled surface and the second beveled surface.

In another embodiment, there is provided a method of installing a prosthetic stem component into the medullary canal of a right leg or a left leg of a patient wherein the step of inserting the instrument into the medullary canal of the selected leg comprises inserting the instrument into an anterior surgical incision.

In yet another embodiment, there is provided a method of installing a prosthetic stem component into the medullary canal of a right leg or a left leg of a patient wherein the step of inserting the instrument into the medullary canal of the selected leg comprises inserting the instrument into a minimally invasive surgical incision.

In yet another embodiment, there is provided a method of installing a prosthetic stem component into the medullary canal of a right leg or a left leg of a patient wherein the step of inserting the instrument into the medullary canal of the selected leg comprises inserting the instrument into a surgical incision that is from approximately 4 cm to approximately 16 cm in length.

In yet another embodiment, there is provided a method of installing a prosthetic stem component into the medullary canal of a right leg or a left leg of a patient wherein the step of inserting the instrument into the medullary canal of the selected leg comprises inserting a femoral shaping member.

In yet another embodiment, there is provided a method of installing a prosthetic stem component into the medullary canal of a right leg or a left leg of a patient wherein the step of inserting the instrument into the medullary canal of the selected leg comprises inserting a broach.

In another embodiment, there is provided a method of installing a prosthetic stem component into the medullary canal of a right leg or a left leg of a patient, comprising the steps of: obtaining an instrument capable of operating on the medullary canal of the right leg or the left leg of the patient for installation of a prosthetic stem component, the instrument comprising: a handle including an elongated shaft extending approximately in a negative z-direction; an offset connected to the handle, the offset extending in a first direction that includes a negative y-directional component and capable of extending in a second direction that includes an x-directional component or a negative x-directional component; a shaping member extending downward the offset in a shaping member direction that includes a negative z-directional component, wherein the negative y-directional component and negative z-directional components are orthogonal to each other and orthogonal to the x-directional component and the negative x-directional component, wherein the handle and the shaping member are positioned with respect to one another in a non-planar relationship, and wherein the shaping member further comprises cutting elements; selecting either the left leg or the right leg of the patient as the leg for installation of the prosthetic stem component; configuring the instrument to operate on the selected leg by causing the first offset to extend from the handle in either the direction that includes the x-directional component or the direction that includes the negative-x directional component; inserting the instrument into the medullary canal of the selected leg through a surgical incision; operating on the medullary canal of the selected leg with the instrument; removing the instrument from the medullary canal of the selected leg; installing the prosthetic stem component in the medullary canal of the selected leg; and completing the surgery.

In another embodiment, there is provided a method of installing a prosthetic stem component into the medullary canal of a right leg or a left leg of a patient wherein the step of obtaining an instrument capable of operating on the medullary canal of the right leg or the left leg of the patient includes obtaining an instrument that includes a strike plate connected to the handle, the strike plate including a first beveled surface that corresponds to the first opening on the offset member and a second beveled surface that corresponds to the second opening on the offset member; and the step of operating on the medullary canal of the selected leg with the instrument includes striking the instrument on a predetermined one of the first beveled surface and the second beveled surface.

In another embodiment, there is provided a method of installing a prosthetic stem component into the medullary canal of a right leg or a left leg of a patient wherein the step of inserting the instrument into the medullary canal of the selected leg comprises inserting a femoral shaping member.

In another embodiment, there is provided a method of installing a prosthetic stem component into the medullary canal of a right leg or a left leg of a patient wherein the step of inserting the instrument into the medullary canal of the selected leg comprises inserting a broach. According to another embodiment, there is provided a method of installing a prosthetic stem component into the medullary canal of a right leg or a left leg of a patient, comprising the steps of: obtaining an instrument capable of operating on a medullary canal for installation of a prosthetic stem component in a patient, comprising: a handle member including a first section that extends in a negative z-direction; a second section that extends in a direction having (i) an x-directional component or a negative x-directional component and (ii) a negative y-directional component; and a third section that extends in a direction that includes a negative z-directional component wherein the x-directional component, the negative y-directional component and the negative z-directional components are orthogonal to each other; a strike plate configured to connect to the first section or the third section of the handle member; and a shaping member configured to connect to the first section or the third section of the handle member; wherein when the strike plate is connected to the first section of the handle member and the shaping member is connected to the third section of the handle member, the instrument is configured for operating on a first leg of the patient, and when the strike plate is connected to the third section of the handle member and the shaping member is connected to the first section of the handle member, the instrument is configured for operating on a second leg of the patient; selecting either the left leg or the right leg of the patient as the leg for installation of the prosthetic stem component; configuring the instrument to operate on the selected leg by connecting the shaping member to one of the first or third section of the handle and connecting the strike plate to the other of the first or third section of the handle; inserting the instrument into the medullary canal of the selected leg through a surgical incision; operating on the medullary canal of the selected leg with the instrument; removing the instrument from the medullary canal of the selected leg; installing the prosthetic stem component in the medullary canal of the selected leg; and completing the surgery.

In another embodiment, there is provided a method of installing a prosthetic stem component into the medullary canal of a right leg or a left leg of a patient wherein the step of obtaining an instrument capable of operating on a medullary canal includes obtaining an instrument wherein the strike plate includes a first beveled surface that corresponds to the left leg of the patient and a second beveled surface that corresponds to the right leg of the patient; and the step of operating on the medullary canal of the selected leg with the instrument includes striking the instrument on a predetermined one of the first beveled surface and the second beveled surface.

In another embodiment, there is provided an instrument comprising a separate adapter component that comprises the offset.

In another embodiment, there is provided an adapter capable of joining a handle to a shaping member for shaping a medullary canal of a patient's leg, the handle having a handle longitudinal axis and the shaping member having a shaping member longitudinal axis, the adapter comprising: (a) a body; and (b) at least one post connected to the body and configured to connect to the handle; and (c) a cavity that receives the insertion member in a locking manner, wherein a longitudinal axis of the post relative to a longitudinal axis of the cavity is oriented to connect the shaping member in a manner whereby the shaping member longitudinal axis is substantially parallel to the handle longitudinal axis; and wherein the adapter extends in an offset direction that includes a first directional component in a first direction orthogonal to the longitudinal axis of the shaping member, and a second directional component in the direction of the shaping member longitudinal axis.

In another embodiment, there is provided an adapter wherein the adapter comprises two posts, one of the posts being configured for shaping the medullary canal of a patient's right leg and the other of the posts being configured for shaping the medullary canal of a patient's left leg.

BRIEF DESCRIPTION OF THE DRAWINGS

The accompanying drawings, which are incorporated in and form a part of the specification, illustrate certain embodiments of the present invention and together with the description, serve to explain the principles of the invention. In the drawings:

FIG. 20 shows a posterior perspective view of the instrument assembly of FIG. 6.

FIG. 21 shows a medial perspective view of the instrument assembly of FIG. 20.

FIG. 22 shows an elevated perspective view of the instrument assembly of FIG. 20.

FIG. 38B shows a posterior perspective view of the instrument of FIG. 38A, with the instrument positioned for operating on a right femur.

FIG. 38C shows a posterior perspective view of the instrument of FIG. 38A, with the instrument positioned for operating on a left femur.

FIG. 47A shows a perspective view of an eleventh alternate embodiment according to the present invention configured for operating on a left femur.

FIG. 47B shows a posterior perspective view of the instrument of FIG. 47A.

FIG. 49A shows an exploded view of a thirteenth embodiment of an instrument according to the present invention, with a shaping member positioned for operating on the left femur.

FIG. 49B shows a partial exploded view of the instrument of FIG. 49A, with a shaping member positioned for operating on the right femur.

FIG. 49C shows an alternate view of FIG. 49B.

FIG. 50F shows an exploded view of the instrument of FIG. 50C from a posterior perspective.

FIG. 50G shows a medial perspective view of the instrument of FIG. 50F, showing how the offset component may be rotated for operating on a right femur.

FIG. 51A-1 shows a perspective view of another version of a shaping member according to the present invention.

FIG. 51A-2 shows a top view of the shaping member of FIG. 51A-1.

FIGS. 51B and 51C show distal ends of an instrument according to other embodiments of the present invention.

FIG. 51D shows a cross-sectional view of the shaping member of FIG. 51A.

FIG. 52A-1 shows a perspective view of another version of a shaping member according to the present invention.

FIG. 52A-2 shows a top view of the shaping member of FIG. 52A-1.

FIGS. 57A-D show an adapter according to one embodiment of the present invention.

FIG. 57E shows the adapter of FIG. 57A connected to a handle and configured for operating on a right femur.

FIG. 59B shows the adapter of FIG. 59A connected to a handle and a shaping member.

DETAILED DESCRIPTION OF THE EMBODIMENTS

Figure 1:
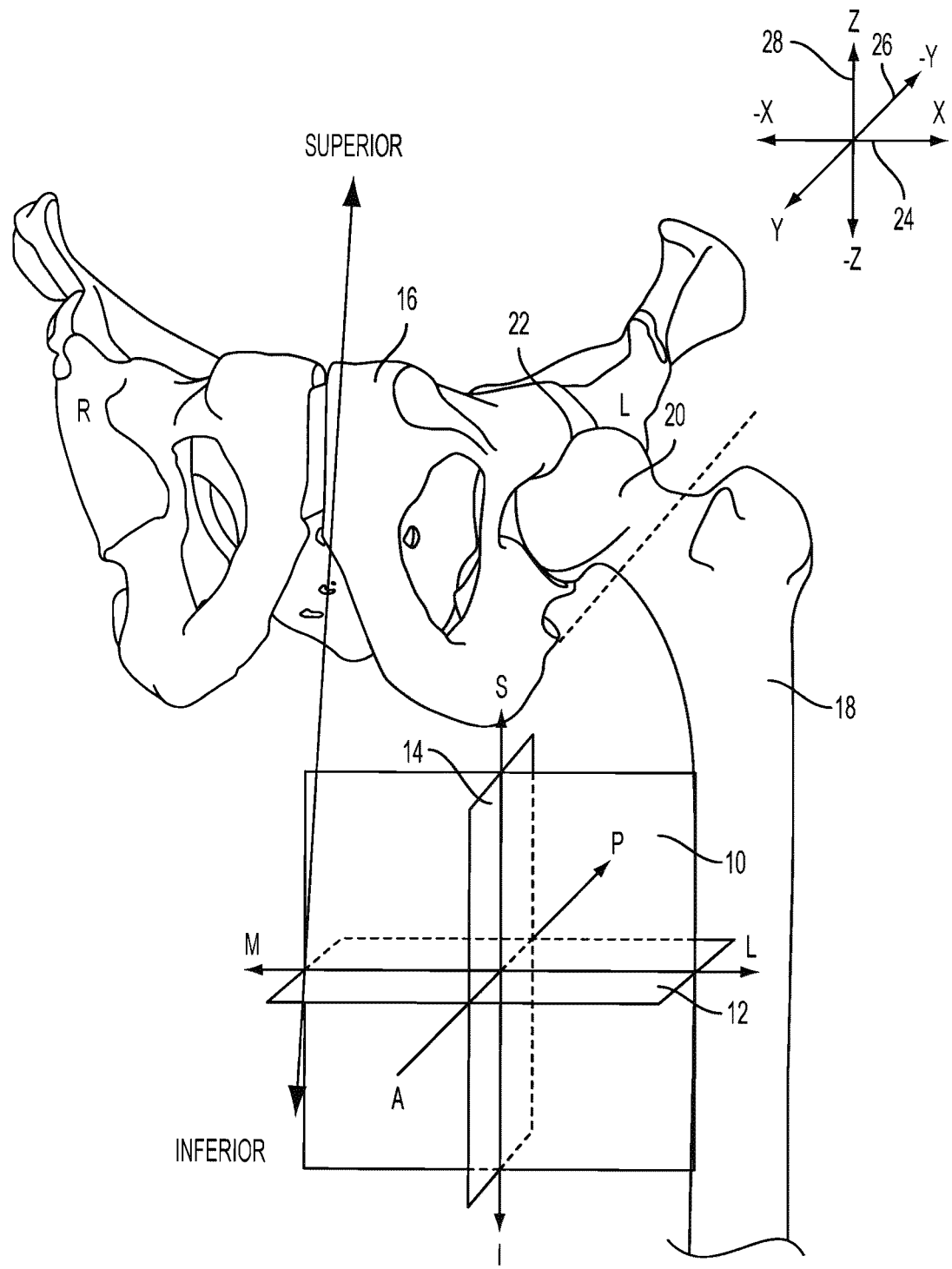
FIG. 1 schematically shows portions of anatomy relevant to embodiments of the present invention, including a left femur positioned relative to an acetabulum and pelvic cage; the drawing also includes reference axes and coordinate systems.

FIGS. 1-5 are provided for context. FIG. 1 shows sawbones corresponding to human bone anatomy from a frontal aspect in the context of coronal plane 10, transverse plane 12, and sagittal plane 14. Coronal plane 10, transverse plane 12, and sagittal plane 14 are conventional surgical reference planes and are oriented orthogonally to one another. In the context of THA anterior approach surgery, the patient, whose anatomy includes pelvic cage 16 and femur 18, is positioned on an operating table face up. Accordingly, FIG. 1 shows the pelvic cage 16 and the femur 18 from an anterior or coronal plane 10 aspect. Femur 18 includes femoral head 20 which is received in hip cup or acetabulum 22.

Corresponding to coronal plane 10, transverse plane 12 and sagittal plane 14, are reference axes X, Y and Z also shown in FIG. 1 and labeled 24, 26 and 28 respectively. Axis 24 includes an X direction and a negative X direction. For purposes of this document, the X direction of axis 24 always corresponds to the patient's lateral side, while the negative X direction of axis 24 always corresponds to the patient's medial side. Thus, the X direction and negative X direction are different from the idea of patient left and patient right. Axis 26 includes a Y direction and a negative Y direction which correspond to the anterior and posterior directions respectively. Axis 28 includes a Z direction and a negative Z direction, which correspond to the superior and inferior directions respectively. For purposes of this document, axes X, Y and Z (24, 26, and 28) can be used to define directions which include components along one or more of the axes.

The coordinate system that includes coronal plane 10, transverse plane 12, and sagittal plane 14 generally corresponds to the orientation of the patient's anatomy. For purposes of this document, it can also correspond to the X, Y and Z coordinate system using axes 24, 26 and 28 as shown in FIG. 1, except that the X direction and negative X direction always refer to the patient's lateral and medial directions, respectively, where "lateral" corresponds to a direction toward the outside of the patient's body and "medial" corresponds to a direction toward the inside of the patient's body. Thus, on both the left and right side of a patient's body, the X direction is lateral, and on both the left and right side of a patient's body the negative X direction is medial. See, for example, FIG. 10.

The coordinate system that includes axes 24, 26 and 28 can also exist at any orientation in space independent of coronal plane 10, transverse plane 12, and sagittal plane 14 of a particular patient, such as the patient whose anatomy is shown in FIG. 1. It is sometimes useful, such as in certain instances discussed later in this document, to consider the structure of a particular instrument in the context of the coordinate system that includes axes 24, 26 and 28, even where that instrument and that coordinate system have been removed from the immediate vicinity of a particular patient or his or her coronal plane 10, transverse plane 12 and sagittal plane 14. Accordingly, the coordinate system that includes axes 24, 26 and 28 should be considered as convenient for defining directions of particular structural components of instruments according to certain embodiments of the invention relative to each other, although not absolutely in terms of a particular direction such as magnetic north, a radius of the earth, or a meridian of longitude. As an example, some drawings in this document show instruments in the context of reference axes: The page that bears the drawing showing the instrument and coordinate system that includes 24, 26 and 28 can be translated and rotated in space in at least 6 degrees of freedom, and the image of the instrument and the coordinate system will similarly translate and rotate but nevertheless continue to show location and orientation of components of the instrument relative to each other regardless of how the translation or rotation of the page or the instrument may vary.

Nevertheless, as shown in FIG. 1, it is sometimes useful to consider the instrument as it is aligned relative to the patient, and thus the Cartesian coordinate system that includes axes 24, 26 and 28 with the surgical reference system that includes the frontal, sagittal and coronal planes. In that case, the Z direction of axis 28 corresponds to the superior direction, while the negative Z direction of axis 28 corresponds to the inferior direction relative to the patient's anatomy. Similarly, the Y direction of axis 26 corresponds to the anterior direction, while the negative Y direction corresponds to the posterior direction. Moreover, for purposes of this document, the X direction of axis 24 corresponds to a lateral direction of the patient, while the negative X direction of axis 24 corresponds to a medial direction of the patient, as shown in FIG. 1.

Figure 2:
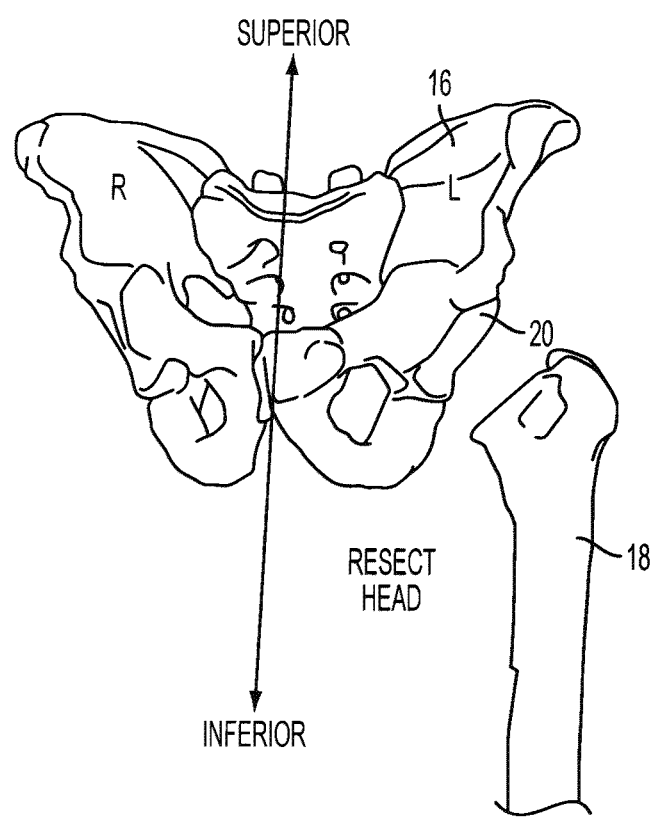
FIG. 2 shows the anatomy of FIG. 1 with the femoral head resected.
Figure 3:
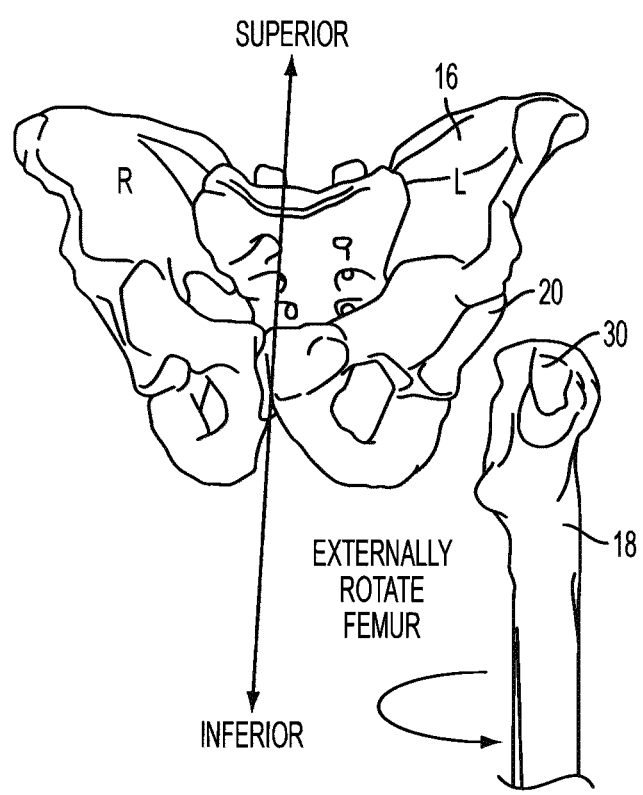
FIG. 3 shows the anatomy of FIG. 2 with the femur further externally rotated for exposure of the intramedullary canal.
Figure 4:
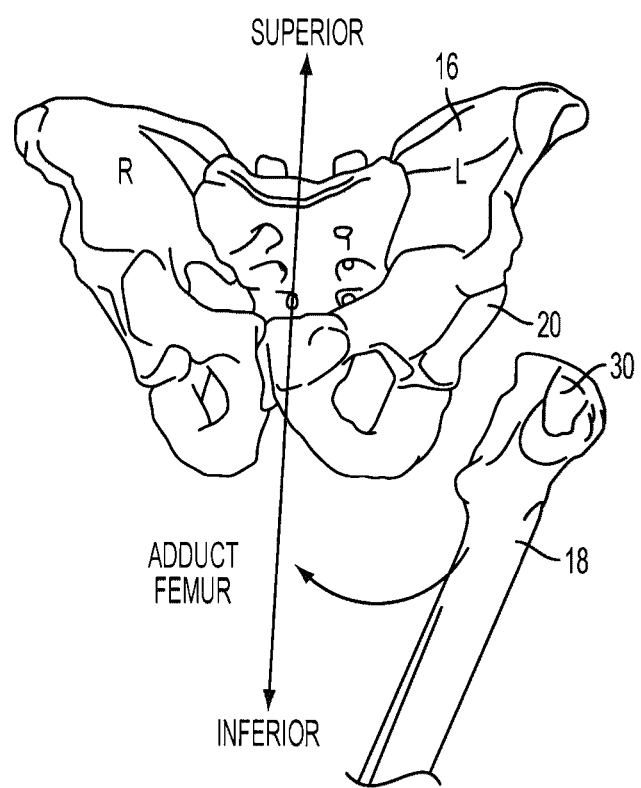
FIG. 4 shows the anatomy of FIG. 3 with the femur further adducted for additional exposure of the intramedullary canal.

FIG. 2 shows the femur 18 of FIG. 1 after resection. FIGS. 3 and 4 show the femur 18 externally rotated and adducted, respectively, to expose the intramedullary canal 30 that will ultimately receive the femoral component of a femoral implant of a total hip prosthesis. FIGS. 3 and 4 are for illustrative purposes only and show an intramedullary canal 30 that has been at least partly shaped. These figures accordingly do not necessarily precisely reflect what the proximal portion of the intramedullary canal 30 and femur 18 will look like after resection, rotation and adduction.

Figure 5:
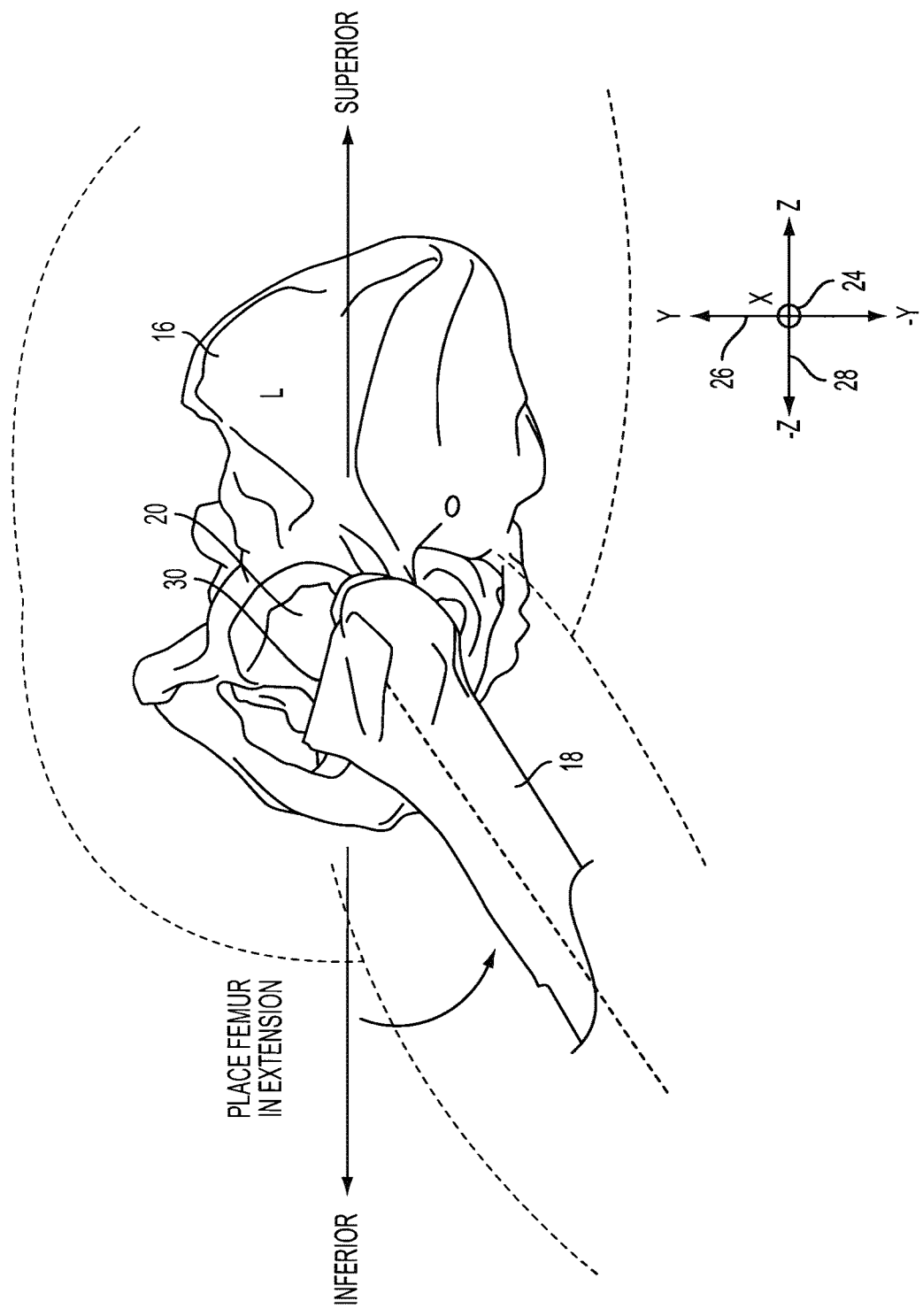
FIG. 5 shows the anatomy of FIG. 4, showing the femur further placed in extension for yet additional exposure of the intramedullary canal.

FIG. 5 is a sagittal view that shows the externally rotated and adducted femur 18 also placed in extension to further expose the intramedullary canal 30 for preparation using an instrument according to an embodiment of the invention. Intramedullary canal preparation is generally necessary in order ultimately to receive a femoral component. It should be noted that only some hospitals have surgical tables that enable such extension of the femur. The instruments disclosed herein are especially useful in instances where the extension step shown in FIG. 5 is not possible due to equipment limitations.

Figure 6:
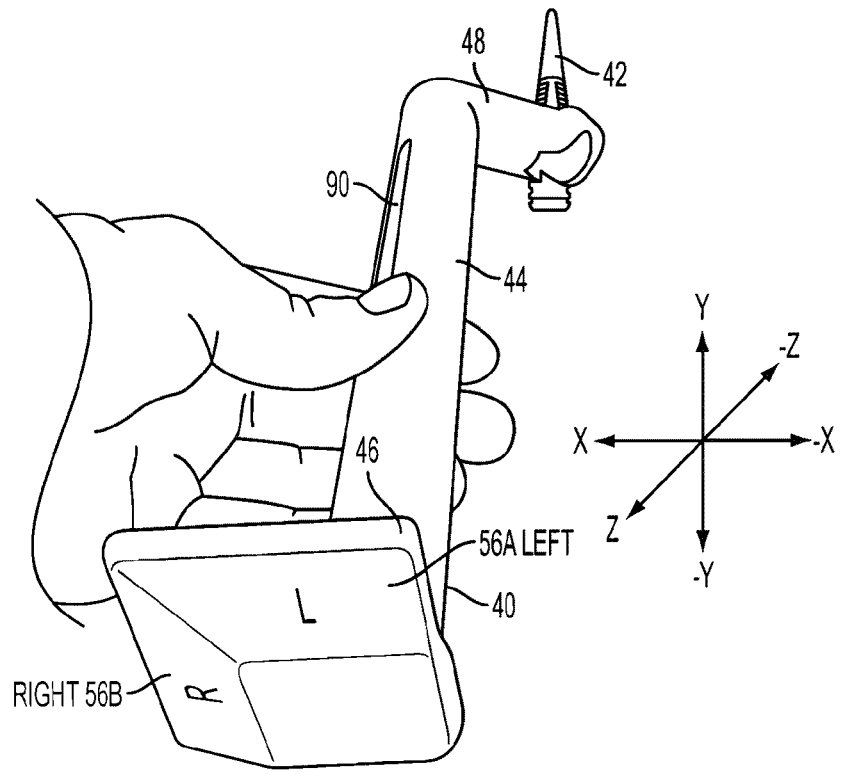
FIG. 6 shows a perspective view of an instrument according to a first embodiment of the present invention assembled with an insertion member in a first configuration for operating on the left femur.
Figure 7:
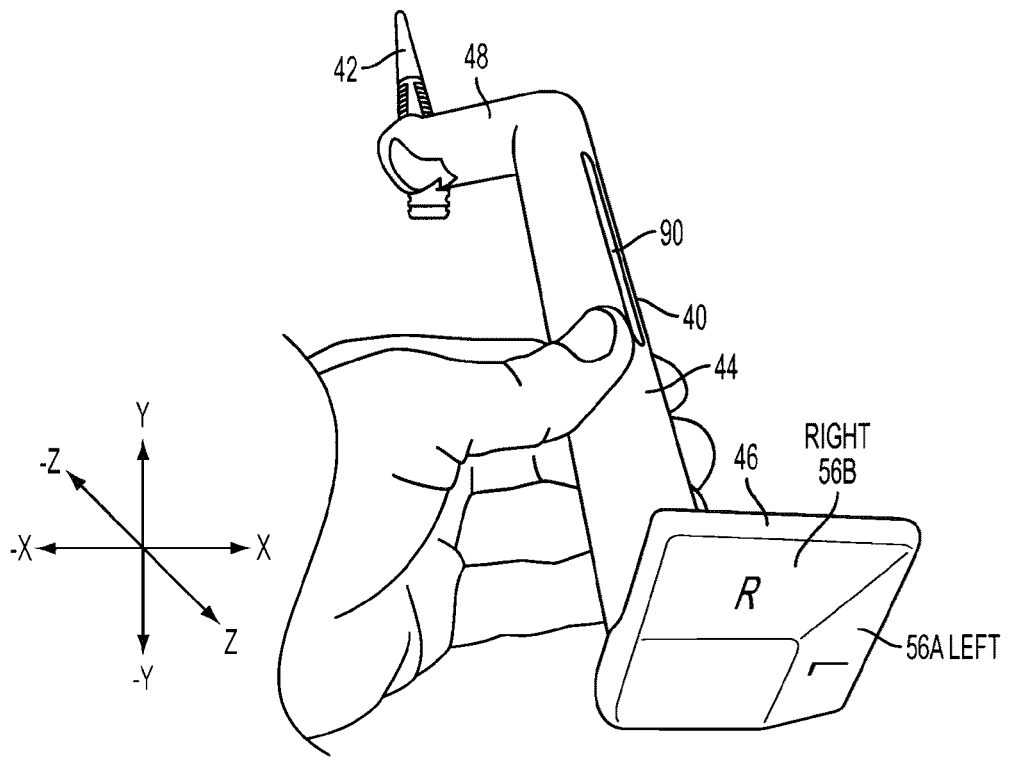
FIG. 7 shows a perspective view of the instrument assembly of FIG. 6 in a second configuration for operating on the right femur.

FIGS. 6 and 7 show an instrument 40 according to a first embodiment of the present invention that can be used to prepare the intramedullary canal of either or both a left or right femur for total hip replacement or other hip surgery. Instrument 40 shown in FIGS. 6 and 7 connects to, and can be considered to include when assembled, a shaping member 42. FIGS. 6 and 7 show the shaping member 42 in the form of a broach but any shaping member such as a reamer, osteotome, sawblade, graft impaction member, broach or other device configured to prepare the intramedullary canal of a bone can be used as a shaping member 42. It should be noted that instead of a shaping member 42, instrument 40 may be advantageously configured to allow insertion of an intramedullary implant such as a femoral stem, for instance, through the use of an adaptor or otherwise. Instrument 40 may be formed of any desired material with appropriate strength, manufacturability, autoclavability, cost, and other desired performance factors. A preferred embodiment is formed of surgical grade stainless steel, but other metal and/or plastic materials may be used, and combinations of materials may be used.

Instrument 40 shown in FIGS. 6 and 7 generally also includes a handle 44 whose proximal portion is connected to a strike plate 46 and whose distal portion is connected to an offset 48 which in turn connects to the shaping member 42.

Handle 44 of the particular instrument 40 shown in FIGS. 6 and 7 is a straight elongated structure with a tubular cross section and a longitudinal axis 54 aligned with the length of handle 44. A cross-section of handle 44 can be tubular, rectangular shaped, or any other desired shape and hollow, partially hollow, solid or as otherwise desired. Primarily, handle 44 serves to provide the surgeon structure to grip and manipulate instrument 40 during surgery while allowing the surgeon also to impact strike plate 46 or an end of instrument 40 with appropriate striking structures such as hammers or other devices. In other embodiments which are not shown, the handle 44 and the offset 48 may be blended together to form an arc to reduce material use and provide better clearance from a patient's gut zone, musculature and/or other body portions.

Strike plate 46 of instrument 40, which is optional, can be a structure of any desired shape and configuration formed at or connected to a proximal portion of handle 44. For example, while not shown in the drawings, strike plate 46 may alternately be configured as an integral slap hammer. Among other things, strike plate 46 can enlarge the surface on which the surgeon strikes instrument 40 with a striking device such as a hammer or mallet to operate on bone. Strike plate 46 can also provide striking surfaces that are offset from the longitudinal axis of the handle 44 in order to enhance transmission of force from impact of the striking device on instrument 40 to the shaping member 42 as it interacts with the bone. Additionally, strike plate 46 can include one or more beveled surfaces 56A and 56B. Strike surface 56A serves as the left hip strike plate surface and 56B serves as the right hip strike plate surface. These surfaces 56A and 56B allow instrument 40 to be struck in a direction more closely aligned with the direction in which force needs to be transmitted for optimal effect on bone of the shaping member 42. In the version shown in FIGS. 6 and 7, the strike plate 46 is generally square in cross-section with a left bevel and a right bevel which correspond to the position of the shaping member 42 when it is connected to instrument 40 for operating on a left femur 18 or right femur 52 respectively.

Offset 48 in the particular instrument 40 shown in FIGS. 6 and 7 constitutes a member that extends from the distal portion of handle 44 in a direction that is angled from the direction in which handle 44 extends. The particular offset 48 shown in FIGS. 6 and 7 is a straight elongated structure with a tubular cross section and a longitudinal axis 58 aligned with the length of offset 48. A cross-section of offset 48 can be tubular, rectangular shaped, or any other desired shape and hollow, partially hollow, solid or as otherwise desired. The orientation of offset 48 is selected to cause handle 44 to be offset from shaping member 42 laterally and anteriorly with respect to the patient, whether instrument 40 is being used in connection with a left leg or a right leg. The nature and extent of such lateral and anterior offsets can be chosen as desired, but generally allow instrument 40 to provide sufficient control and leverage over shaping member 42 in order to shape the intramedullary canal of the femur efficiently and effectively, while avoiding the gut zone, musculature and/or other body portions of patients such as obese or highly muscled individuals. Instrument 40 may also allow clearance from other instrumentation placed on a patient, such as an array for use with a computer assisted surgery (CAS) system placed in the pelvic region. The length of offset 48, and its shape, angulation and other structural features can be selected as desired to provide the desired lateral and anterior offset. In the particular instrument 40 shown in FIGS. 6 and 7, offset 48 and its axis 58 are oriented at approximately 45 degrees to handle 44 and its axis 54. As noted above, in other embodiments which are not shown, the handle 44 and the offset 48 may be blended together to form an arc to reduce material use and provide better clearance from a patient's gut zone, musculature and/or other body portions.

The orientation of instrument 40 shown in FIG. 6 combined with its connection to shaping member 42 configures instrument 40 for preparation of an intramedullary canal of a left femur. Note that the offset 48 extends from shaping member 42 in a direction that includes lateral (x-axis) and anterior (y-axis) components to cause the handle 44 to be disposed generally parallel to, but offset laterally and anteriorly, from shaping member 42. In FIG. 7, the same instrument accepts shaping member 42 in another configuration to cause the handle 44 to be aligned generally parallel to shaping member 42 but offset laterally and anteriorly for purposes of preparing the intramedullary canal of a right femur. The shaping member 42 used for the right femur can be the same device as used for the left femur, or different devices can be used for each of the right and left femurs. For example, there can be a specially prepared shaping member 42 that corresponds to the right femur, and a specially prepared shaping member 42 that corresponds to the left femur.

Figure 8:
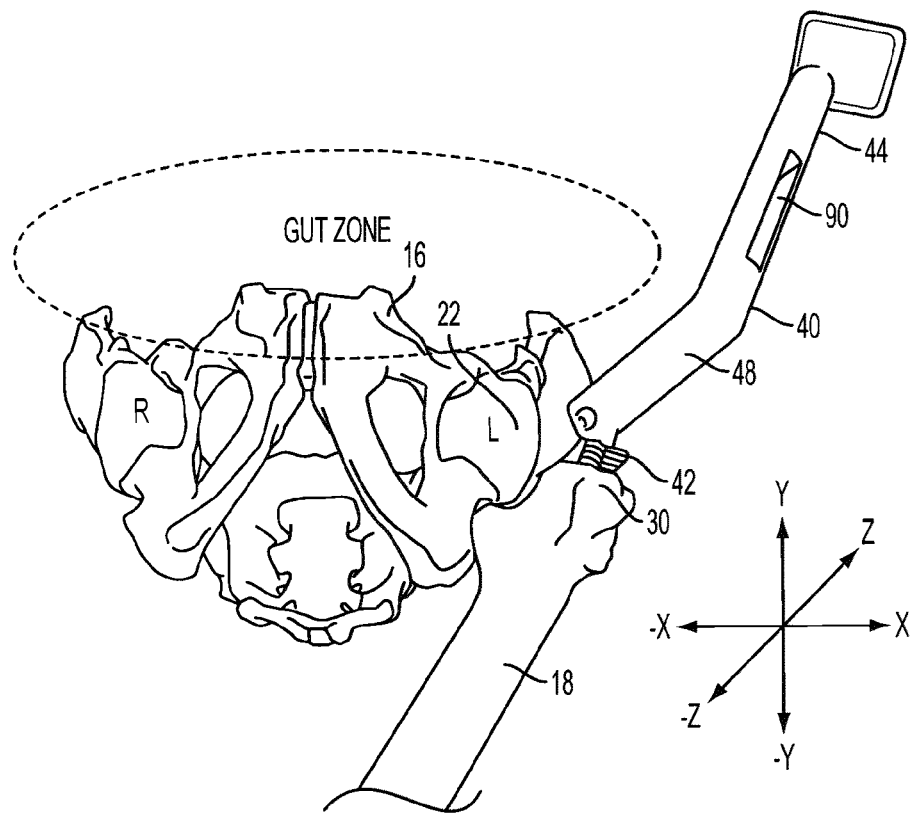
FIG. 8 shows the instrument assembly of FIG. 6 positioned for operating on the left femur.

FIG. 8 shows the instrument 40 as configured in FIG. 6 positioned to insert shaping member 42 into the intramedullary canal of the left femur 18. The offset 48 which offsets handle 40 laterally and anteriorly to the shaping member 42 can be seen to allow the handle 44 to avoid the gut zone of the patient when the instrument 40 is positioned and oriented for an anterior approach.

Figure 9:
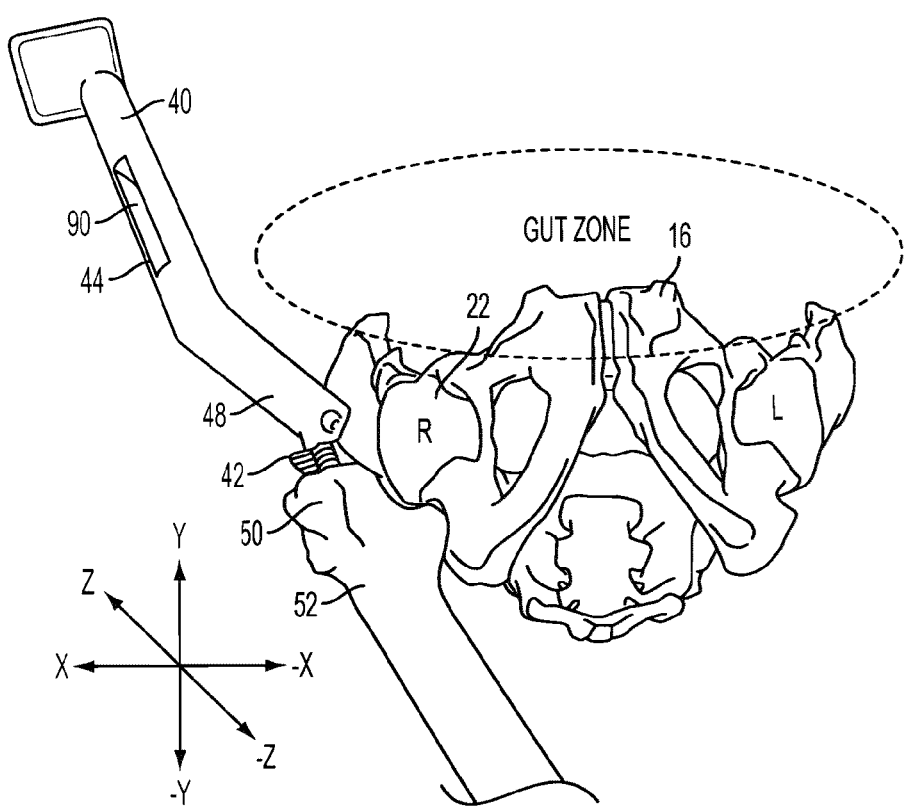
FIG. 9 shows the instrument assembly of FIG. 7 positioned for operating on the right femur.

FIG. 9 shows the instrument 40 as configured in FIG. 7 with the shaping member 42 inserted in the intramedullary canal 50 of right femur 52. The instrument 40 is the same device shown in FIG. 8, but the shaping member 42 has been connected to instrument 40 in a different way to allow the right femur 52 to be accommodated rather than the left femur 18. Once again, instrument 40 allows preparation of the intramedullary canal 50 with the benefit of the lateral and anterior offset of handle 44 relative to shaping member 42 provided by offset 48.

Figure 10:
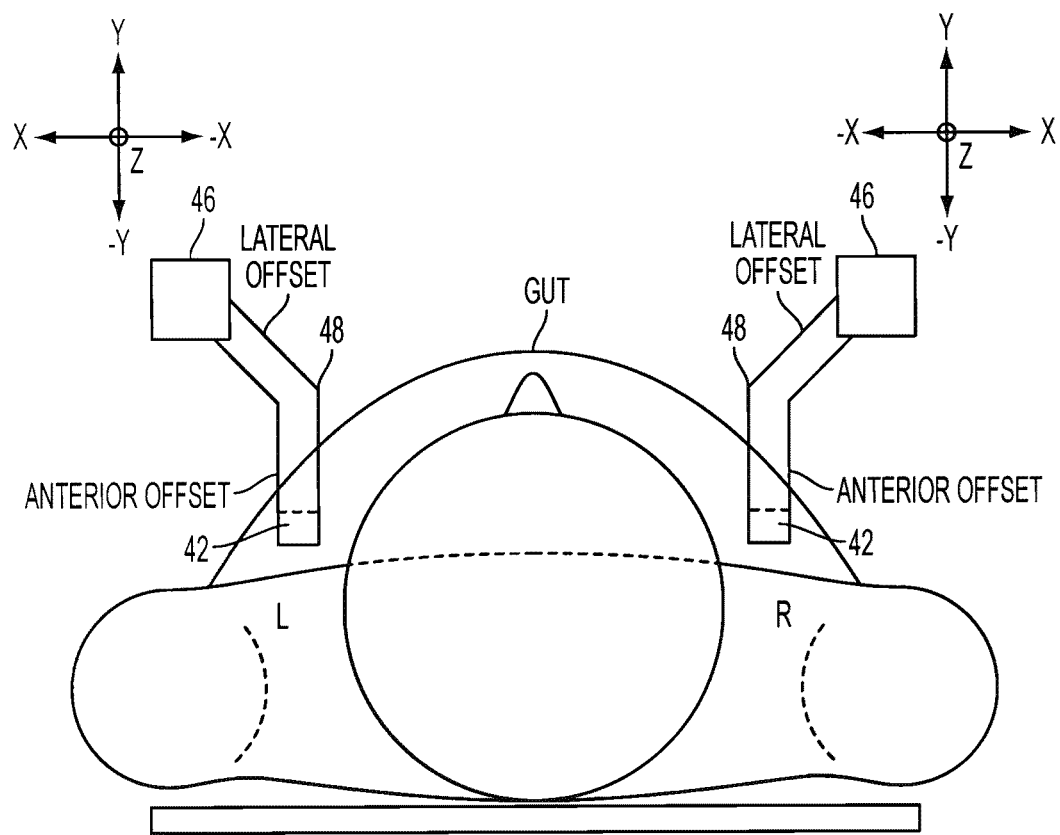
FIG. 10 schematically shows a superior view of the instrument of FIG. 6 positioned relative to a patient.

FIG. 10 is a schematic from a superior perspective that shows the anterior and lateral offset of a handle 44 relative to a shaping member 42 of an instrument 40, which can be accomplished using various structures in various ways according to various aspects of the invention so that the instrument 40 can accommodate either a left femur 18 or right femur 52.

Figure 11:
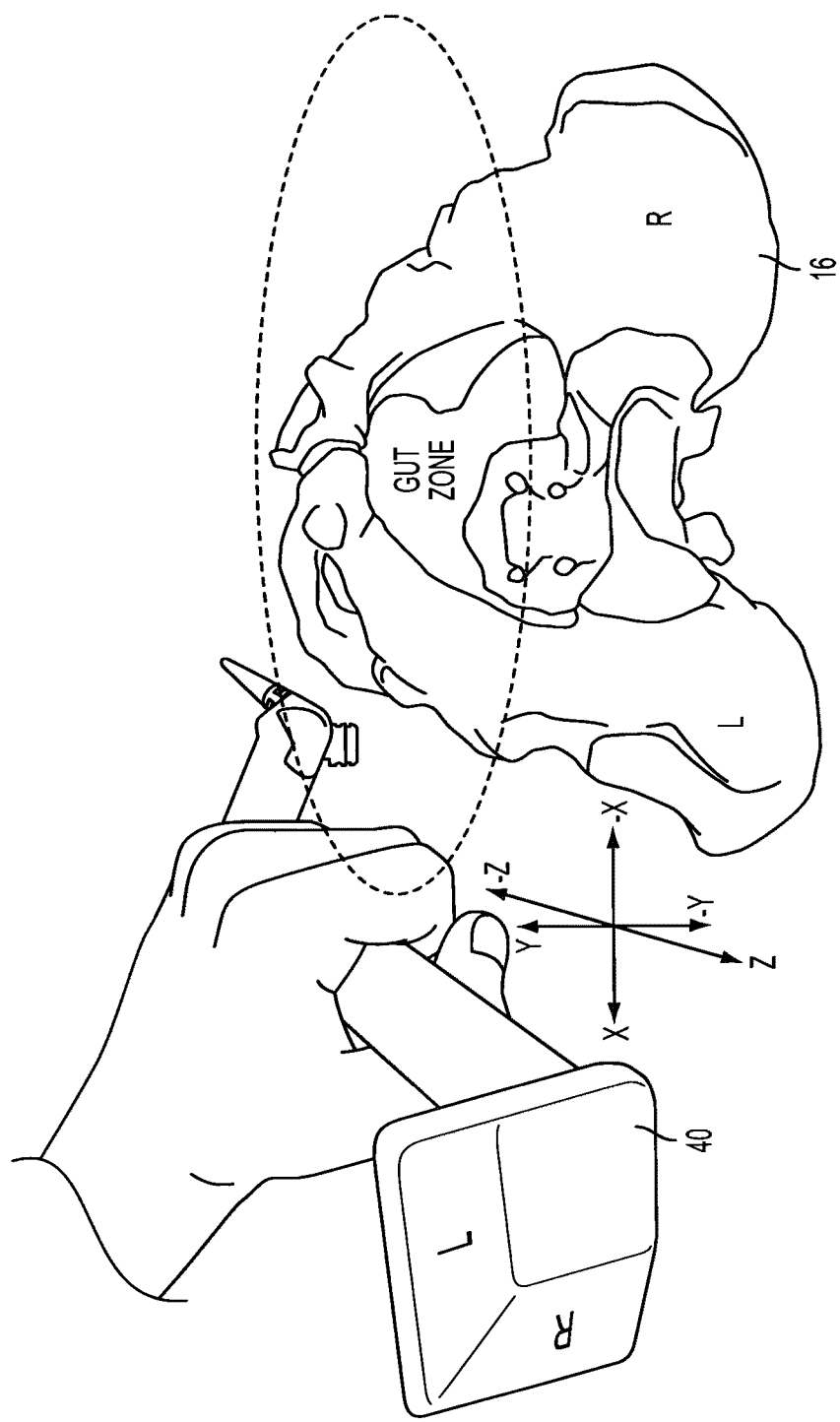
FIG. 11 shows a perspective view of the instrument assembly of FIG. 6 positioned relative to the pelvic cage and left acetabulum.
Figure 12:
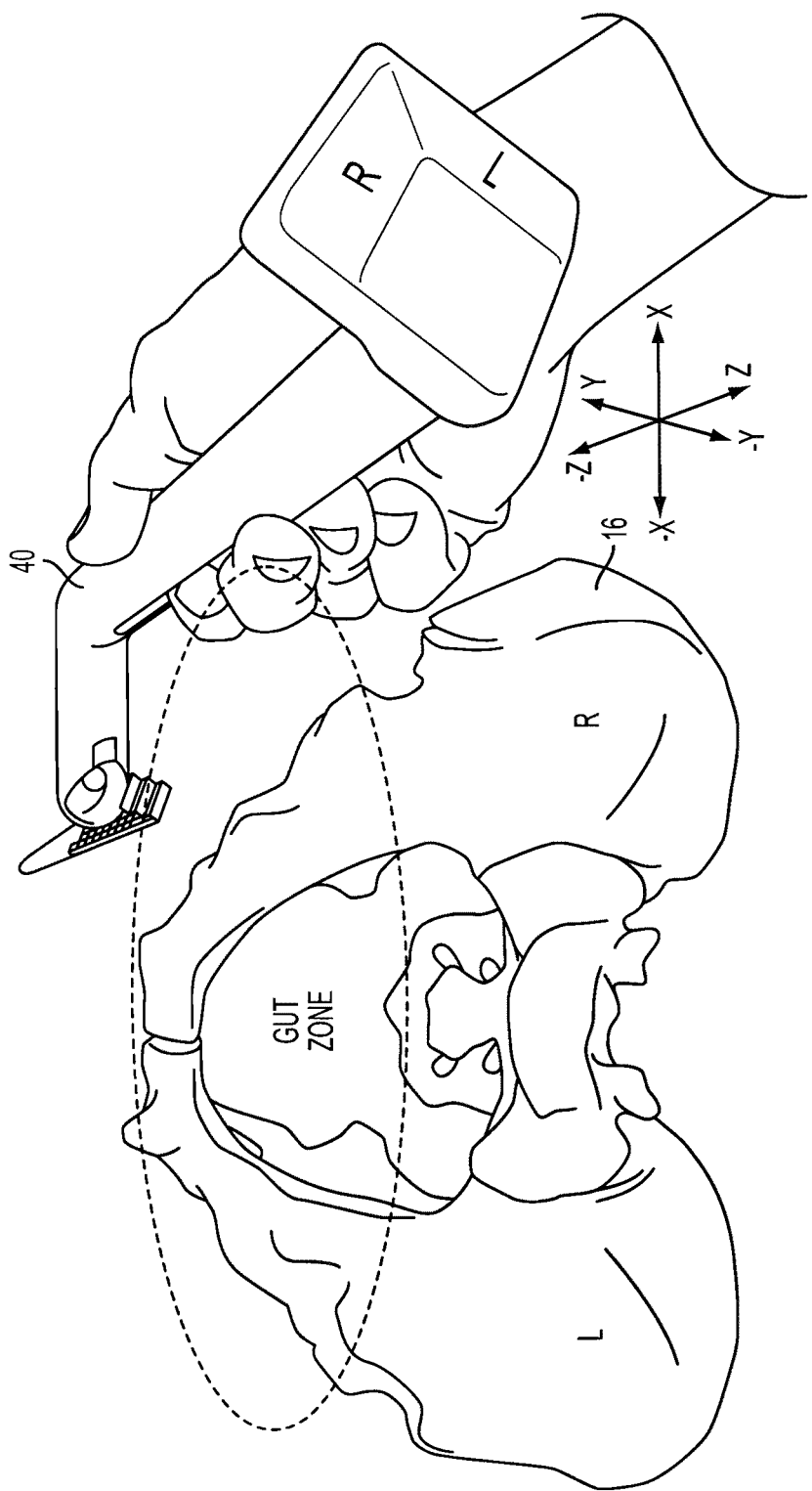
FIG. 12 shows a perspective view of the instrument assembly of FIG. 7 positioned relative to the pelvic cage and right acetabulum.

FIGS. 11 and 12 are perspective views of the pelvic cage 16 and the instrument 40 showing instrument 40 positioned in FIG. 11 to prepare the intramedullary canal of the left femur 18 and in FIG. 12 to prepare the intramedullary canal of the right femur 52. FIGS. 11 and 12 provide additional visual perception of how the offset of handle 44 relative to shaping member 42 provided by the particular structure of instrument 40 allows handle 44 to avoid the gut zone of the patient whether instrument 40 is configured for preparation of the intramedullary canal of the left femur 18 or the right femur 52.

FIGS. 11 and 12 are useful to characterize, among other things, aspects of the structure and geometry of the instrument 40 shown in those figures as well as broader aspects of the structure and geometry of instruments according to certain embodiments of the invention more generally. Instrument 40 shown in FIG. 11 is the same instrument as instrument 40 shown in FIG. 12, but in FIG. 11 it is configured for operation on the left femur 18 while in FIG. 12 it is configured for operation on the right femur 52.

In FIG. 11, instrument 40 includes a handle 44 which is aligned with Z axis 28 and extends distally in the negative Z direction. Since the instrument 40 is generally aligned with the patient's anatomy in that illustration, the handle 44 also extends distally in the inferior direction of the patient's anatomy. If, however, the instrument 40 is removed from the vicinity of the patient, or reoriented substantially, handle 44 would in any event for purposes of this document extend distally in the negative Z direction since the X, Y, Z coordinate system corresponds to the instrument 40 independent of how the instrument 40 is aligned relative to the patient in the frontal, sagittal and coronal planes. Connected to a distal portion of handle 44 is an offset 48, which extends from handle 44 toward shaping member 42 in a direction that contains a negative X directional component and a negative y directional component. Since the instrument 40 as shown in FIG. 11 is generally aligned with the patient's anatomy and is configured for operation on the left femur 18, the offset 48 also extends in a direction that includes a medial component and a posterior directional component relative to the patient's anatomy; again, if the instrument 40 is removed from the vicinity of the patient, or reoriented substantially, the offset 48 would in any event for purposes of this document extend in a direction that contains a negative X directional component and a negative y directional component, regardless of the fact that those components no longer correspond to the medial and posterior directions of the patient's anatomy. It should be noted that the ratio of lateral to anterior offset of the handle 44 (or handle axis 54) with respect to the shaping member 42 (or shaping member axis 68) may vary between greater than zero and infinity, however, it is preferred that said ratio lies within the range of 0.5-1.5, and more preferably, about 1.

In FIG. 12, as in FIG. 11, the handle 44 is aligned with Z axis 28 and extends distally in the negative Z direction. Since the instrument 40 is generally aligned with the patient's anatomy in that illustration, the handle 44 also extends distally in the inferior direction of the patient's anatomy. Again, however, if the instrument 40 is removed from the vicinity of the patient, or reoriented substantially, handle 44 would in any event for purposes of this document extend distally in the negative Z direction since the X, Y, Z coordinate system corresponds to the instrument 40 independent of how the instrument 40 is aligned relative to the patient in the frontal, sagittal and coronal planes of the patient's anatomy. Unlike FIG. 11, however, FIG. 12 shows the instrument 40 configured to operate on the right femur 52. Accordingly, connected to a distal portion of handle 44 is offset 48, which extends from handle 44 toward shaping member 42 in a direction that contains a negative X directional component and a negative Y directional component. Since the instrument 40 as shown in FIG. 12 is generally aligned with the patient's anatomy and is configured for operation on the right femur 52, the offset 48 also extends in a direction that includes a medial component and a posterior directional component relative to the patient's anatomy; again, if the instrument 40 is removed from the vicinity of the patient, or reoriented substantially, offset would in any event for purposes of this document extend in a direction that contains a negative X directional component and a negative Y directional component, regardless of the fact that those components no longer correspond to the medial and posterior directions of the patient's anatomy. Among other things, the direction in which offset 48 extends from handle 44 in FIG. 12 includes a negative X directional component that corresponds to the patient's medial direction. Similarly, the direction in which offset 48 extends from handle 44 in FIG. 11 includes a negative X directional component that corresponds to the patient's medial direction. In the particular instrument 40 shown in FIGS. 11 and 12, the change of direction in which offset 48 extends from handle 44 is accomplished by connecting shaping member 42 to offset 48 in a different location on offset 48 and at a different orientation relative to offset 48 in FIG. 11 as compared to FIG. 12, and also rotating handle 44 so that the offset 48 extends, in both cases, medially and posteriorly from the handle 44 (laterally and anteriorly from the shaping member 42) when the instrument 40 is generally aligned with the patient's anatomy to operate on either the left femur 18 or right femur 52.

Figure 13:
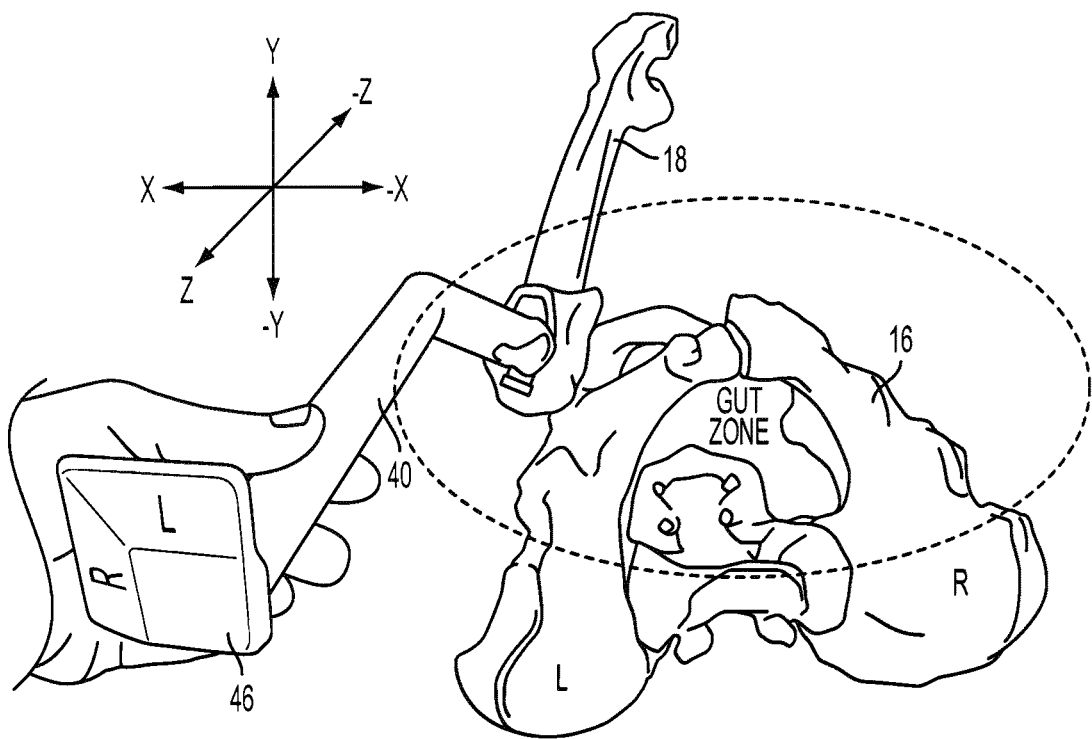
FIG. 13 shows the instrument assembly of FIG. 6 positioned relative to the pelvic cage and left femur, in order to illustrate how the offsets provided by the instrument avoid interference from the gut zone while accessing the left femoral intramedullary canal.
Figure 14:
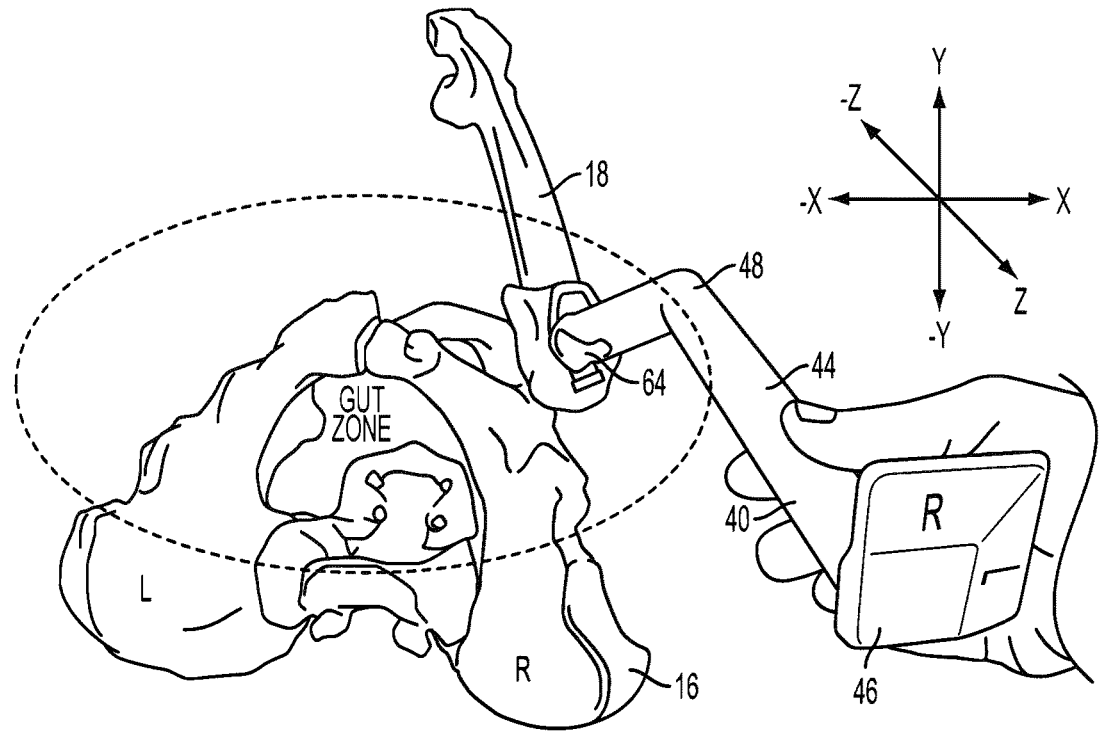
FIG. 14 shows the instrument assembly of FIG. 7 positioned relative to the pelvic cage and right femur, in order to illustrate how the offsets provided by the instrument avoid interference from the gut zone while accessing the right femoral intramedullary canal.

FIGS. 13 and 14 are views similar to FIGS. 11 and 12, but with the femurs 18 and 52 themselves in the field of view to show more clearly how positioning and orientation of the shaping member 42 corresponds to the intramedullary canal 30 of left femur 18 (FIG. 13) or the intramedullary canal 50 of right femur 52 (FIG. 14).

Figure 15:
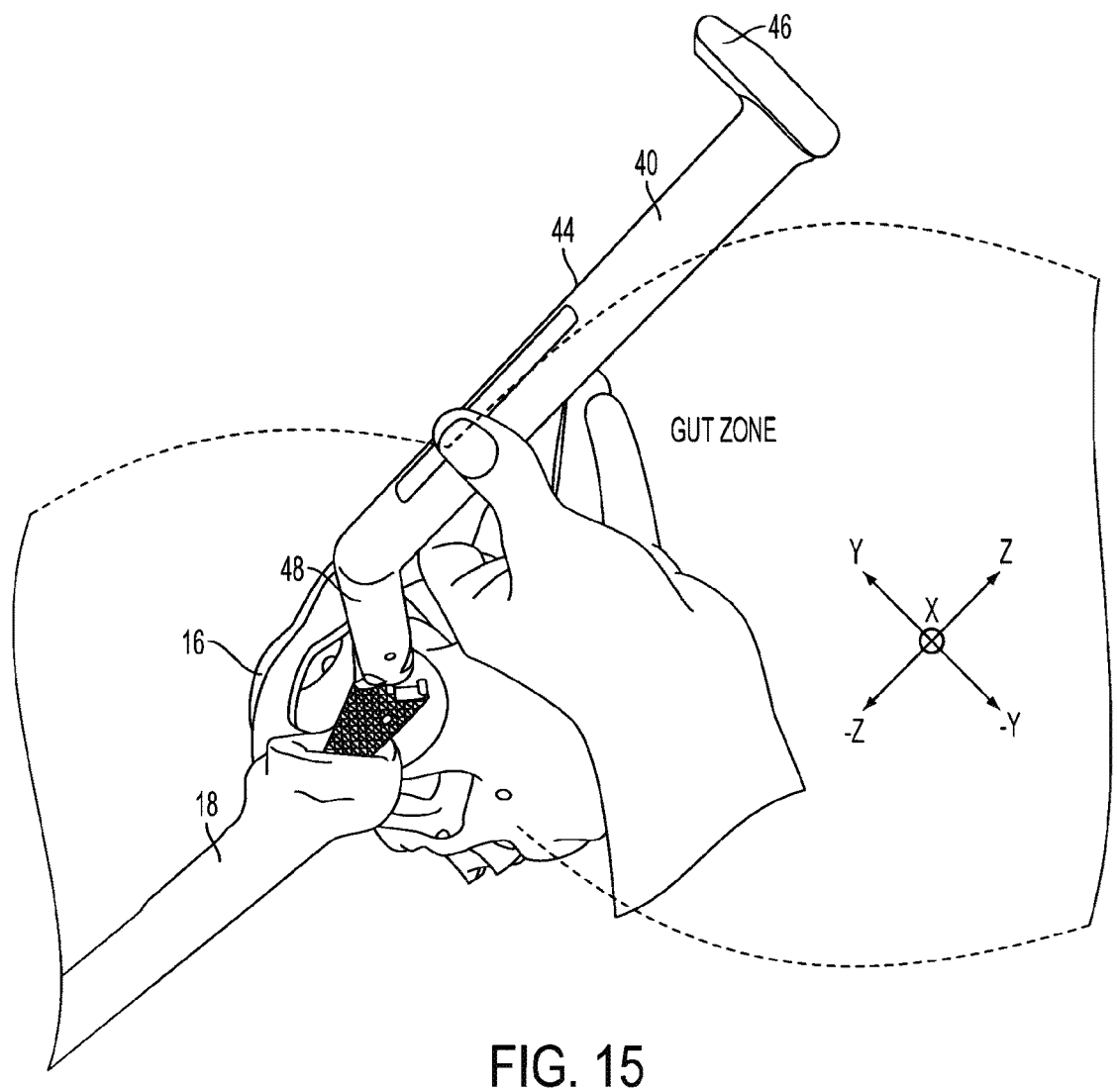
FIG. 15 shows a lateral perspective view of the instrument assembly of FIG. 6 positioned relative to the left femur and the gut zone in a sagittal plane.

FIG. 15 is a sagittal view of instrument 40 positioned for preparation of the intramedullary canal 30 of left femur 18. This figure provides additional visual perspective on how the offset of handle 44 relative to shaping member 42 helps avoid the gut zone of the patient. In that sense, offset 48 offsets handle 44 from shaping member 42, or vice versa.

Figure 16:
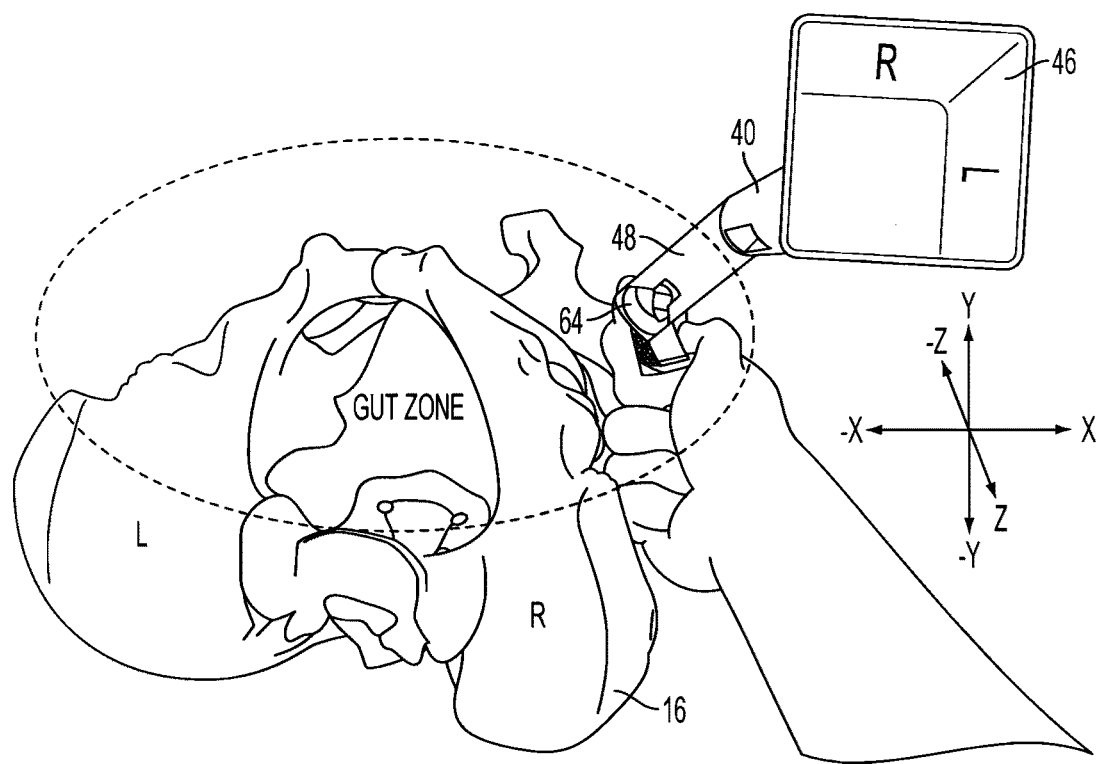
FIG. 16 shows the instrument assembly of FIG. 7 positioned relative to the pelvic cage and the right femur in order to demonstrate how leverage can be applied to the bone shaping member of the instrument in order to prepare the intramedullary canal of the right femur without undue interference by the gut zone.
Figures 17, 18:
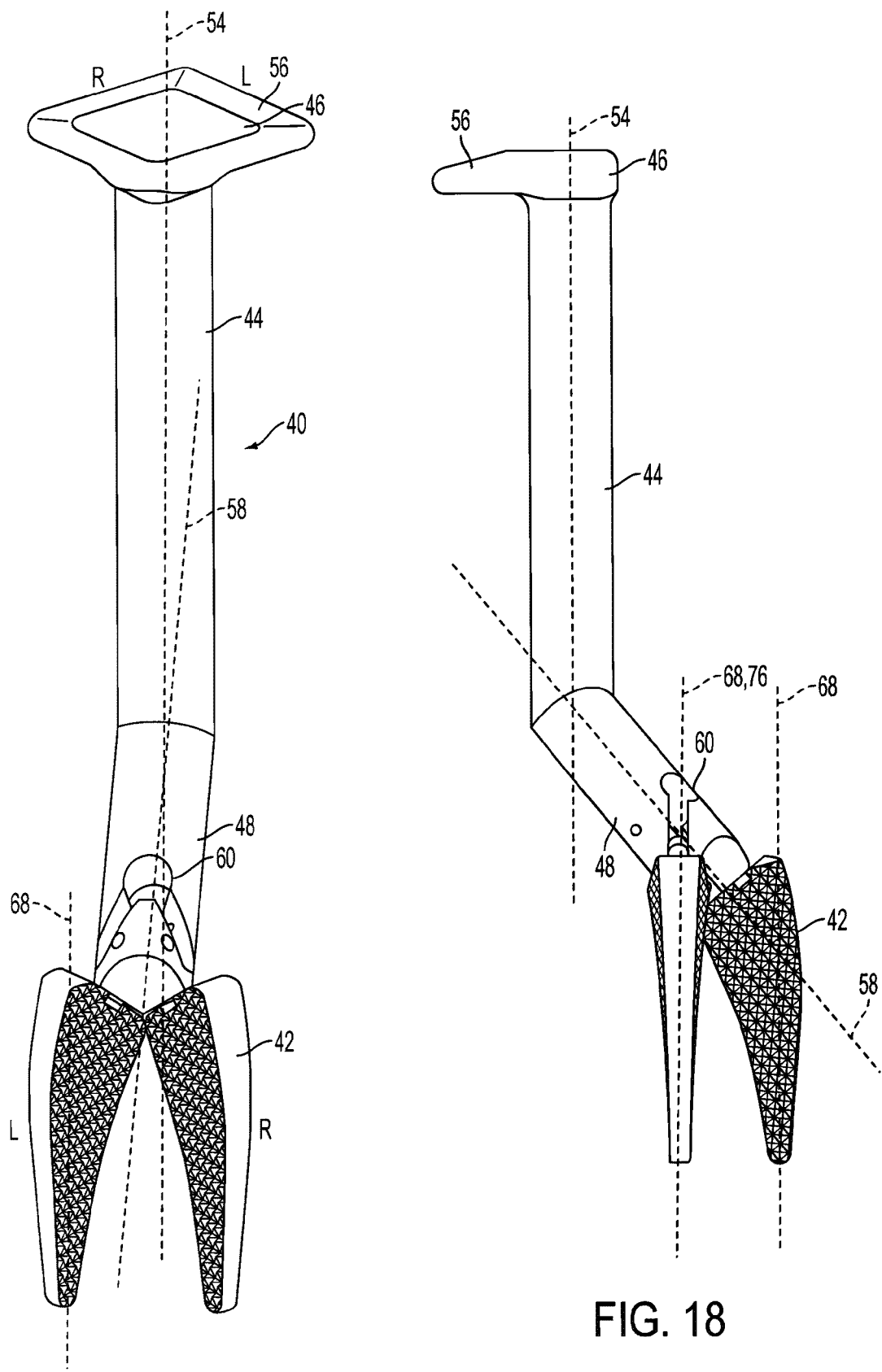
FIG. 17 is a perspective view of an instrument according to some embodiments of the invention simultaneously showing a bone shaping member superimposed on the instrument in two different configurations (for operating on a left and right femur).
FIG. 18 shows another perspective view of the instrument and superimposed bone shaping member configurations of FIG. 17.

FIG. 16 is a generally transverse superior perspective view that provides additional visual perspective on how the offset of handle 44 relative to shaping member 42 of instrument 40 helps avoid the gut zone when instrument 40 is configured for preparing the intramedullary canal of a right femur 52.

As disclosed in this document, the invention includes multiple structures and embodiments for achieving the lateral and anterior offset of handle 44 relative to shaping member 42 (medial and posterior offset of shaping member 42 relative to handle 44) in a single instrument 40 that can accommodate the intramedullary canal of both a left femur and a right femur. Instrument 40 as shown in FIGS. 6-9 and 11-16, for example, includes a single structural offset 48 which extends from handle 44 along a generally linear longitudinal axis that is oriented in a direction that contains a negative Y directional component and a negative X directional component when configured for the left or the right leg, in order to provide the lateral and anterior offset of handle 44 from shaping member 42. However, the invention contemplates any structure which connects a handle 44 and a shaping member 42 where the instrument 40 can be configured to provide a lateral and anterior offset of the handle relative to the shaping member for each of the left femur 18 and right femur 52 in order to prepare the intramedullary canal 30 of a left femur 18 or a right femur 52. Such structures can include, for instance, any physical structure that provides lateral and anterior directional components or offsets from shaping member 42 to handle 44 and/or strike plate surface or surfaces 56, or conversely, medial and posterior offsets or directional components when proceeding from handle 44 and/or strike plate surface or surfaces 56 to shaping member 42.

Instrument 40 is more clearly shown in FIGS. 17-26. In the instrument 40 shown in FIGS. 17-26, offset 48 includes or connects to a handle connecting structure 60, located at the distal portion of offset 48. Handle connecting structure 60 generally includes an opening or other structure for receiving or accommodating connecting structure of a shaping member 42, in addition to a structure accommodating linkage that is configured to lock or retain shaping member 42 in place. While not shown, the handle connecting structure 60 may be separable from offset 48, or may comprise separate adapters or elements to accommodate various types of shaping members 42.

Figure 19:
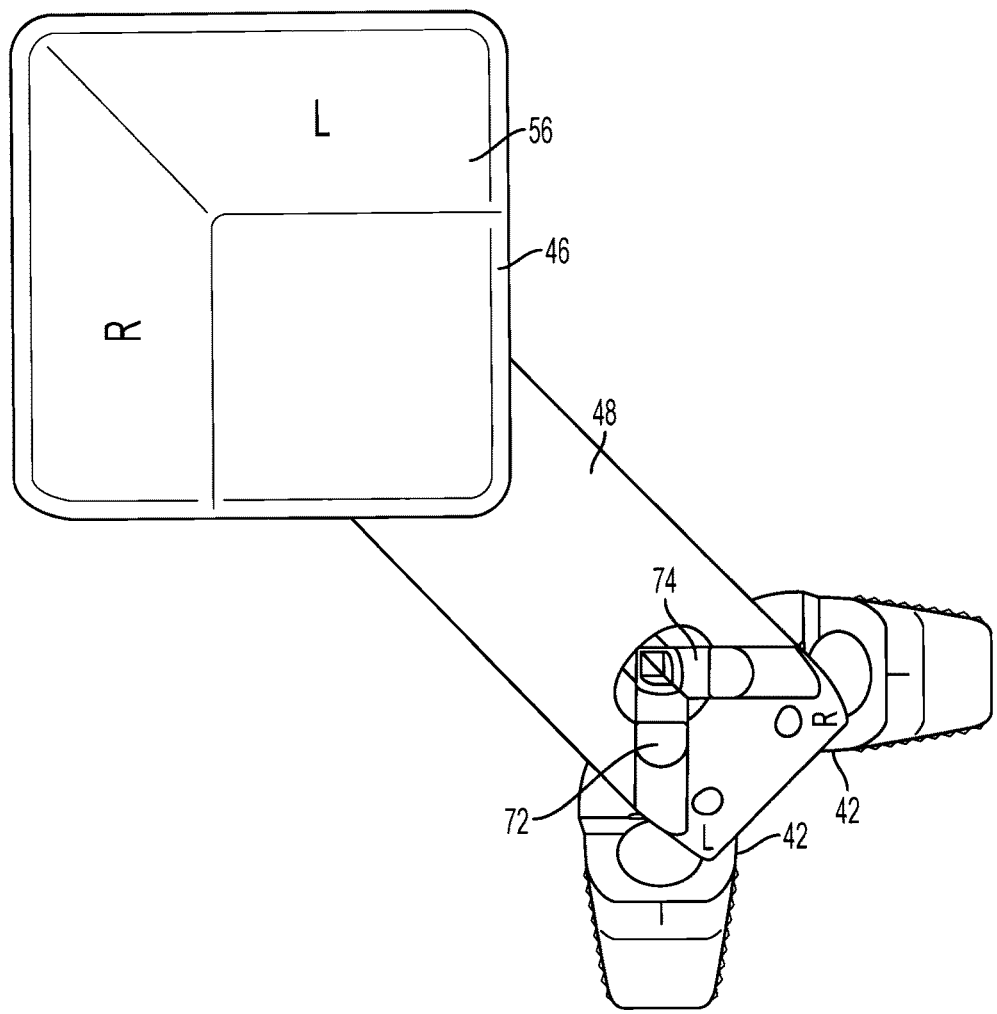
FIG. 19 shows an elevated perspective view of the instrument and superimposed bone shaping member configurations of FIG. 17.
Figure 25:
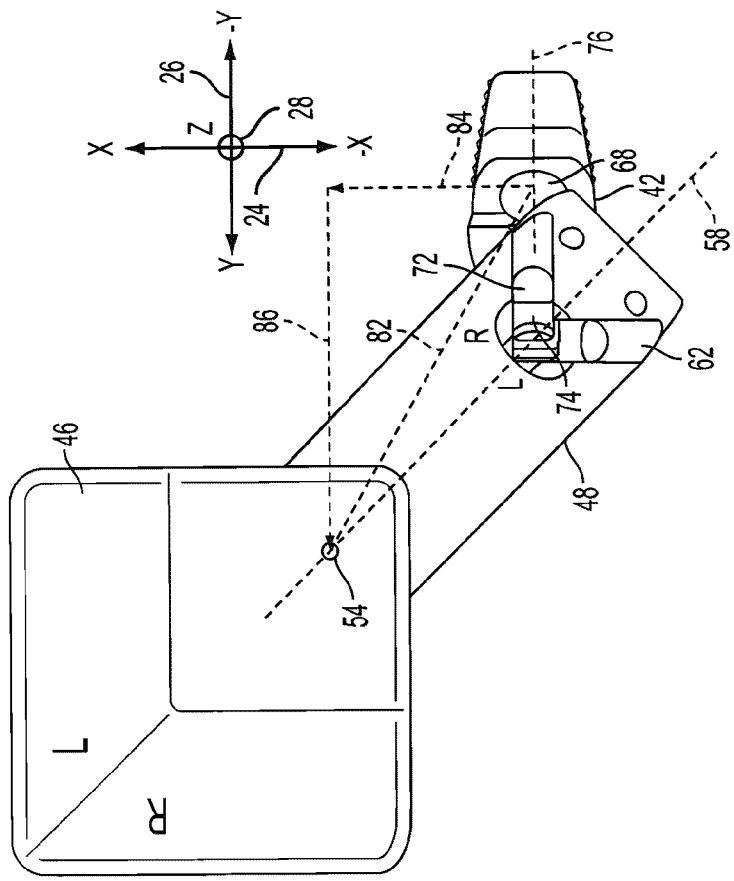
FIG. 25 shows an elevated perspective view of the instrument assembly of FIG. 23.

In the instrument 40 of the embodiment shown in FIGS. 17-26, instrument connection structure 60 includes a pair of shaping member reception openings 62 and space 64 for accommodating a retention linkage 66. Reception openings 62 are configured in shape and dimension to correspond to connection structures such as projections on shaping members 42, in order to hold and orient such structures to position and orient shaping members 42 relative to offset 48 and handle 44 appropriately. In that vein, openings 62 are oriented in a direction that generally aligns the longitudinal axis 68 of shaping member 42 to be generally parallel with the longitudinal axis 54 of handle 44. In some embodiments, only a single opening 62 may be provided at a distal portion of offset 48, in which the longitudinal axis 68 of shaping member 42 is not generally aligned to be parallel with the longitudinal axis 54 of handle 44. The longitudinal axis 68 of shaping member 42 is generally the axis that extends through shaping member 42 in a direction that corresponds to the direction of the intramedullary canal in patients for whom the shaping member 42 is intended. Reception openings 62 and/or linkage accommodation space 64 also allow linkage 66 to be situated relative to offset 48 so that the linkage 66 can be actuated in order to interpose an interposition structure 70 such as a pawl, claw or other structure into an interposition cooperation structure or retaining recess 72 on shaping member 42 in order to retain shaping member 42 in position and proper orientation relative to instrument 40. Reception openings 62 are perhaps best seen in FIGS. 21, 24 and 26 from an exterior aspect and FIGS. 19, 22 and 25 from a superior aspect. Linkage accommodation 64 can be seen in all of these figures. Interposition structure cooperation structure or retaining recess 72 on shaping member 42 is perhaps best seen in FIGS. 19, 22, and 25. There, shaping member 42 is shown to have a post 74 connection structure with an interposition structure cooperation structure 72. In some embodiments, a free end portion of the post 74 may have one or more second interposition cooperation structures (e.g., a transversely extending slot) for engaging one or more second interposition structures (e.g., a transversely extending pin) located within the instrument 40, in order to facilitate the orientation of the shaping member 42 relative to the instrument 40, and to allow orienting of the shaping member 42 relative to the instrument 40 to be performed independently of a locking function provided by the interposition and interposition cooperation structures. The post 74 is received in a reception opening 62 of instrument 40, and the retaining recess 72, here a notch, is situated on post 74 of shaping member 42 to cause shaping member 42 to be oriented so that reference plane 76, such as a plane of symmetry, of shaping member 42 is generally aligned in a direction such that as the longitudinal axis 68 of shaping member 42 is aligned with the longitudinal axis 54 of the handle 44, the reference plane 76 of the shaping member 42 can be considered to define a direction from which offset 48 provides appropriate lateral and anterior offset to the handle 44 from the longitudinal axis 68 of shaping member 42. As can be seen in FIGS. 19, 22 and 25, the reference plane 76 of shaping member 42 is, in the instrument 40 of the embodiment shown in those figures, generally aligned with the strike direction 78 of beveled surfaces 56 of strike plate 46. As shown in FIGS. 19, 22 and 25, position and orientation of openings 62 are preferably symmetrical in the superior aspect about longitudinal axis 58 of offset 48. In that aspect, each opening 62 is angulated from that axis 58 at approximately 45 degrees, although other angulation magnitudes and/or directions can be employed, depending on a number of factors including offset of handle 44 from shaping member 42, angulation and position of strike plate 46 and its beveled surfaces 56, or if no strike plate is used, structure and configuration of a proximal end or other appropriate structure on handle 44.

Figure 24:
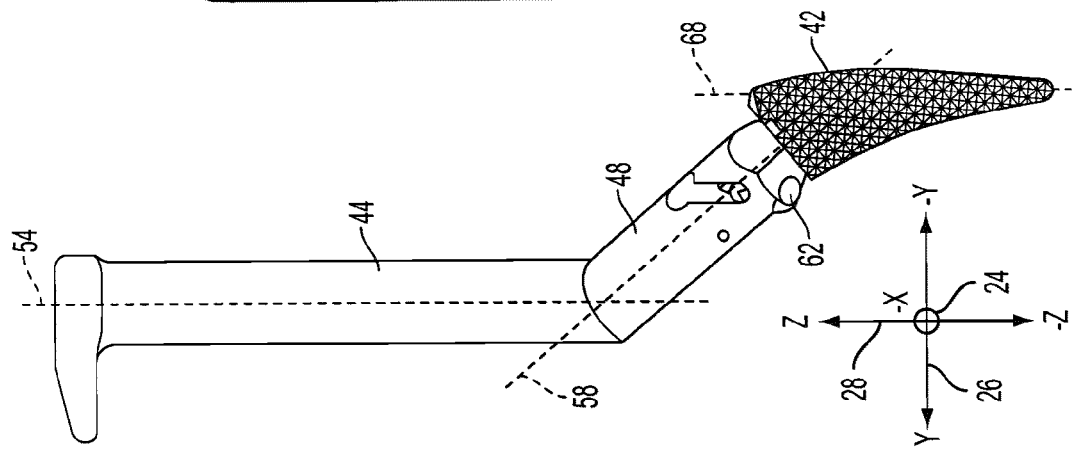
FIG. 24 shows a medial perspective view of the instrument assembly of FIG. 23.
Figure 23:
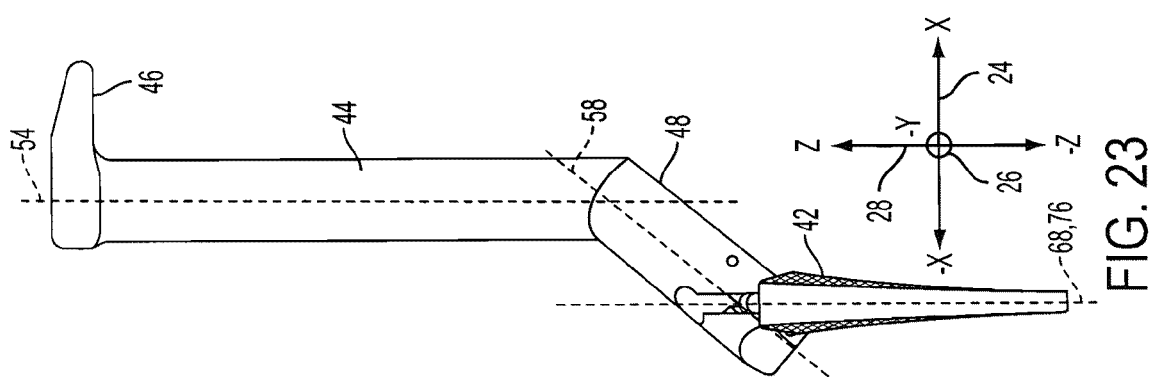
FIG. 23 shows a posterior perspective view of the instrument assembly of FIG. 7.

FIGS. 20-22 show instrument 40 configured for surgery on a left femur 18, while FIGS. 23-25 show instrument 40 configured for surgery on a right femur 52. FIG. 20 shows instrument 40 oriented so that reference plane 76, such as a plane of symmetry of shaping member 42 is orthogonal to the printed page. That axis thus appears as a line on FIG. 20. FIG. 20 thus shows instrument 20 as would be seen from a posterior aspect of a patient whose left femur is being operated on. In that sense, offset 48 proceeds laterally from shaping member 42 and anteriorly, or "into the page" from shaping member 42 to form the offset magnitude and direction from which the handle 44 is offset from the shaping member 42. Thus, offset 48 as shown in FIG. 20 proceeds from shaping member 42 in a direction that includes an X directional component or lateral directional component, and a positive Y directional component or anterior directional component, to form the offset of longitudinal axis 54 of handle 44 (or of handle 44 itself) relative to the longitudinal axis 68 of shaping member 42 (or to shaping member 42). Offset 48 also includes a Z or superior directional component as it extends from shaping member 42 to handle 44, so that ultimately the direction of longitudinal axis 58 of offset 48 shown in FIG. 20 is a resultant or function of these X, Y, Z directional components.

FIG. 21 shows the instrument 40 configured for surgery on the left femur 18 in the sagittal plane from a medial aspect. There, offset 48 can be seen to be extend from shaping member 42 to handle 44 in a direction that includes a lateral or X directional component, an anterior or Y directional component, and a superior or Z directional component to form the offset between shaping member 42 and handle 44; the magnitude and direction of these directional components create the resultant that corresponds to the direction of the offset geometry 82 of the handle 44 longitudinal axis 54, or the handle 44 itself, relative to the shaping member 42 longitudinal axis 68, or to the shaping member 42 itself. In the transverse plane as shown in FIG. 22, offset geometry 82 can be seen to be a function of the positive X or lateral directional component 84 and the Y or anterior directional component 86.

FIGS. 23-25 show instrument 40 configured for operation on a right femur 52 using the same shaping member 42 as shown in FIGS. 20-22, but with the shaping member 42 inserted in the other reception opening 62 of instrument 40 that corresponds to the right femur 52. FIG. 23 shows instrument 40 in a coronal plane, from a posterior aspect. Accordingly, offset 48 proceeds laterally and anteriorly from shaping member 42 to handle 44. Thus, when instrument 40 has been configured to shape a right femur 52 intramedullary canal, the offset from the shaping member 42 longitudinal axis 68 to handle 44 longitudinal axis 54 as seen in a transverse plane (FIG. 25) is formed by the magnitude and direction of the positive X or lateral directional component 84 and the anterior or positive Y directional component 86.

FIG. 24 is a sagittal view of the instrument 40 configured for shaping the right femur 52 intramedullary canal, from a medial aspect. Comparing FIG. 22, which shows instrument 40 in a transverse plane configured for surgery on a left femur 18 to FIG. 25, which shows the instrument 40 in a transverse plane configured for surgery on the right femur 52, the orientation of offset structure 48, shaping member 42, and offset geometry 82 can be seen to be a mirror image about longitudinal axis 58 of offset structure 48 when instrument 40 is configured for surgery on the left femur 18 as opposed to when it is configured for surgery on the right femur 52. In FIGS. 22 and 25, the angulation between reference plane 76 of shaping member 42 when instrument 40 is configured for surgery on the left femur 18 is 90 degrees from the orientation of reference plane 76 of shaping member 42 when the instrument 40 is configured for surgery on the right femur 52. However, such perpendicularity is not required; rather, the divergence angle 88 that reference plane 76 of shaping member 42 forms relative to longitudinal axis 58 of offset 48 is a function of, among other things, the structure of shaping member 42, the position and orientation of connecting structure 74 of shaping member 42, the position and orientation of openings 62, the structure, positioning and orientation of offset 48, and the desired distance and directional relationships between longitudinal axis 68 of shaping member 42 and longitudinal axis 54 of handle 44 to form offset geometry 82. As in the case of instrument 40 shown in FIGS. 6 and 7, offset 48 could be modular, adjustable, curved, contain multiple segments, some or all of which are not parallel to each other, or be shaped in any manner desired, with any desired cross section, to create directional components 84 and 86 in order to form the offset geometry 82. Considerations to be taken into account in that respect include materials, desired geometry, amount of offset needed for clearance of the gut zone, manufacturability, cost, and particular reamers, broaches, osteotomes, impaction grafting devices, or other shaping members 42, with which instrument 40 will be used.

Figure 26:
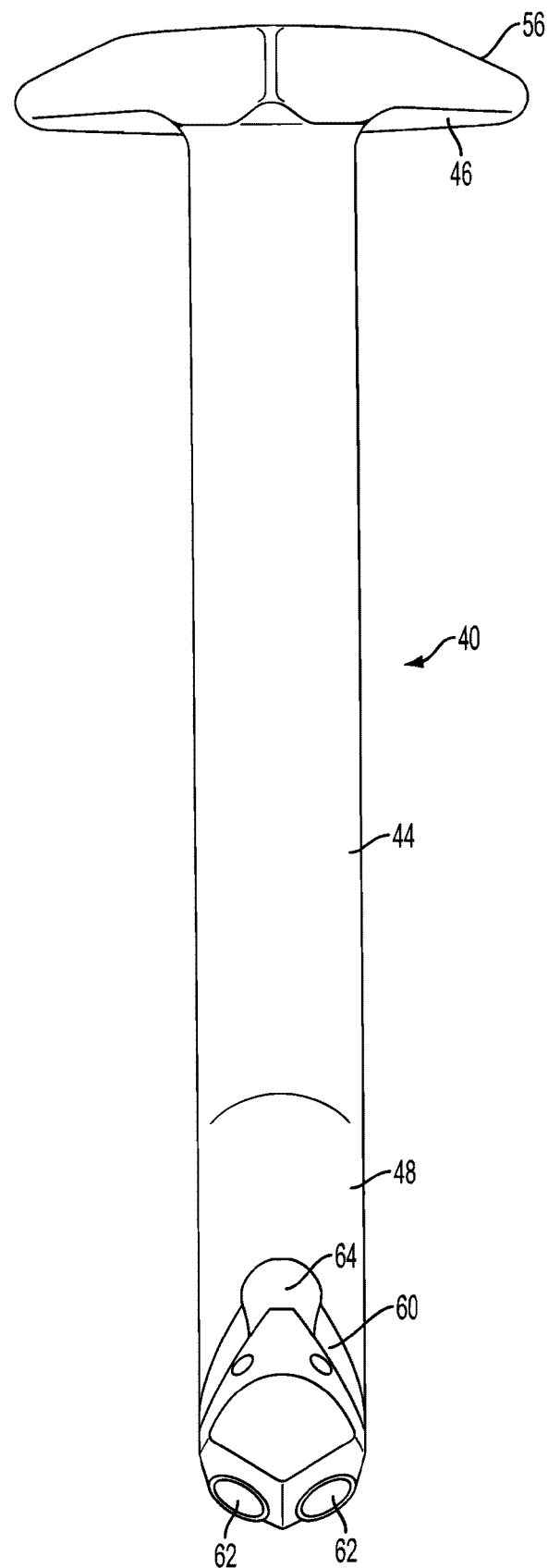
FIG. 26 shows a frontal view of the instrument shown in FIGS. 6-9 and 11-25.
Figure 27:
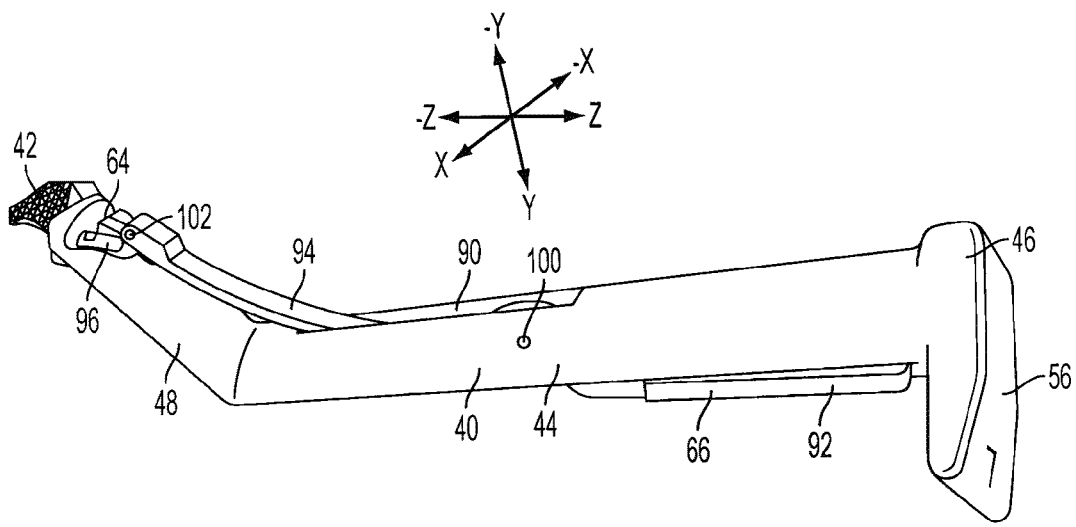
FIG. 27 shows a lateral perspective view of the instrument assembly of FIG. 6 in order better to illustrate a locking linkage structure positioned to lock the shaping member.
Figure 28:
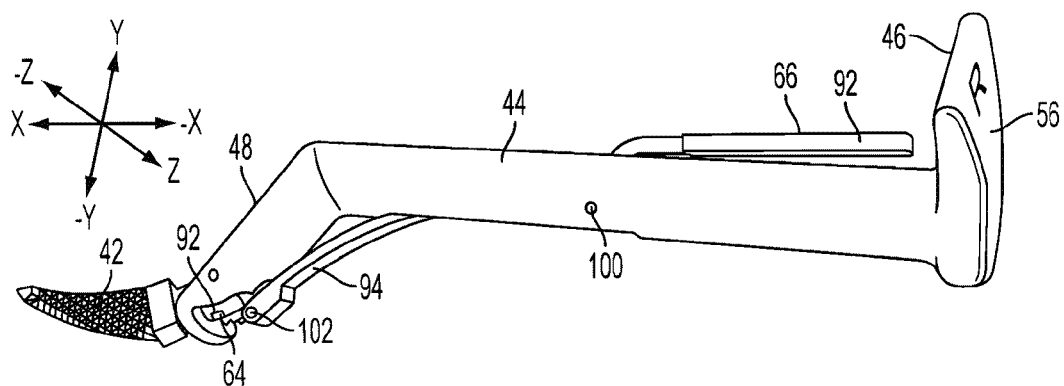
FIG. 28 shows another lateral perspective view of the instrument assembly of FIG. 27.
Figure 29:
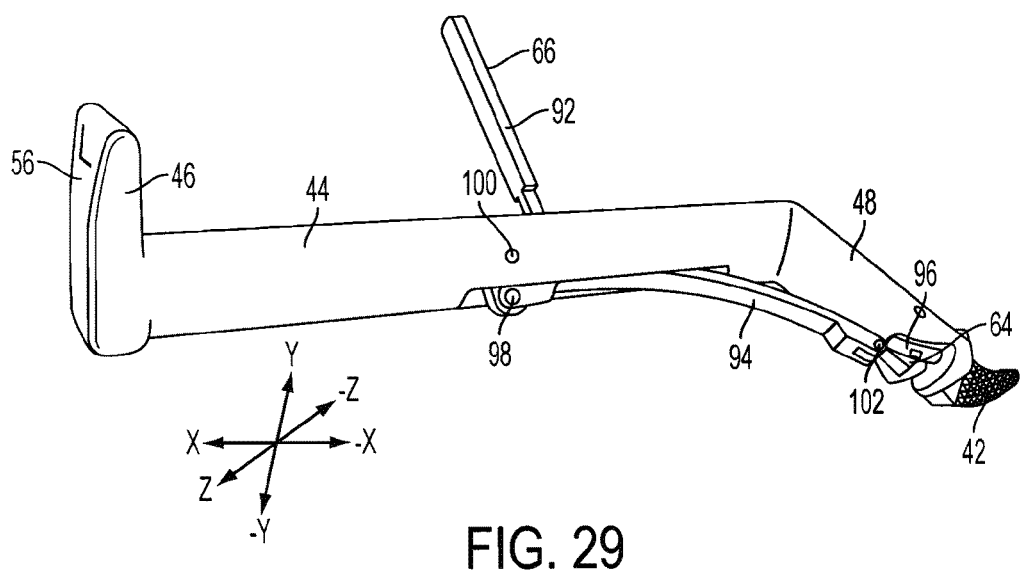
FIG. 29 shows a medial perspective view of the instrument assembly of FIG. 27 with the linkage positioned to unlock the bone shaping member.

FIG. 26 shows a frontal view of instrument 40 without shaping members 42 for better illustration of instrument connection structure 60 that includes reception openings 62 and linkage accommodation 64.

FIGS. 27-32 show instrument 40 of the first embodiment (see FIGS. 6-9 and 11-16) with linkage 66 for retaining shaping member 42 in instrument 40. The primary difference in the structure of instrument 40 shown in these figures from the instrument 40 shown in FIGS. 17-26 is the linkage accommodation structure 64 and other structure for accommodating linkage 66. The instrument 40 of FIGS. 6-9 and 11-16 includes a slot 90 in the handle, and the linkage accommodation 64 is a larger cavity than in instrument 40 of the second embodiment as shown in FIGS. 17-26. The slot 90 of the particular structure shown in FIGS. 27-32 extends through the handle 44 to receive in pivoting relationship an actuator lever 92 which can be rotated toward the handle 44 to engage interposition structure 70 of linkage 66 relative to interposition cooperation structure 72 on posts or other structures 74 of shaping member 42. A link 94, which may be configured as a leaf spring, connects the distal end of lever 92 to interposition structure 70 in the form of a claw, pawl or similar physical interference structure which is mounted in linkage accommodation 64 to pivot relative to offset 48. When actuator lever 92 is rotated away from handle 44, link 94 is pulled proximately (Z direction) and releases a spring force to pivot interposition structure 70 and thus withdraw it from the position in which it would be interposed in interposition structure cooperation structure 72 of the shaping member 42. When lever 92 is rotated into position against handle 44, the connection 98 and geometry of lever 92 distal end relative to link 94 rotates that connection 98 beyond top dead center of the lever-to-handle connection 100 (defined here relative to link-to-interposition structure connection 102) so that force on interposition structure 70 tending to disengage interposition structure 70 from shaping member 42 tends to urge actuator lever 92 against handle 44. Such structure is known as an "over center configuration." Other self-locking structures could be used such as, among others, camming mechanisms, worm/thread mechanisms, rack and pinion mechanisms, ratcheting devices, sliding collars, latching devices, or alternatively no self-locking or self-retaining structure is required for holding interposition structure 70 in place relative to interposition structure cooperation structure 70 to shaping member 42. Other mechanisms may be used as interposition structures 70, such as, for instance, set screws, wedges, pins, or other mechanical means that can be interposed relative to instrument 40 and shaping member 42 to hold shaping member 42 in place relative to instrument 40. If linkage 66 is used, it need not extend to handle 44, for example, the linkage may be contained on only offset portion 48.

Figures 30, 31:
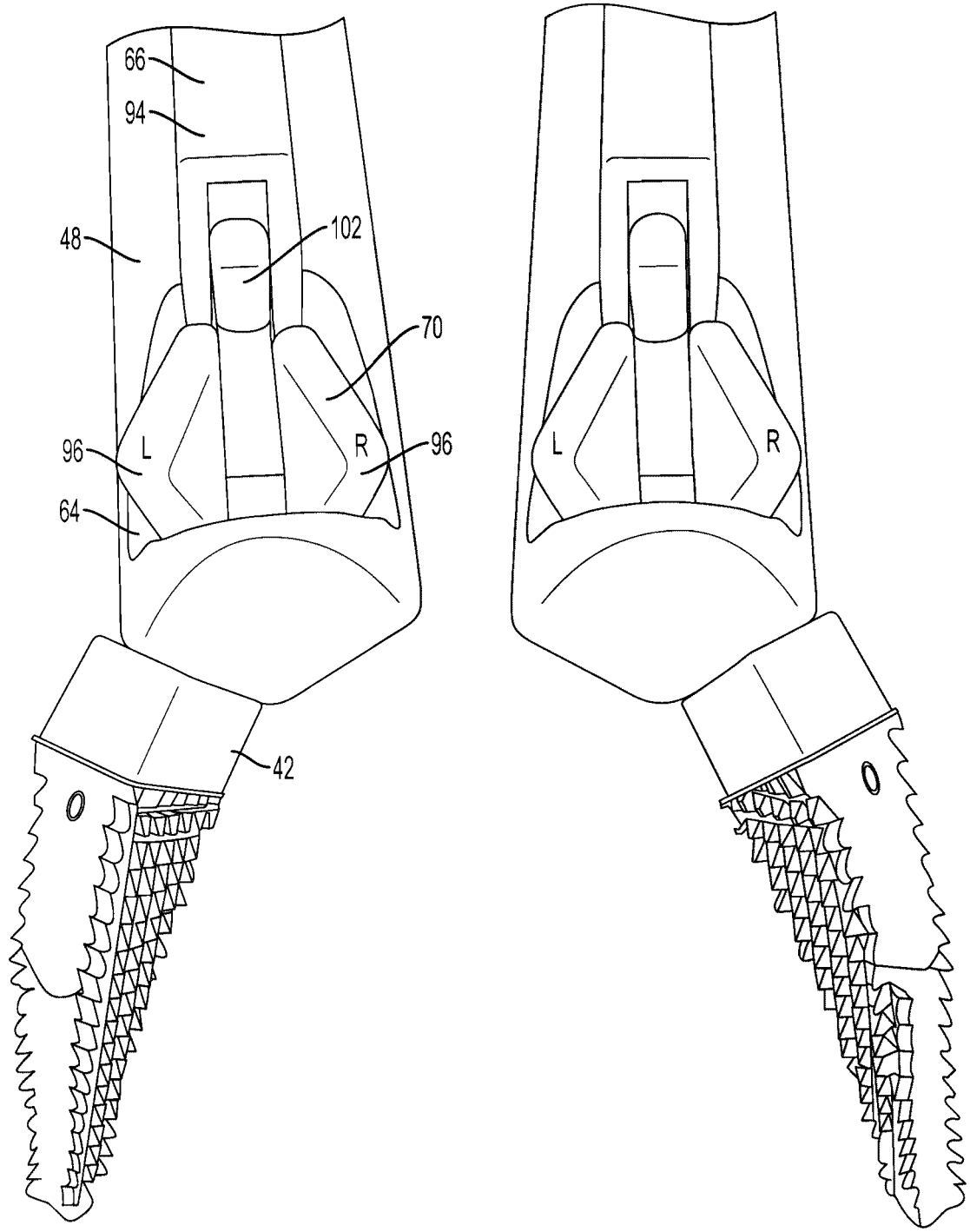
FIG. 30 shows a close-up view of a distal portion of the instrument assembly of FIG. 6, which better illustrates portions of the linkage mechanism.
FIG. 31 shows a close-up view of a distal portion of the instrument assembly of FIG. 7, which better illustrates portions of the linkage mechanism.
Figure 32:
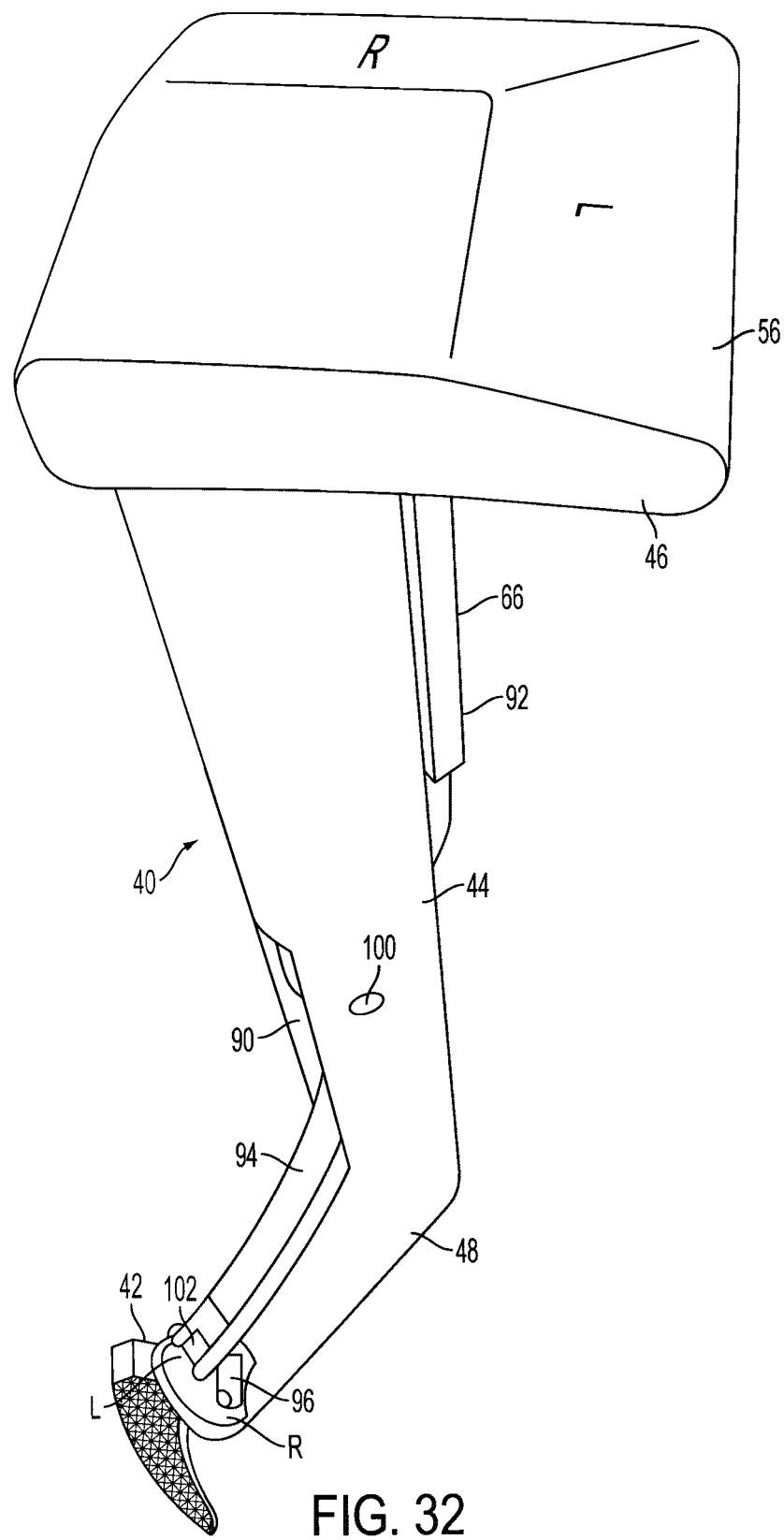
FIG. 32 is a perspective view of the instrument of FIG. 20, which shows certain indicia.

FIGS. 30 and 31 show the link 94, the interposition structure 70 in the form of claws or pawls 96, and the link-to-interposition structure connection 102 and how they can be positioned relative to linkage accommodation 64 according to some embodiments. FIGS. 30 and 31 make clear that, in this particular structure shown in these figures, a left claw or pawl 96 corresponds to the opening 62 into which shaping member 42 fits for surgery on a left femur 18, while a right claw or pawl 96 operates similarly to constraining shaping member 42 for surgery on the right femur 52. Various structures and linkages may be used. FIG. 32 shows an alternate perspective view of the spatial relationships between the strike plate 56 and the shaping member 42 when configured for operating on a left femur.

Figure 33A:
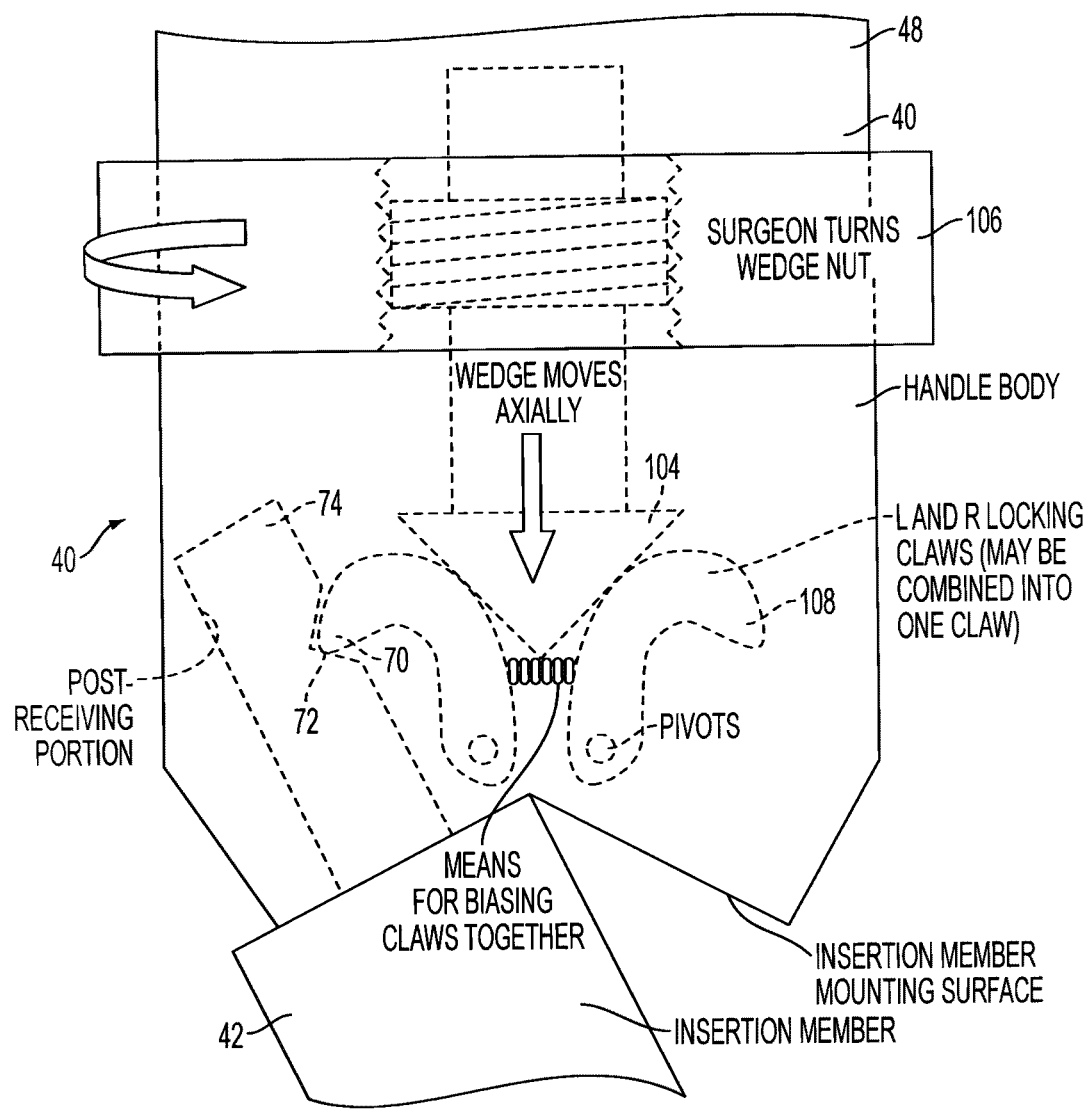
FIG. 33A shows an interposition structure according to a first alternate embodiment according to the present invention.
Figure 33B:
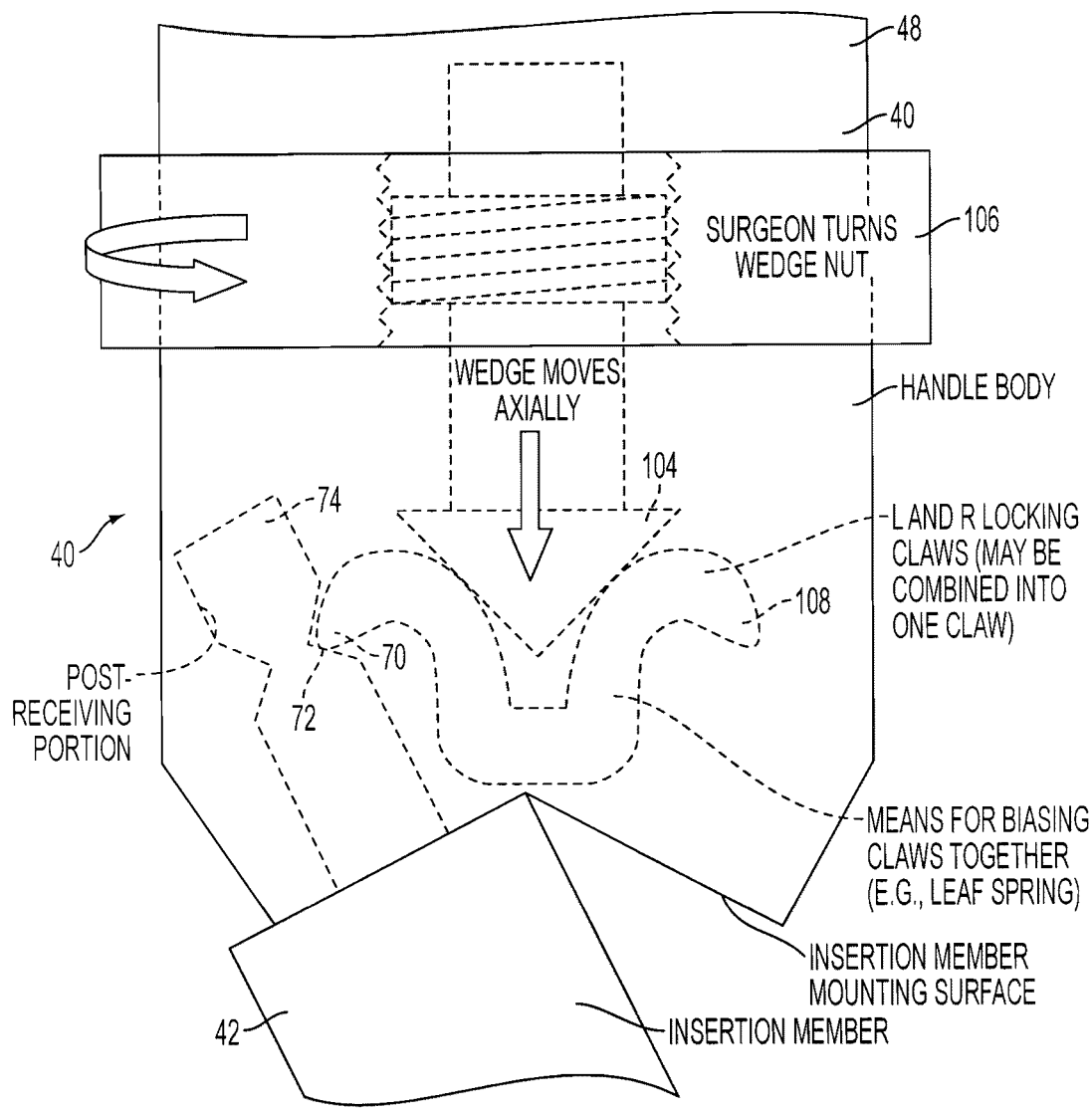
FIG. 33B shows an interposition structure according to a second alternate embodiment according to the present invention.

FIG. 33A shows a schematic of another instrument 40 locking mechanism that features another type of interposition structure 70. There, a wedge 104 is urged distally by rotation of a wedge nut 106 provided as a graspable externally rotatable sleeve on the offset 48 to bear against and urge, in turn, locking claws 108 about pivots 110 into place in interposition structure cooperation structure 72 of shaping member 42. A means for biasing said claws 108 together such as a return spring as shown may be provided. The return spring may be of any type including compression springs, torsional springs, or leaf springs. As shown in FIG. 33B, the claws 108 may themselves be provided with said means for biasing, for instance, designed with integral leaf springs. Insertion members 42 described herein may be provided with ambidextrous connecting portions as shown in FIG. 33B.

Instruments according to other embodiments of the present invention can create an anterior and lateral handle-to-shaping-member offset to achieve the universal left leg-right leg aspect of the invention by using, among other things, pivoting structure, repositionable structure, transpositionable structure or, as is the case in some respects with respect to the first two embodiments discussed above, an instrument which is multiconfigurable to accommodate both legs. Such instruments can have one offset which extends between shaping member 42 and handle 44 in a direction that has lateral, anterior and superior directional components for each desired femur 18, 52, or the shaping member 42 may be offset from handle 44 using structure that may include one or more sections or portions, one, some or all of which may include multiple shapes and extend in different directions. Examples are discussed below, with the understanding that the invention comprehends any instrument that is configurable to accommodate surgery on the intramedullary canal of both the left femur 18 and right femur 52 including a handle and/or a strike plate portion and a shaping member and containing structure that creates an offset of the handle and/or strike plate portion both laterally and anteriorly from the shaping member, for each of the left femur 18 and right femur 52, while the handle and/or strike plate portion and shaping member remain generally parallel or aligned for effective force transmission to the shaping member from the handle or strike plate portion. Note that embodiments with a single distal opening 62 may not allow the shaping member 42 axis to be generally parallel with the handle.

Figure 34:
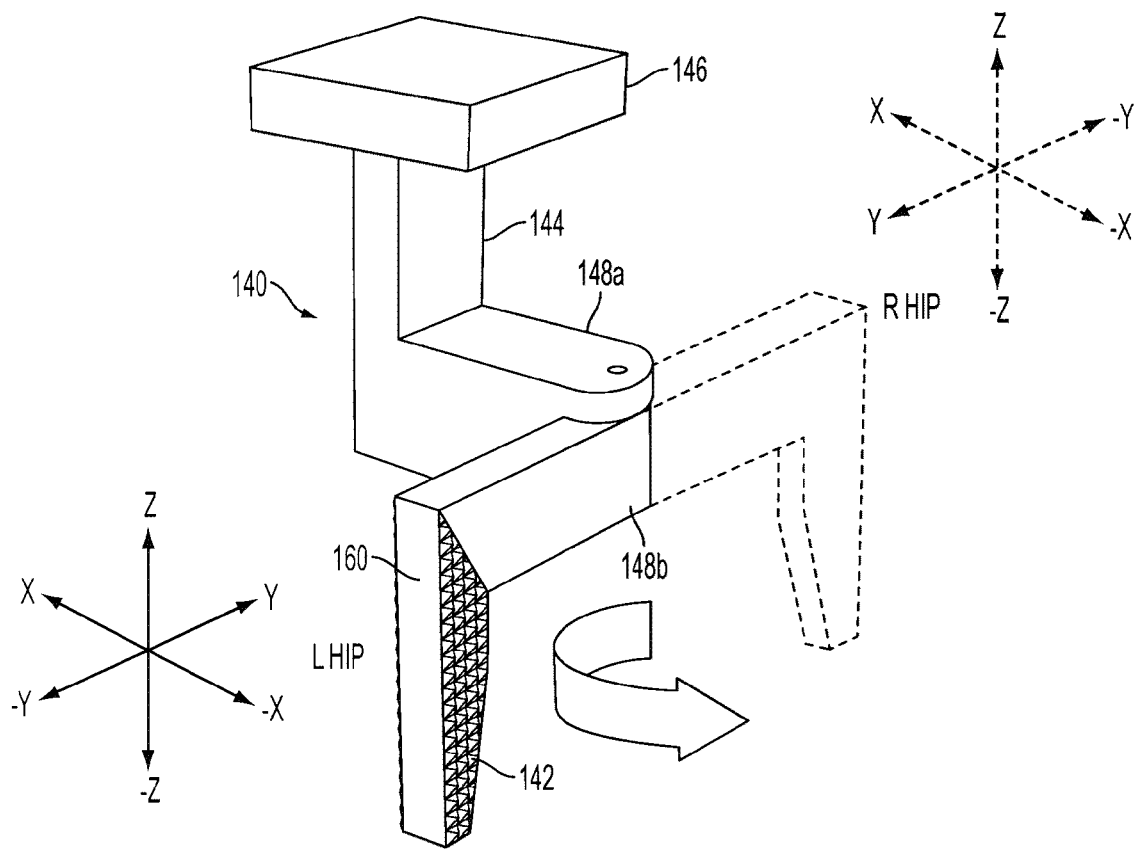
FIG. 34 shows a first alternate embodiment of an instrument according to the present invention.

FIG. 34 shows an instrument 140 according to a first alternate embodiment of the invention that uses a pivoting structure to achieve the left-right universality aspect of the invention. Handle 144 is connected to a first offset 148(a) which extends generally orthogonally from handle 144. Second offset 148(b) is pivotally connected to first offset 148(a) to extend either way from first offset 148(a) to cause first 148(a) to extend along the negative Y axis, in order to allow instrument 140 to accommodate either the left femur 18 or right femur 52 respectively. Shaping member 142 is shown in FIG. 34 integral to second offset 148(b), though it may be connected to offset 148(b) via any desired instrument connection structure 160. A strike plate 146 may contain bevels (not shown) which can be similar to beveled surfaces 56 of instrument 140 of the first embodiment to improve the direction of force transmission to the shaping member 142.

Figure 35:
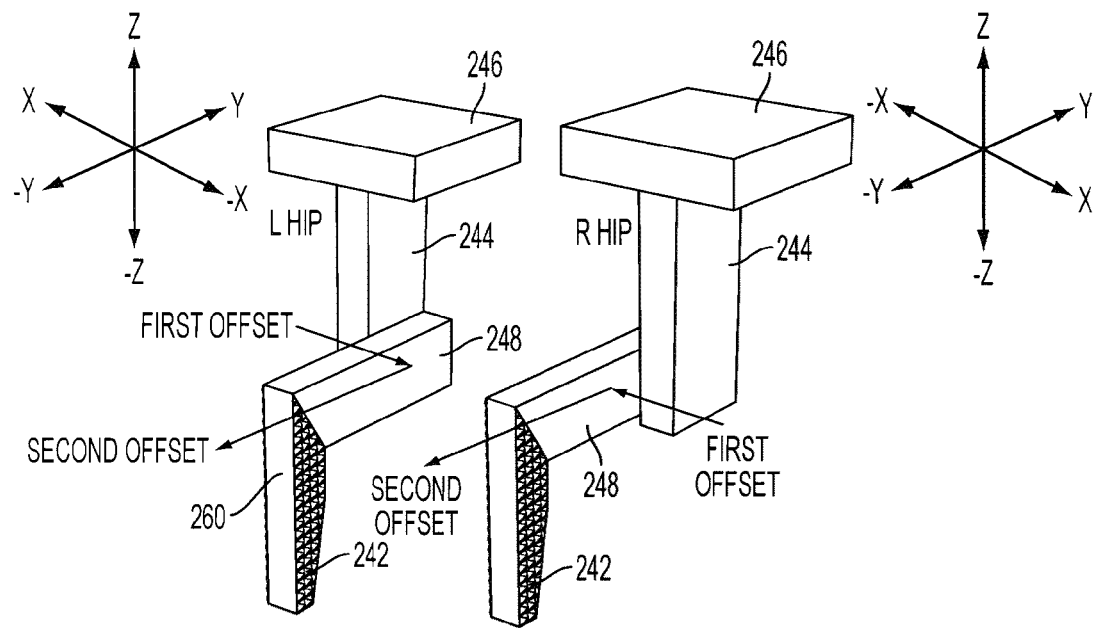
FIG. 35 shows a second alternate embodiment of an instrument according to the present invention.

FIG. 35 shows an instrument 240 according to a second alternate embodiment of the invention that uses a repositionable structure to accomplish offset of handle 244 relative to shaping member 242. Handle 244 extends in a distal or negative Z direction and can be attached to an offset 248 on either side of the handle 244. The connection to the side of the handle 244 is the structure that creates an offset in the X direction in order to create the lateral offset, while offset 248 extends in the posterior or negative Y direction to create the lateral and anterior offset of handle 244 relative to shaping member 242. The offset 248 can be connected to handle 244 using screws, clevis pins, tongue and groove structure, mating key ways or slides, spring and latch mechanisms, detents or any other desired structure. Again, any desired interconnection structure 260 can be used, if one is needed, to connect shaping member 242 to offset 248.

Figure 36A:
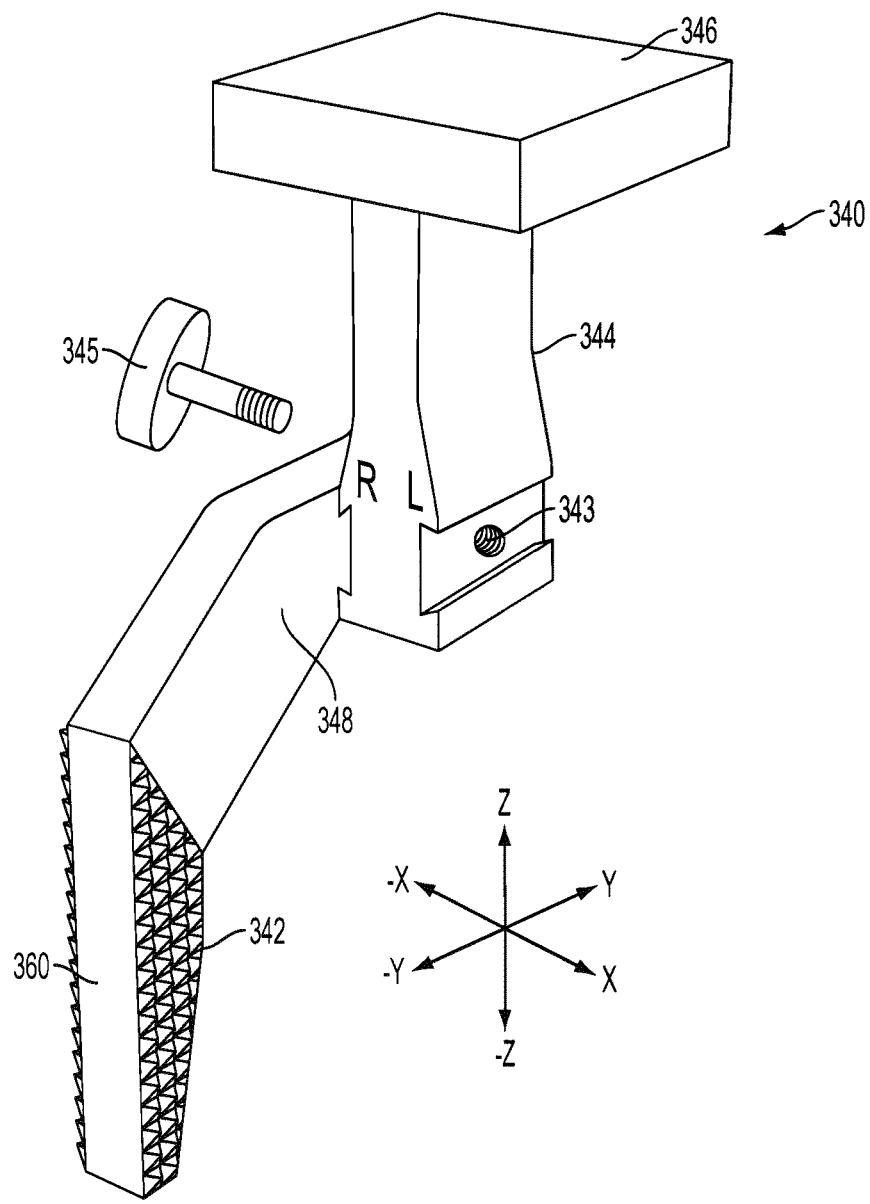
FIG. 36A shows an alternative embodiment of a locking mechanism according to the present invention.
Figure 36B:
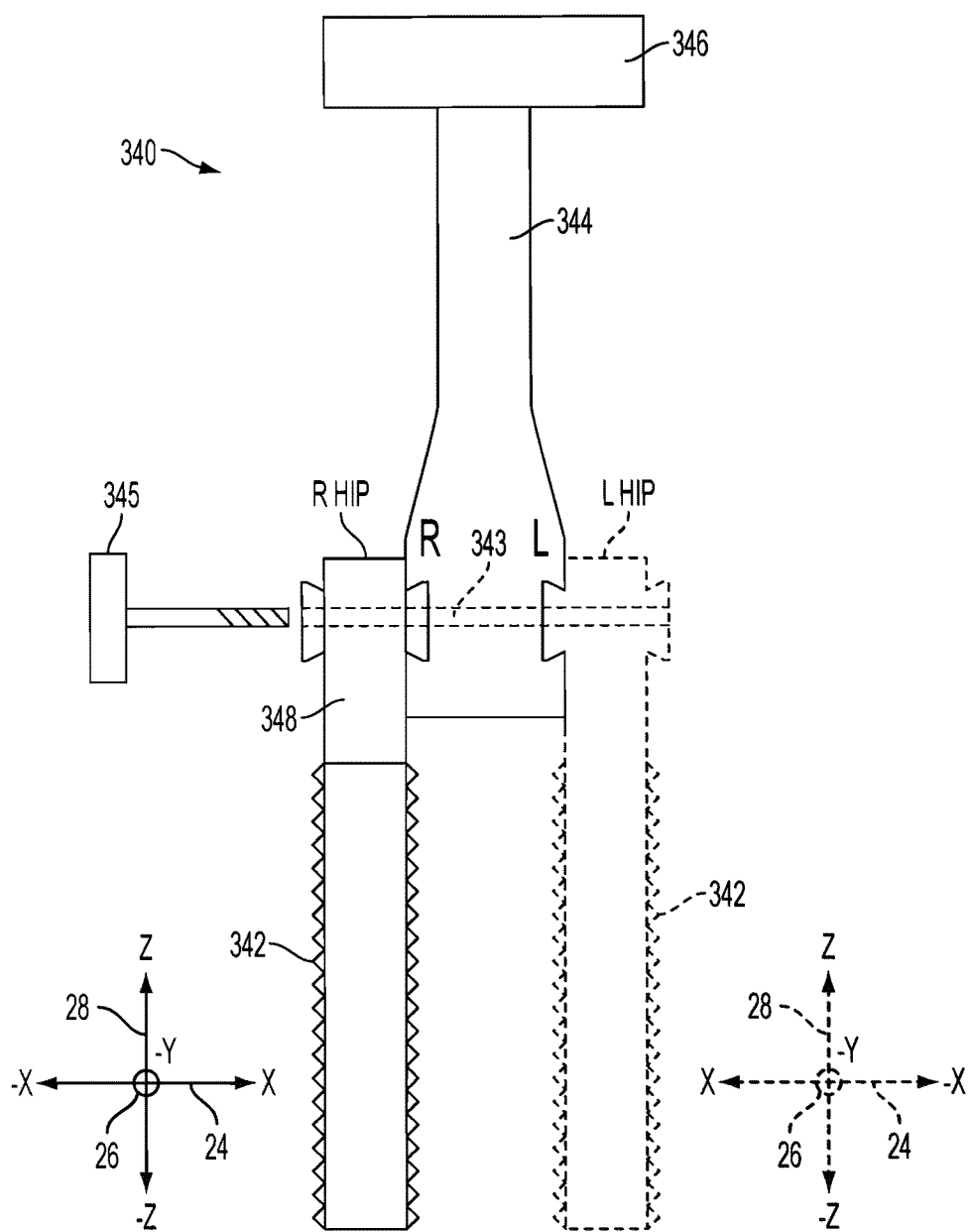
FIG. 36B shows a posterior perspective view of the instrument of FIG. 36A.
Figure 36C:
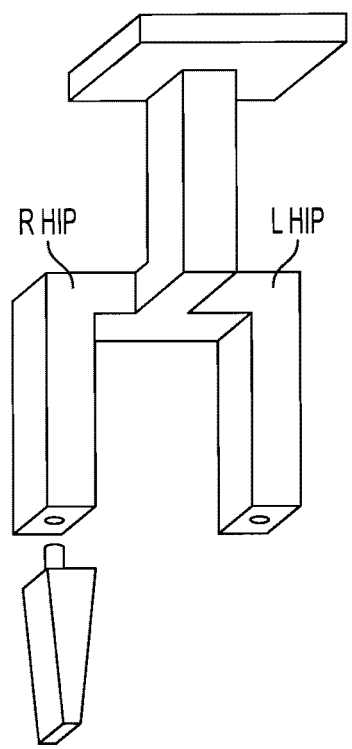
FIG. 36C shows a dual offset handle of FIG. 36B with integral right and left offsets.

FIGS. 36A and 36B a modular instrument 340 according to some embodiments of the invention that use repositionable structure to achieve an offset in accordance with the invention. There, handle 344 receives an offset 348 that is connectable at either end to handle 344 and at either end to shaping member 342. The offset 348 extends from the handle 344 in a direction that includes a negative Y or posterior directional component and an X directional component. When the offset 348 is manipulated so that its other end is connected to handle 344, the offset in the X direction is changed to accommodate the contra-lateral hip. For instance, if a first end of offset 348 is connected to handle 344 and the offset extends in the direction that contains a negative Y directional component and an X directional component to accommodate a left femur, its other, second end can be connected to handle 344 on an opposing side of the handle 344 axis, so that it extends from handle 344 in a direction that accommodates the other femur. Offset 348 can be straight, curved, doglegged, or any other desired shape. It can be connected to handle 344 and shaping member 348 via any desired structure including screws, clevis pins, tongue and grooves, mating key ways or slides, spring and latch mechanisms, detents or as otherwise desired. In some embodiments, as shown in FIG. 36C, two offsets 348 may be integrally provided on handle 344 in order to create a Y-shaped instrument. During use, only one offset 348(a) is used and provides a lateral and anterior offset, while the other offset 348(b) provided for use with the contra-lateral hip extends away from the surgical site and floats in space.

Figure 37:
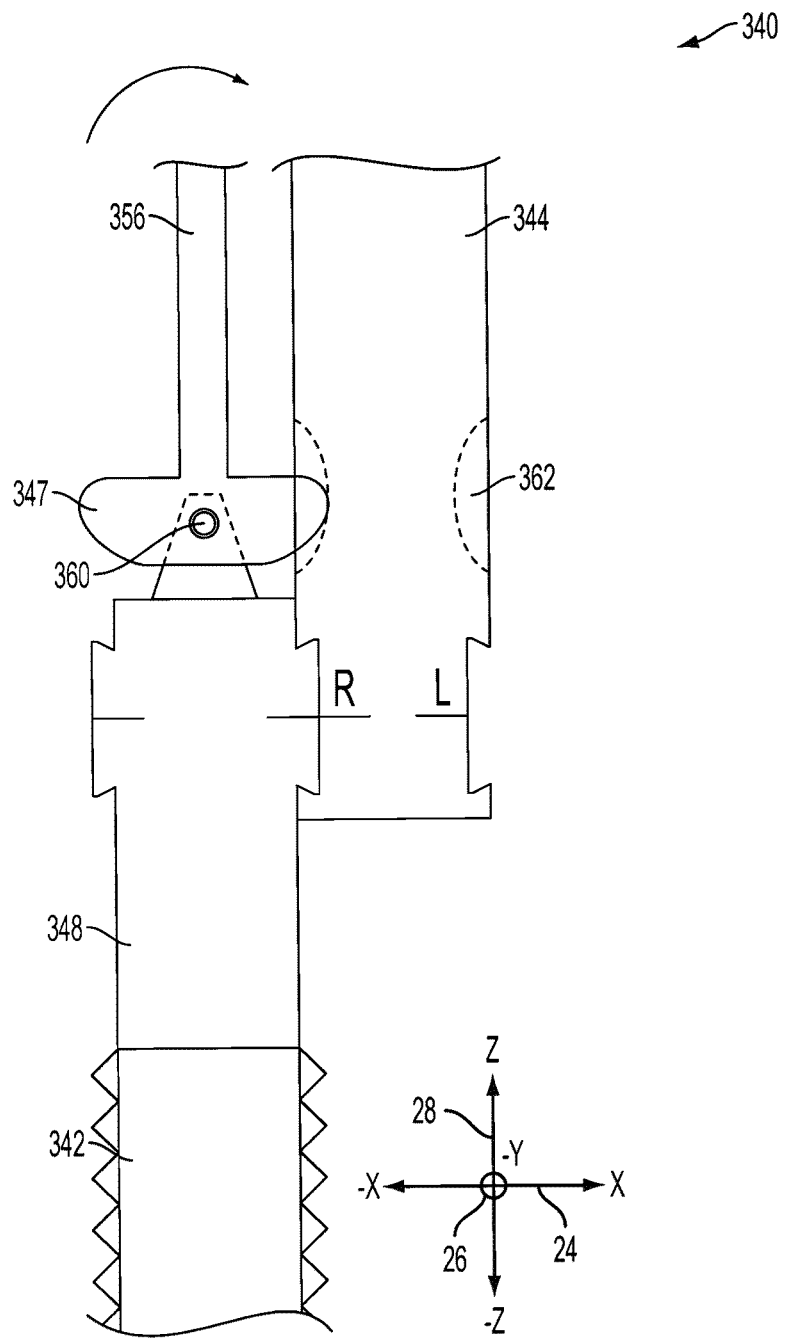
FIG. 37 shows a locking mechanism according to another aspect of the present invention.

As shown in FIG. 37, an ambidextrous cam and follower arrangement 347 may be provided on either one of or both of the handle 344 and offset 348 to secure the offset 348 to the handle 344. A rotatable lever 356 may be provided on a pivot structure 360 in order to facilitate movement between the cam and follower arrangement 347 by way of mechanical advantage, thereby creating a frictional lock between the handle 344 and the offset member.

Figure 38A:
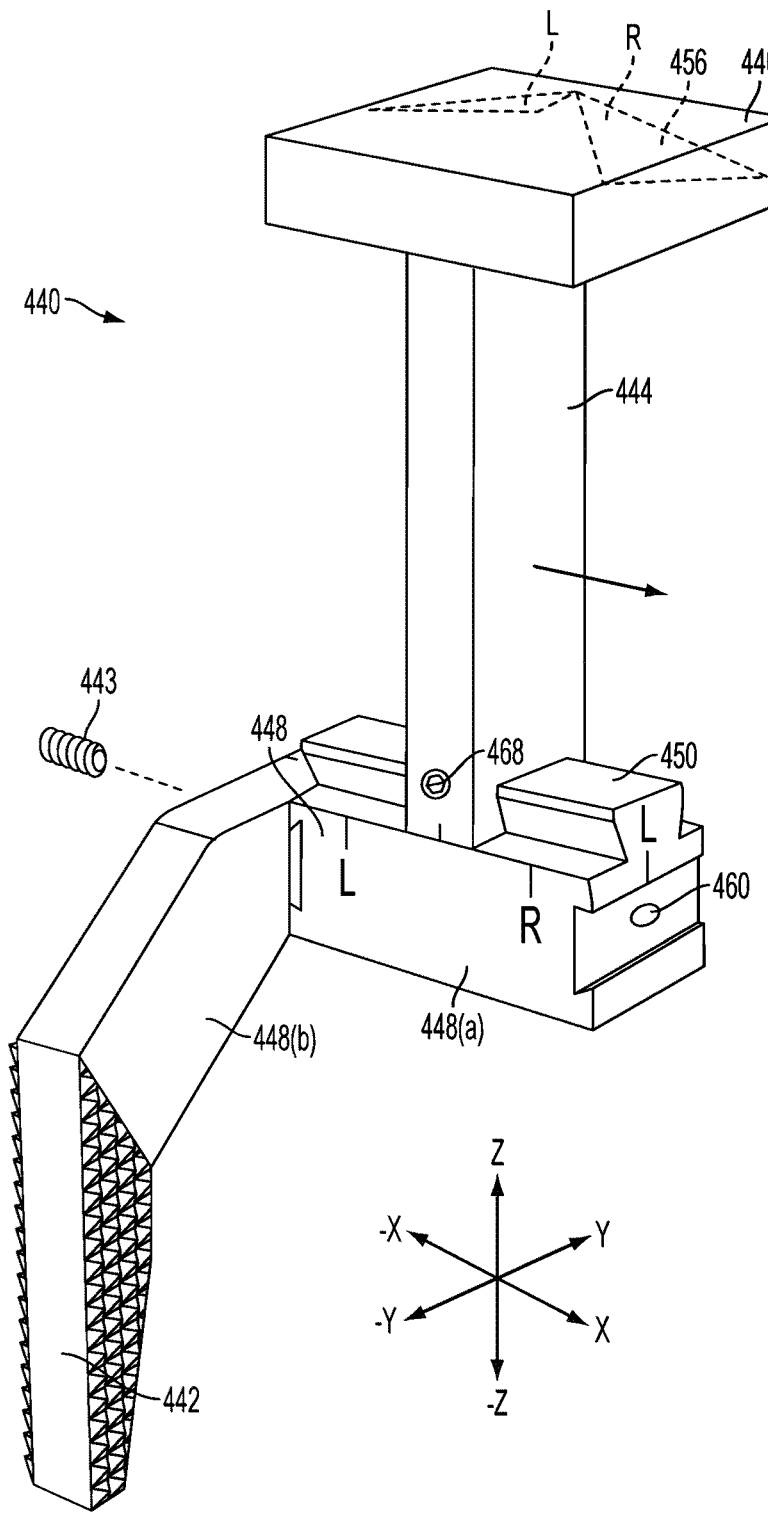
FIG. 38A shows a third alternate embodiment according to the present invention.

FIGS. 38A-38C show an instrument 440 according to a third embodiment of the invention. There, a handle 444 is slideably connected to a first offset 448(a) which in turn connects to a second offset 448(b). The sliding engagement between the handle 444 and first offset 448(a) may be facilitated by a track 450 having means 468 for fixing the handle 444 to the first offset 448(a), such as a set screw or spring-loaded latching button. The first offset 448(a) and second offset 448(b) help align the longitudinal axis 468 of shaping member 442 to be essentially parallel with longitudinal axis 454 of handle 444. First offset 448(a) slides relative to handle 444 in order to provide the lateral offset desired for left or right femur. Either or both first offset 448(a) or second offset 448(b) can extend in a direction that includes the posterior or negative Y component in order to provide the desired anterior offset of handle 444 relative to shaping member 442. Second offset 448(b) may be provided with adjustment means, such as an adjustable track means 460 (best shown in FIG. 38A) in order to vary the amount of anterior offset. In other words, an offset in the Y-axis between the handle 444 and shaping member 442 may be varied and set by securing the second offset 448(b) to the first offset 448(a) via securing means 443. Moreover, while shaping member 442 and second offset 448(b) are shown to be integral in FIGS. 38A-C, it will be appreciated that second offset 448(b) may be provided with an interposition structure 470 configured to accept and to secure thereto, one or more separable shaping members. Any desired locking mechanism 468, 460 may be used to lock the slideable first offset 448(a) and second offset 448(b) into place, and any desired interposition structure can be used, as disclosed in this document or otherwise, and as is the case with all embodiments disclosed in this document, to retain shaping member 442 in position relative to instrument 440.

Figure 39:
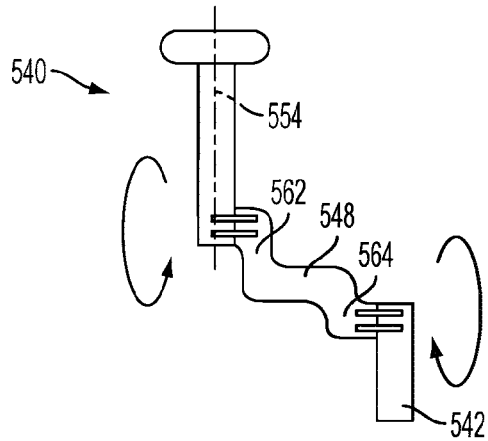
FIG. 39 shows a fourth alternate embodiment according to the present invention.

FIG. 39 shows an instrument 540 according to a fourth embodiment of the present invention. There, handle 544 is connected in pivoting fashion to an offset 548 that pivots or swivels relative to the longitudinal axis 554 of handle 544. Offset 548 extends in a direction that includes an X directional component and a negative Y or posterior directional component. When the offset 548, handle 544, and shaping member 542 are swiveled to a first position, it provides desired lateral and anterior offset of handle 544 relative to shaping member 542 to accommodate a first leg. When the offset 548, handle 544, and shaping member 542 are pivoted and locked in the other position, it provides desired lateral and anterior offset to accommodate the other leg. Again, the pivoting connection between handle 544 and offset 548 can be constructed as desired with suitable locking mechanism, and the shaping member 542 can be connected to offset 548 with interconnection structure 560 as desired.

Figure 40:
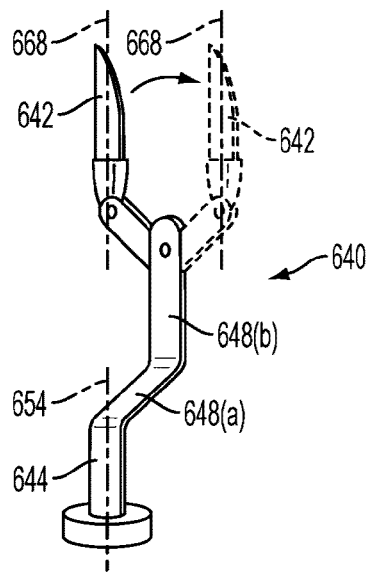
FIG. 40 shows a fifth alternate embodiment according to the present invention.

FIG. 40 shows an instrument 640 according to a fifth embodiment of the present invention. There, handle 644 having a handle axis 654 is connected to an offset 648 that extends from handle 644 to shaping member 642 in a direction or directions that include or includes a negative Y or posterior component. Offset 648 may comprise one or more offset portions 648a, 648b. Attached distally thereto is a link which, depending upon the direction on which said link is pivoted relative to handle 644 and offset 648, provides an X directional component to provide the desired lateral offset of handle 644 relative to shaping member 642 for either a left or a right femur. In this version, the pivoting of the link occurs relative to handle 644 about the Y/negative Y axis to provide the left-right universality aspect of the invention. The shaping member 642 can be connected on either side of the distal end of the offset 648 so that it extends in a distal or negative Z direction from offset 648. It is preferred that the shaping member axis 668 remains generally parallel to the handle axis 654 in both left and right hip configurations. Any desired interconnection structure can be used to connect shaping member 642 to offset 648.

Figure 41:
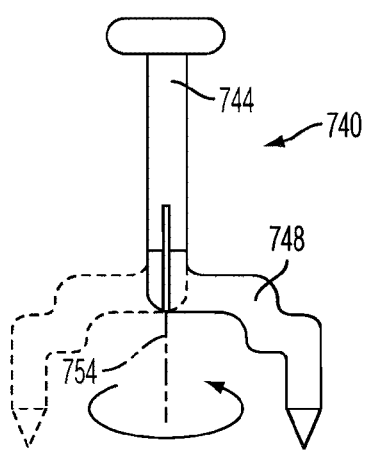
FIG. 41 shows a sixth alternate embodiment according to the present invention.

FIG. 41 shows an instrument 740 according to a sixth embodiment of the invention. There, handle 744 is connected in pivoting fashion to an offset 748 that pivots or swivels relative to the longitudinal axis 754 of handle 744. Offset 748 extends in a direction that may include a negative Z or distal directional component, a negative Y or posterior directional component, and an X directional component. When the offset 748 is swiveled to a first position, it provides desired lateral and anterior offset of handle 744 relative to shaping member 742 to accommodate a first leg. When pivoted and locked in the other position, it provides desired lateral and anterior offset to accommodate the other leg. Again, the pivoting connection between handle 744 and offset 748 can be constructed as desired with suitable locking mechanism, and the shaping member 744 can be connected to offset 748 with any interconnection structure as desired.

Figure 42:
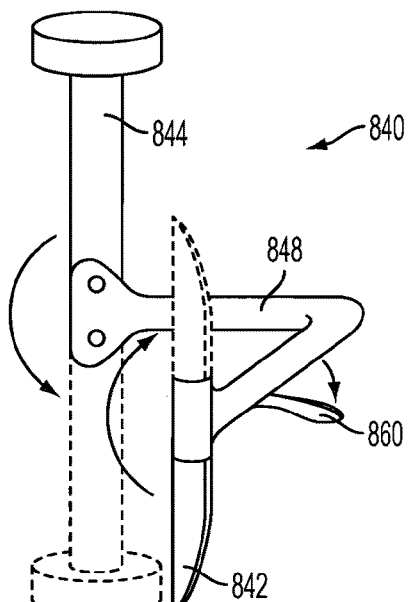
FIG. 42 shows a seventh alternate embodiment according to the present invention.

FIG. 42 shows an instrument 840 according to a seventh embodiment of the invention, which is similar in some respects to the embodiment shown in FIG. 39. There, handle 844 is pivotally connected to an offset 848 that extends from handle 844 to the shaping member in both a negative X (or medial) direction, and a negative Y (or posterior) direction in order to provide lateral and anterior offsets to the handle 844 relative to the shaping member 842. In this version, the pivoting of the handle 844 occurs relative to offset 848 about the Y/negative Y axis to provide universality. The shaping member 842 can be connected on either side of the distal end of the offset 848 so that it extends in a distal or negative Z direction with respect to the handle 844 position. Any desired interconnection structure 860 can be used to connect and disconnect shaping member 842 to offset 848; here, a release lever on the offset is shown.

Figure 43:
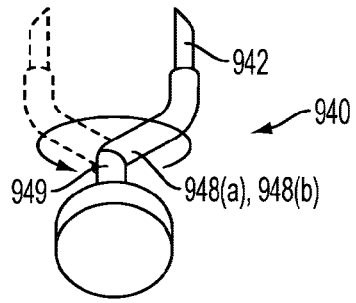
FIG. 43 shows an eighth alternate embodiment according to the present invention.
Figure 44:
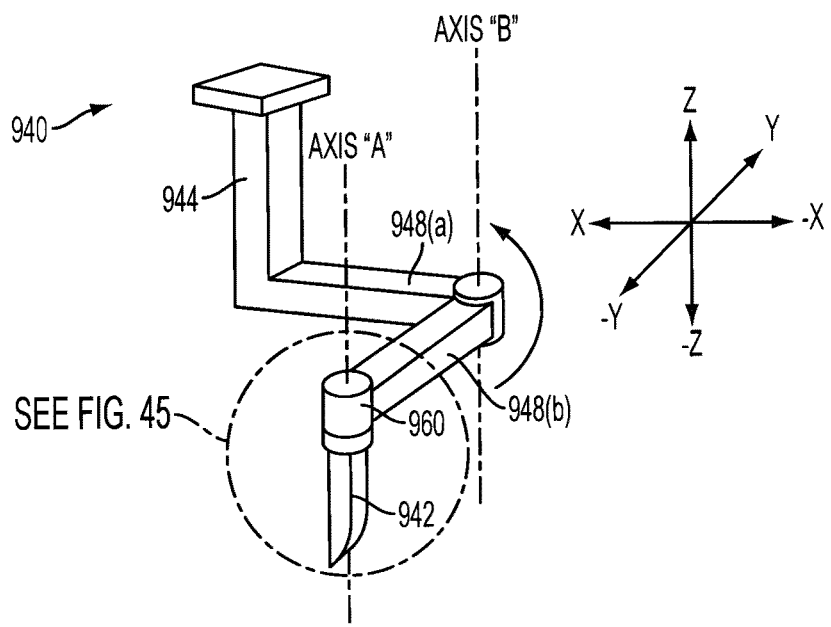
FIG. 44 shows a ninth alternate embodiment according to the present invention configured for operating on a left femur.
Figure 45:
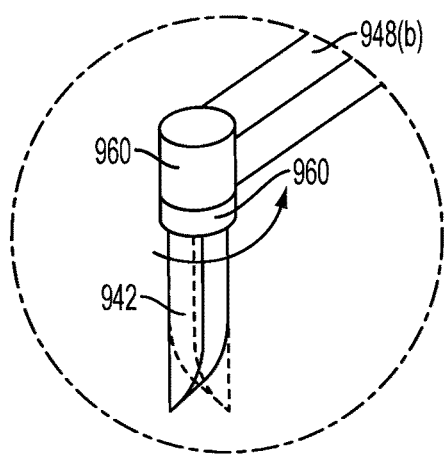
FIG. 45 shows portions of the embodiment of FIG. 44.

FIGS. 43-45 show an instrument 940 according to another version of pivotable embodiments according to the present invention. There, handle 944 is connected to a first offset 948(*a*) that extends from handle 944 in a negative X or medial direction. The second offset 948(*b*) is pivotally connected to the first offset 948(*a*) to extend in the negative Y direction to provide anterior offset of handle 944 relative to shaping member 942. The pivot structure that connects first offset 948(*a*) to second offset 948(*b*) can be constructed as desired with locking structure to lock second offset 948(*b*) in place to provide the desired lateral offset. As shown more closely in FIG. 45, second offset 948(*b*) can connect to shaping member 942 using interconnection structure 960 in the form of a swivel, if desired in order to accommodate left and right surgical sites. Any other interconnection structure 960 can be used to allow shaping member 942 to be connected to the distal end of second offset 948(*b*) for operation on a first leg in a first position and for operation on the other leg 180 degrees away from that position. As shown in FIG. 43, first and second offsets 948(*a*) and 948(*b*) may be combined into a single length of material that provides both posterior and lateral offset of the handle 944 relative to the shaping member 942 when offset 948(*a*),(*b*) is swiveled to accommodate the right or left leg.

Figure 46:
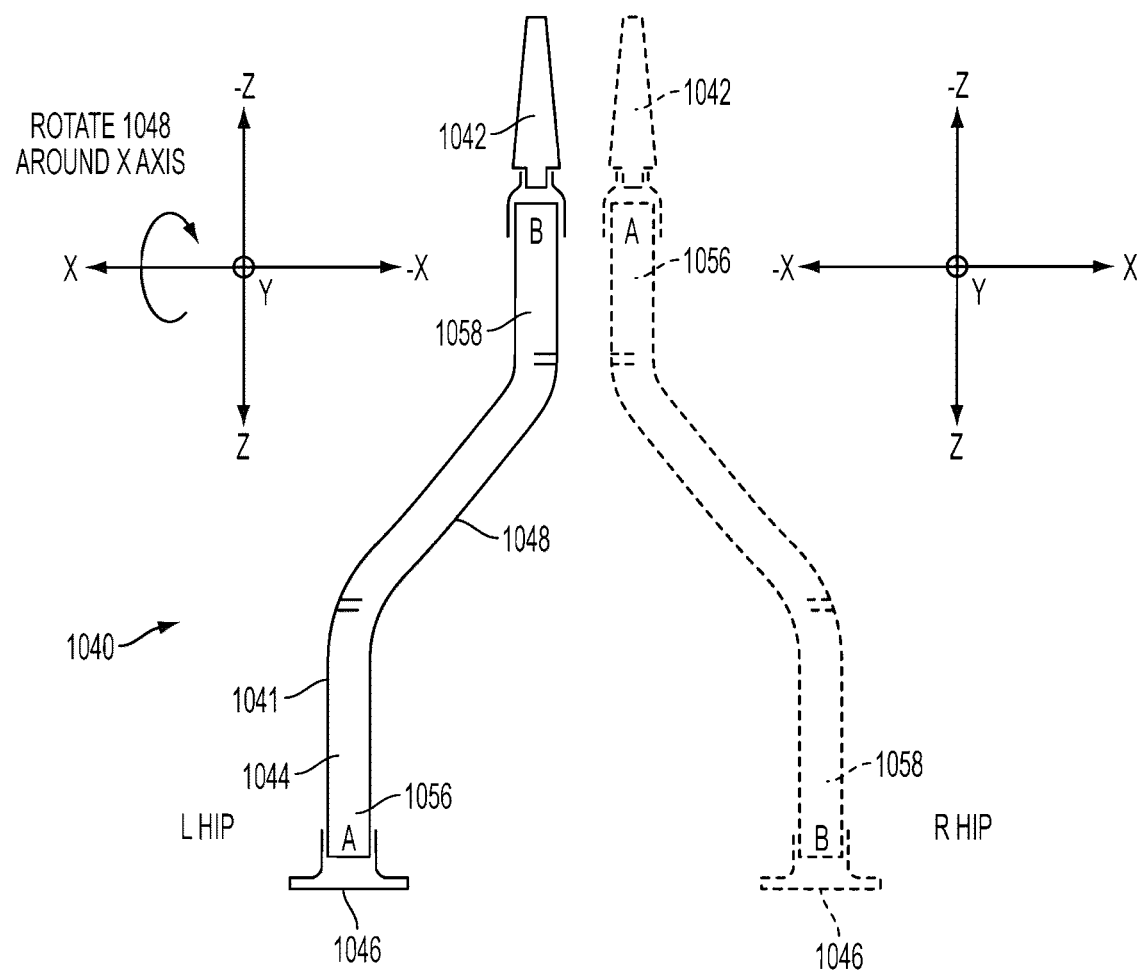
FIG. 46 shows a tenth alternate embodiment according to the present invention.

FIG. 46 shows an instrument 1040 according to another version of multiconfigurable instruments according to the present invention. There, instrument 1040 includes a member 1041 that serves functions of handle 1044 and offset or offsets 1048. The member 1041 includes an "A" end 1056 and a "B" end 1058. When a first leg is the subject of surgery, one of the A and B ends can connect to shaping member 1042 and the other of said A and B ends can connect to a strike plate 1046. When the other leg is the subject of surgery, the member 1041 can be rotated about the X-axis so that the other end connects to shaping member 1042. The end that does not connect to the shaping member 1042 connects to, if desired, a strike plate 1046. The end of member 1041 that connects to the strike plate 1046 can be considered as handle 1044 that proceeds distally in a negative Z direction. It then transitions to an offset portion 1048 that proceeds in a negative Y (or posterior) direction and, a negative X (or medial) direction, then to transition back to a negative Z direction.

Figure 47C:
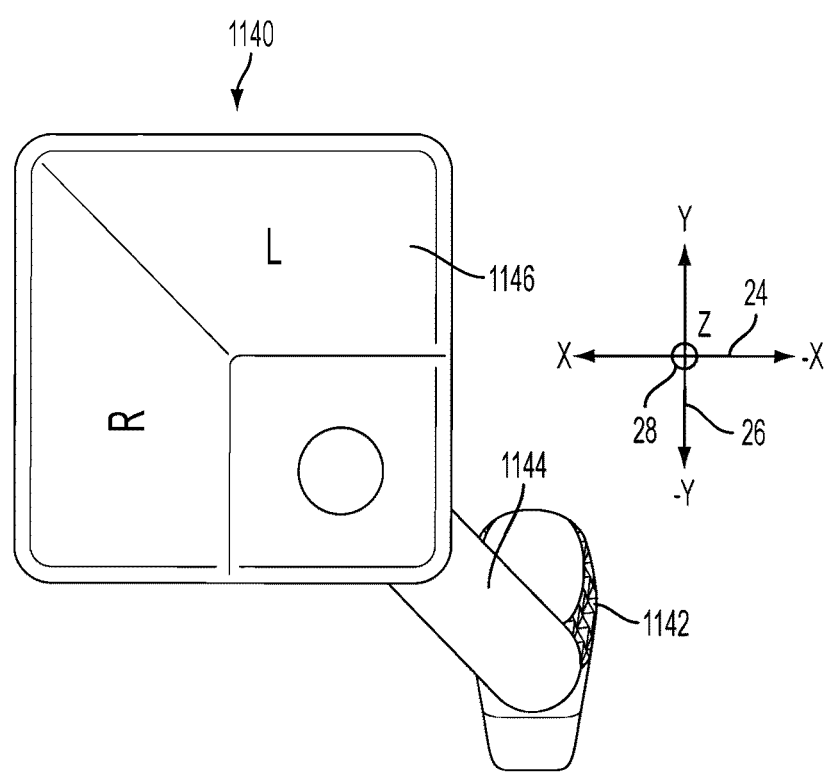
FIG. 47C shows an elevated perspective view of the instrument of FIG. 47A.
Figures 47D, 47E, 47F:
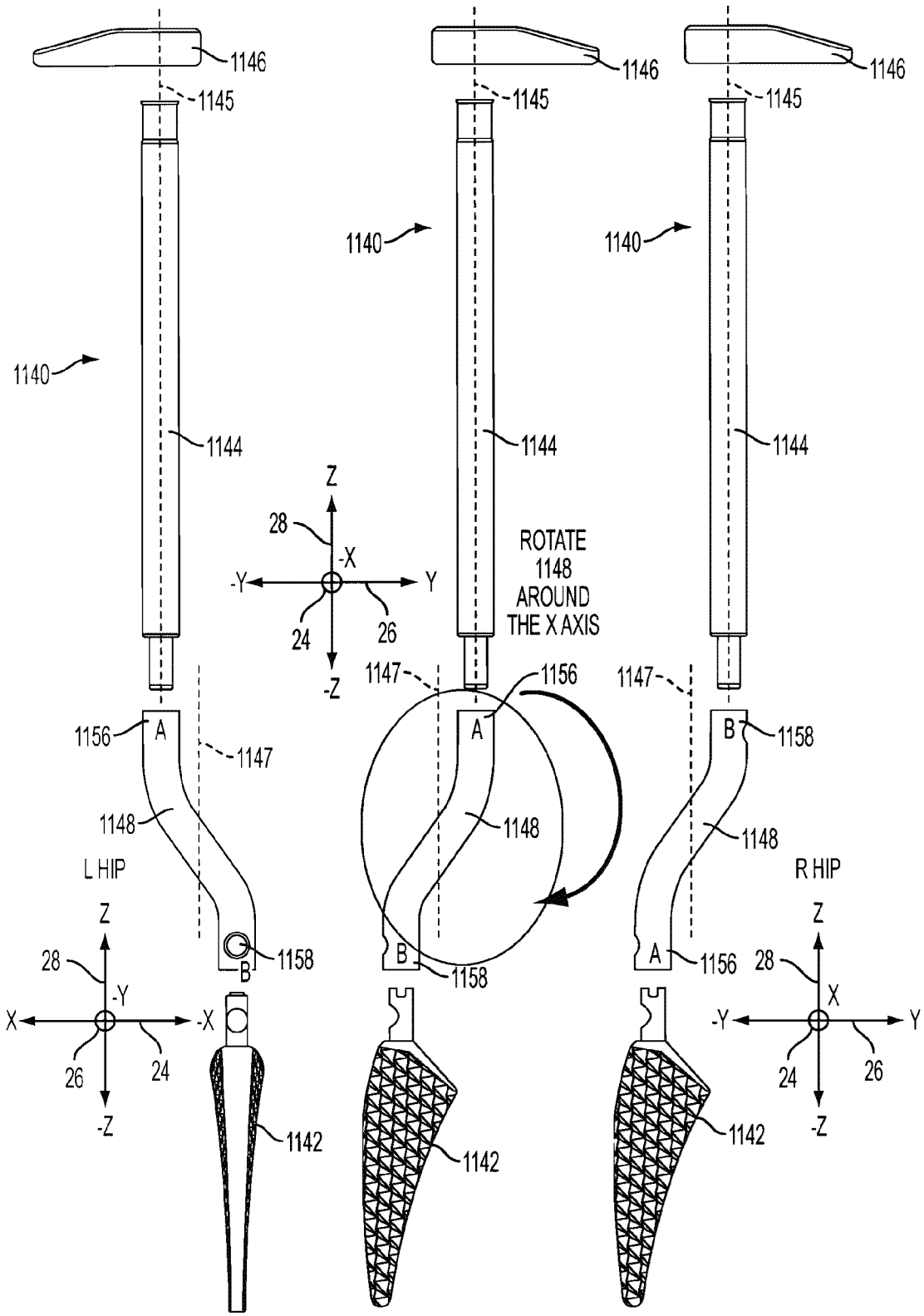
FIG. 47D shows an exploded view of the instrument of FIG. 47B from a posterior perspective.
FIG. 47E is a medial perspective view of the instrument of FIG. 47D, illustrating how an offset component may be rotated for use with a right femur.
FIG. 47F shows an alternate lateral exploded view of the instrument of FIG. 47E after the offset component has been rotated for operating on a right femur.
Figure 47G:
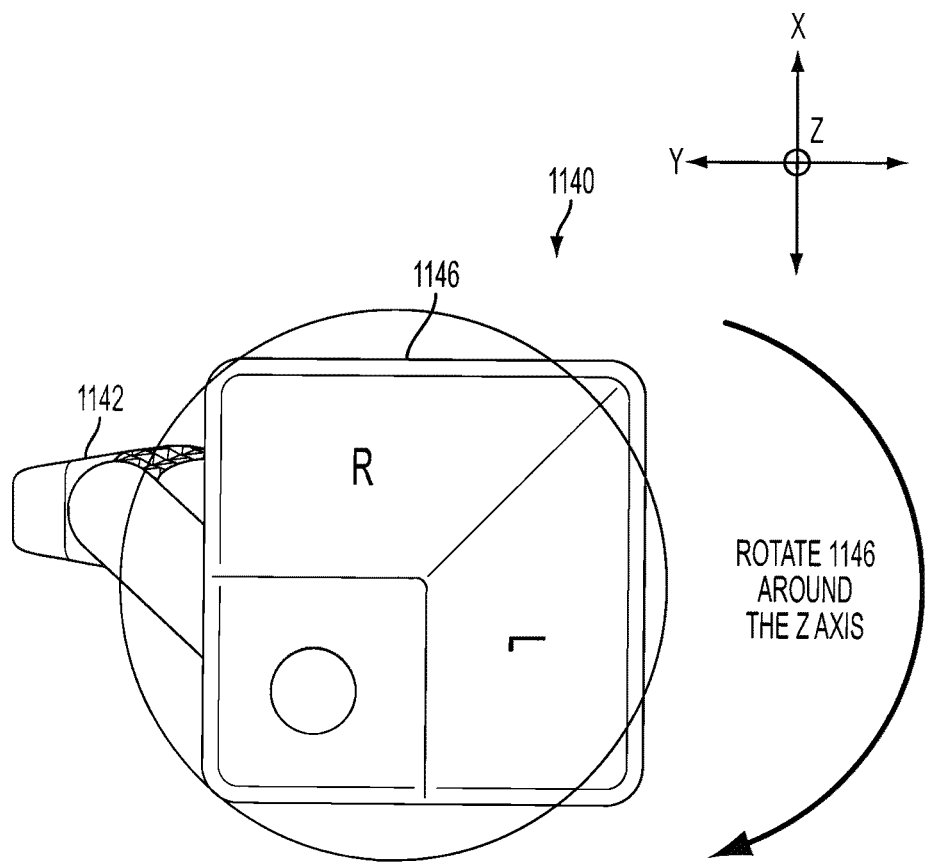
FIG. 47G shows an elevated view of the assembled instrument of FIG. 47F, before the strike plate is rotated for use with a right femur.
Figure 47H:
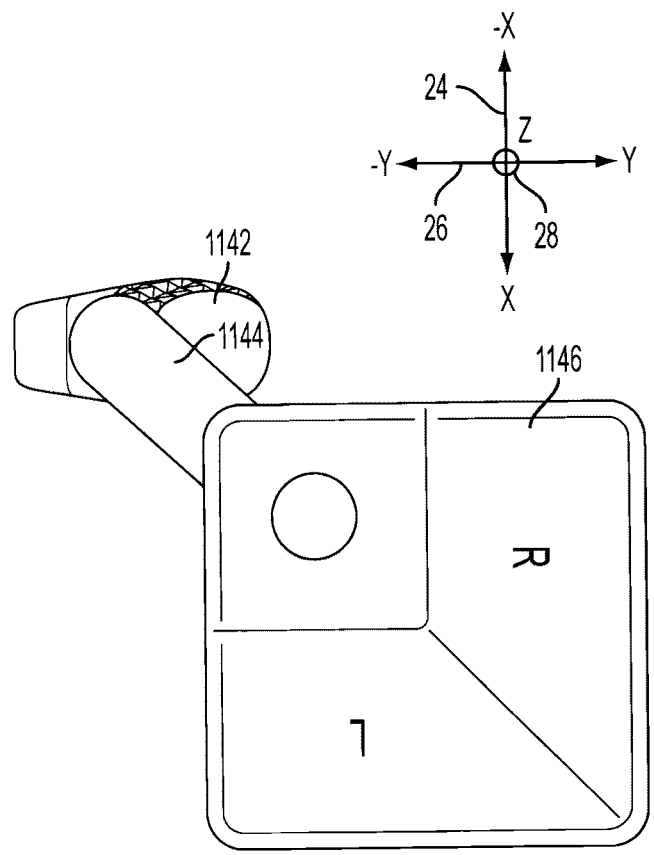
FIG. 47H shows another elevated view of the assembled instrument of FIG. 47G, after the strike plate is positioned for operating on the right femur.
Figures 47I, 47J:
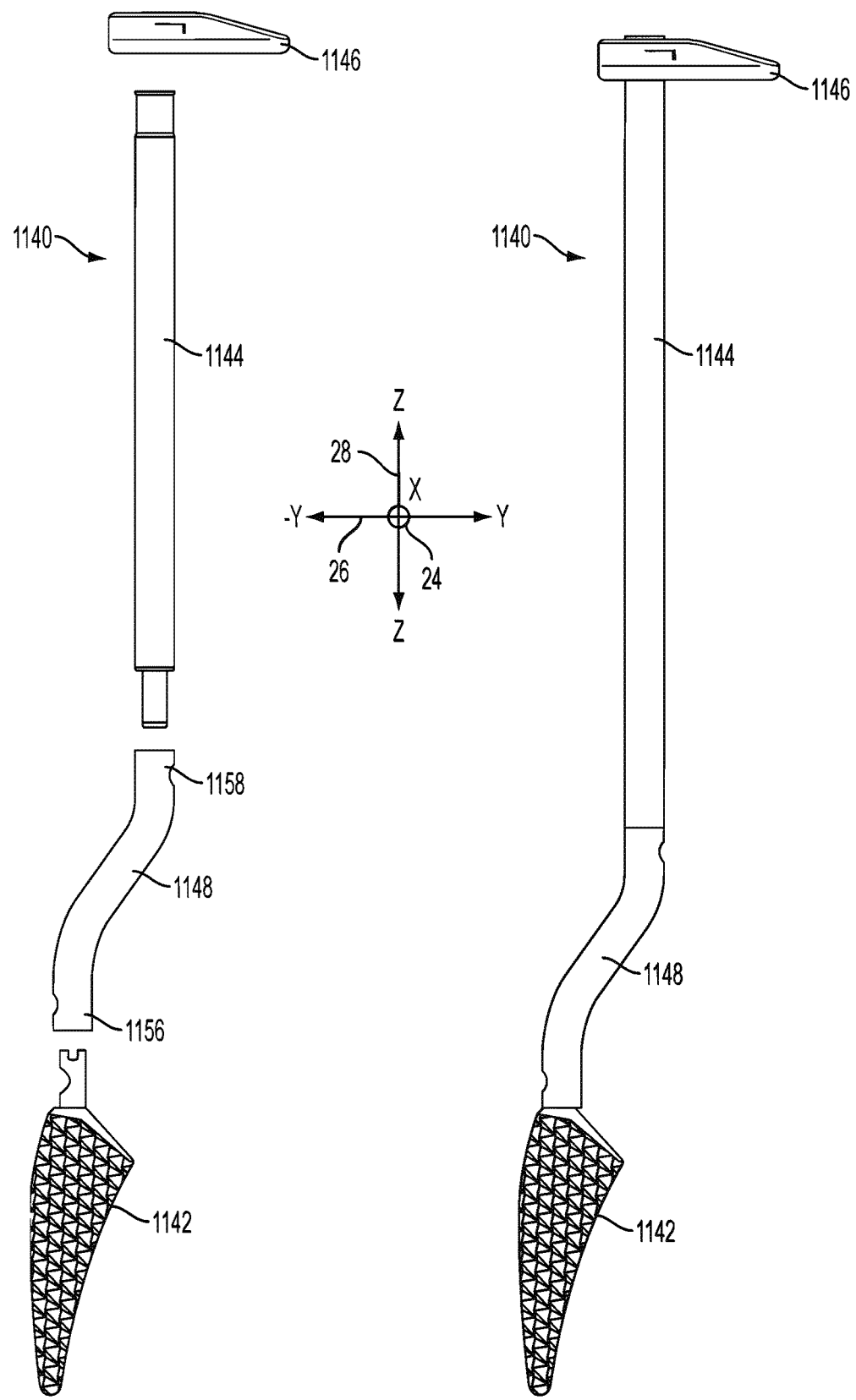
FIG. 47I shows an exploded view of the instrument of FIG. 47H from a lateral perspective.
FIG. 47J shows the instrument of FIG. 47I as assembled.
Figures 47K, 47L:
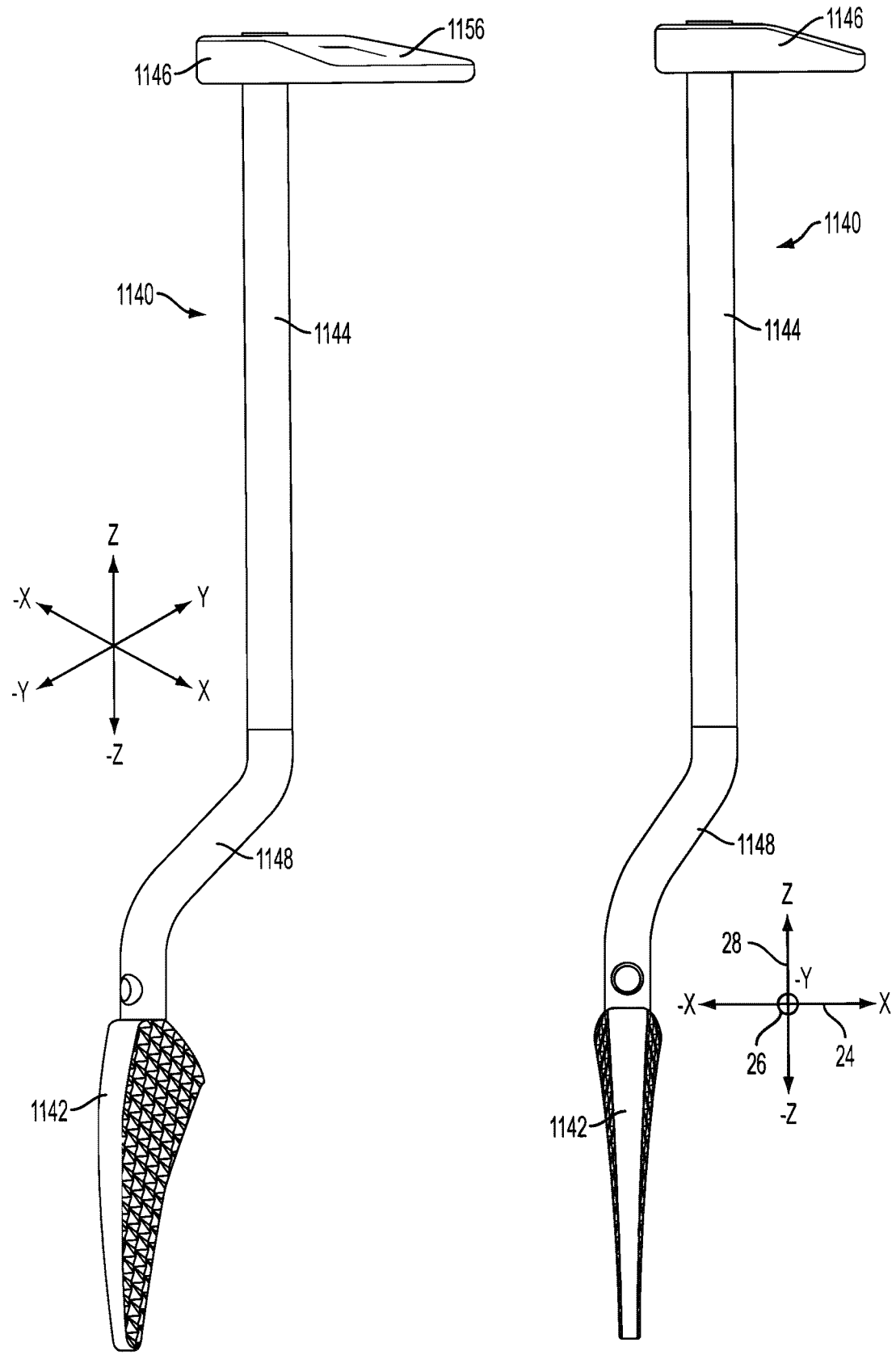
FIG. 47K shows a posterior perspective view of the instrument of FIG. 47J.
FIG. 47L is a posterior perspective view of the instrument of FIG. 47J.
Figure 47M:
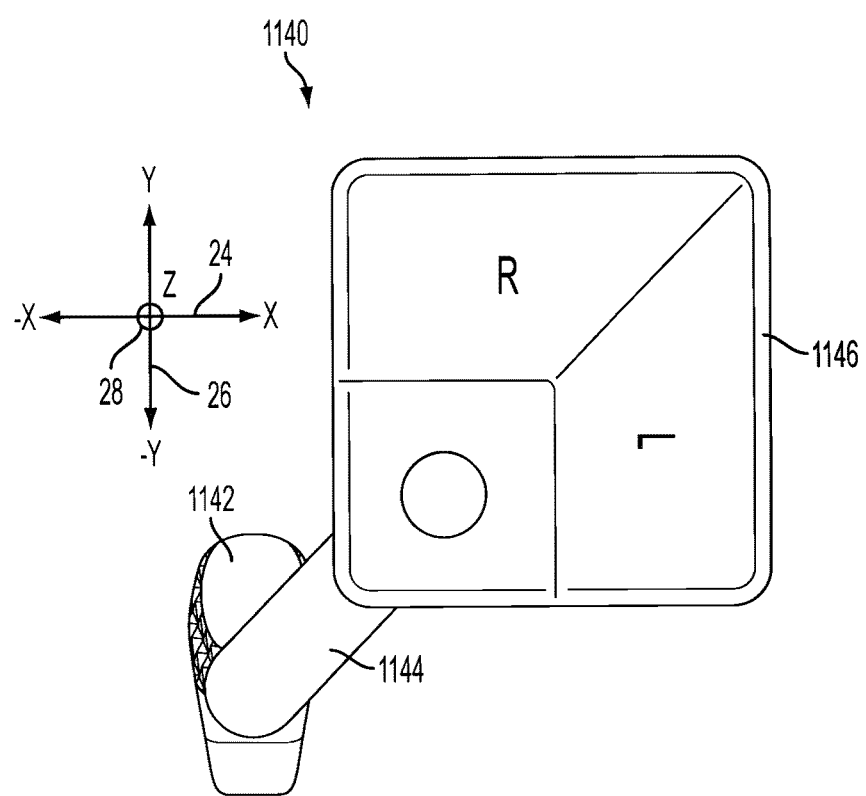
FIG. 47M shows an elevated perspective view of the instrument of FIG. 47L.

FIG. 47A-M show a modular instrument 1140 according to another version of multiconfigurable instruments according to the present invention. In this embodiment, instrument 1040 includes a strike plate 1146, handle 1144, offset 1148, and shaping member 1142. As shown in FIGS. 47D-F, instrument 1140 is modular with respect to strike plate 1146 and handle 1144, with respect to handle 1144 and offset 1148, and with respect to offset 1148 and shaping member 1142. Offset 1148 includes an "A" end and a "B" end, 1156 and 1158 respectively. When a first leg is the subject of surgery, one of the A and B ends of offset 1148 connects to shaping member 1142 and the other of the A and B ends of offset 1148 connects to handle 1144. FIGS. 47A-E show various views of an instrument configured to operate on a left femur. When the other leg is the subject of surgery, offset 1148 is rotated 180 degrees about the X axis, as shown in FIGS. 47D-F, so that the other end of offset member 1148 connects to shaping member 1142 and the opposite end connects to handle 1144. To accommodate the other leg, the strike plate 1146 is also rotated as shown in FIGS. 47G and 47H. FIGS. 47F and 47H-M show various views of the instrument 1140 configured to operate on the right femur.

The strike plate 1146 may contain beveled surfaces 1156, which can be similar to an accomplished function of beveled surfaces 56 of instrument 140 of the first embodiment.

FIGS. 48A-F show an instrument assembly 1240 that is conceptually similar in some ways to instrument 40 described above, in that it provides both anterior and lateral offsets to the handle axis relative to a shaping member axis. However, the instrument assembly 1240 shown in FIGS. 48A-F utilizes two connection structures such as two corresponding posts 1274, 1276 on the shaping member 1242, and only one corresponding connection structure such as a receiving recess on a distal portion of the instrument 1240. The connection structures 1274, 1276 provided on the shaping member 1242 may be angled with respect to the shaping member axis and handle axis so as to effectively provide an anterior and lateral offset of the handle 1244 relative to the shaping member 1274 when assembled and positioned for use on a patient. As shown in FIGS. 48A-F, the shaping members 1242 provide an anterior and lateral offset of the handle 1244 relative to the shaping member 1274 when used with symmetrical handles 1244 having a single offset 1248.

Figure 48A:
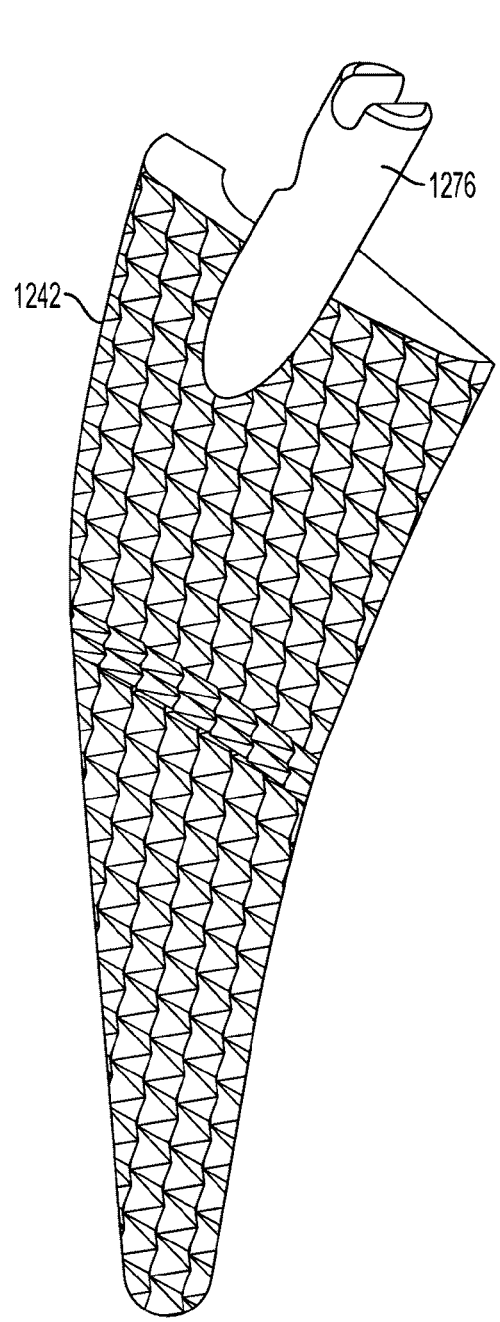
FIG. 48A shows a side view of another version of a shaping member.
Figure 48B:
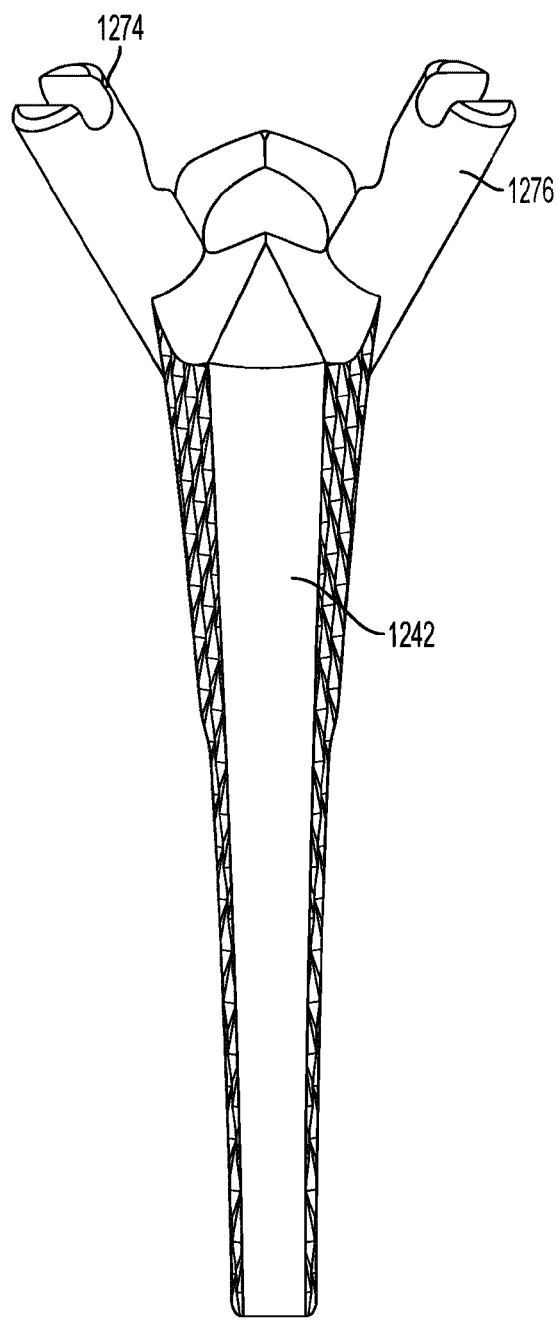
FIG. 48B shows a frontal view of the shaping member of FIG. 48A.
Figures 48C, 48D:
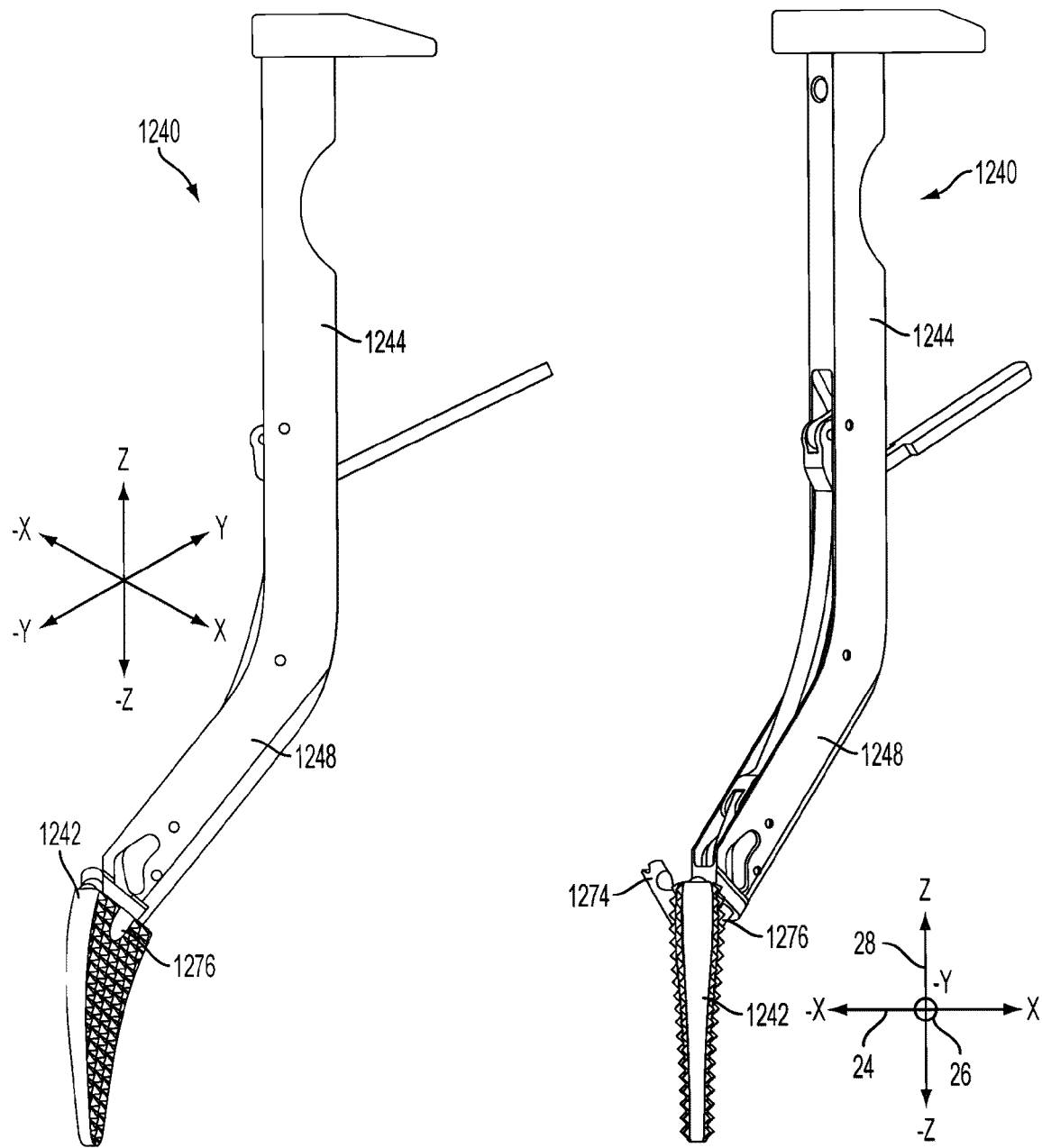
FIG. 48C shows a twelfth embodiment of an instrument assembly according to the present invention, the instrument including the shaping member of FIG. 48A positioned for operating on the right femur.
FIG. 48D shows a posterior perspective view of the instrument assembly of FIG. 48C.
Figure 48E:
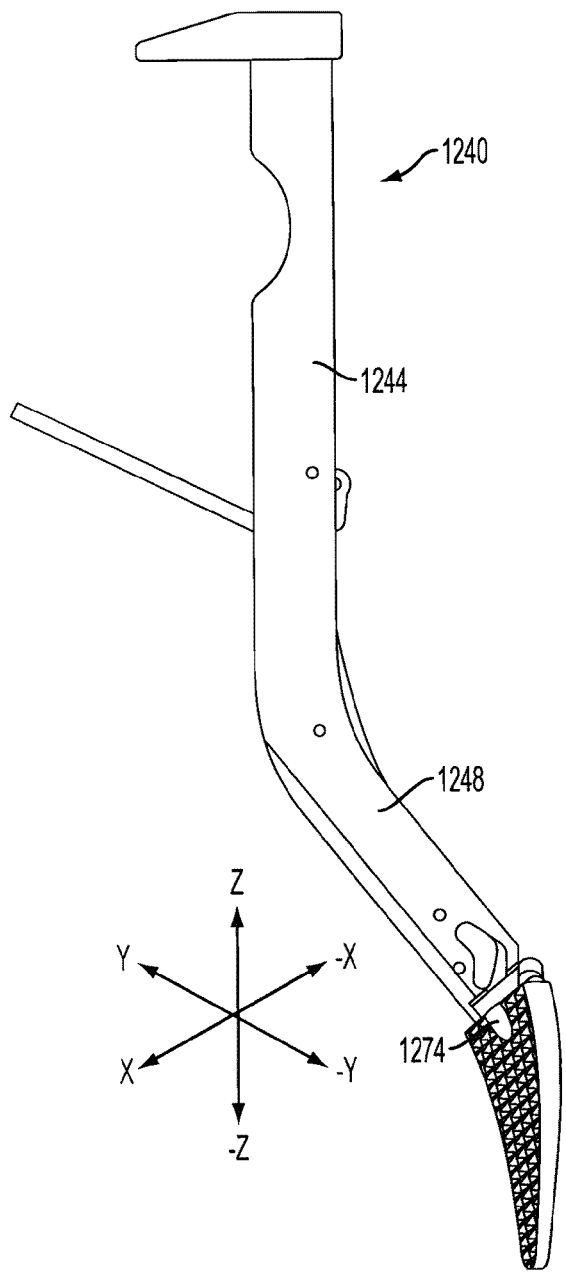
FIG. 48E shows another perspective view of the instrument assembly of FIG. 48C, the instrument assembly including the shaping member of FIG. 48A positioned for operating on the left femur.
Figure 48F:
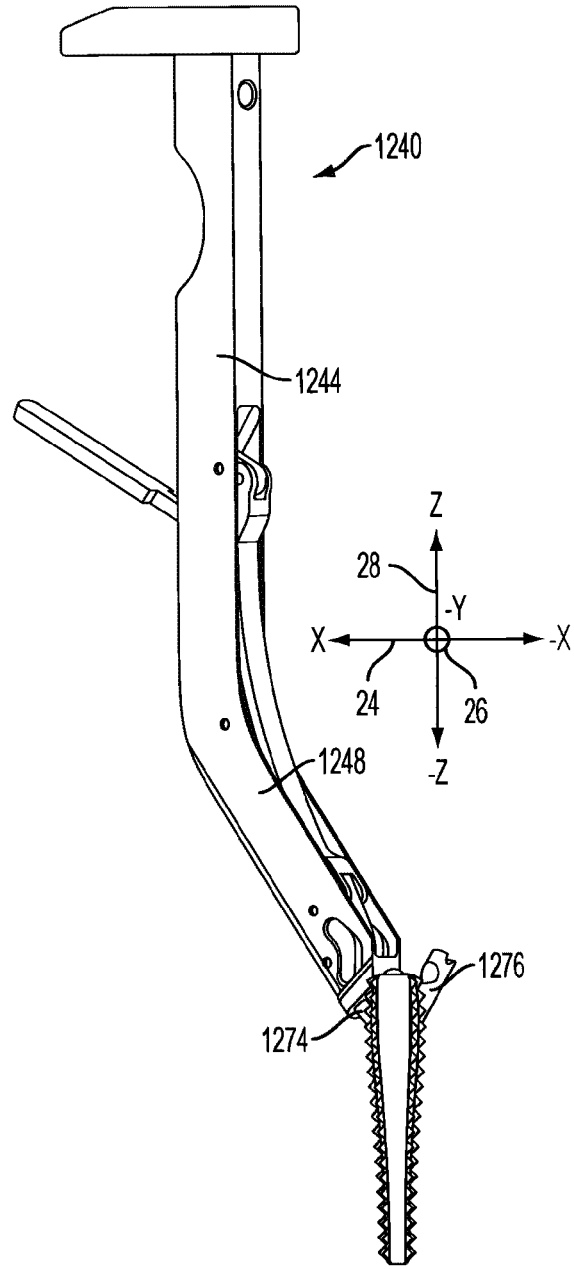
FIG. 48F shows a posterior perspective view of the instrument assembly of FIG. 48E.

Instrument assembly 1240 includes a handle 1244 and a shaping member 1242 having two posts 1274 and 1276 adapted to interface with offset 1248 to connect shaping member 1242 to the distal end of offset 1248. As shown in FIGS. 48C-D, post 1276 of shaping member 1242 connects to the distal end of offset 1248 for operation on the right femur. As shown in FIGS. 48E-F, post 1274 of shaping member 1242 attaches to the distal end of offset 1248 instead of post 1276 for operation on the left femur. In the embodiment shown in FIGS. 48A-F, offset 1248 comprises only a single offset with respect to the handle 1244.

FIGS. 49A-C show an instrument 1340 having handle 1344, optionally-chamfered strike plate 1346, offset 1348, and shaping member 1342. Shaping member 1342 includes a protrusion 1374 configured to be received within either a first receiving geometry or a second receiving geometry, 1290 and 1292 respectively, in the distal end of offset 1348, depending on whether the instrument is used to operate on the right or the left femur. As shown in FIG. 49A, the instrument 1340 is positioned so that protrusion 1374 of shaping member 1342 is aligned with the first receiving geometry 1290 of the distal end of offset 1348 for operation on the left femur. FIGS. 49B-C show the positioning of instrument 1340 for operation on the right femur, so that the protrusion 1374 of the shaping member 1342 is aligned with the second receiving geometry 1292 of the distal end of offset 1348. Any desired structure can be used to retain the shaping member 1342 in the respective desired receiving geometry 1290, 1292.

Figures 50A, 50B:
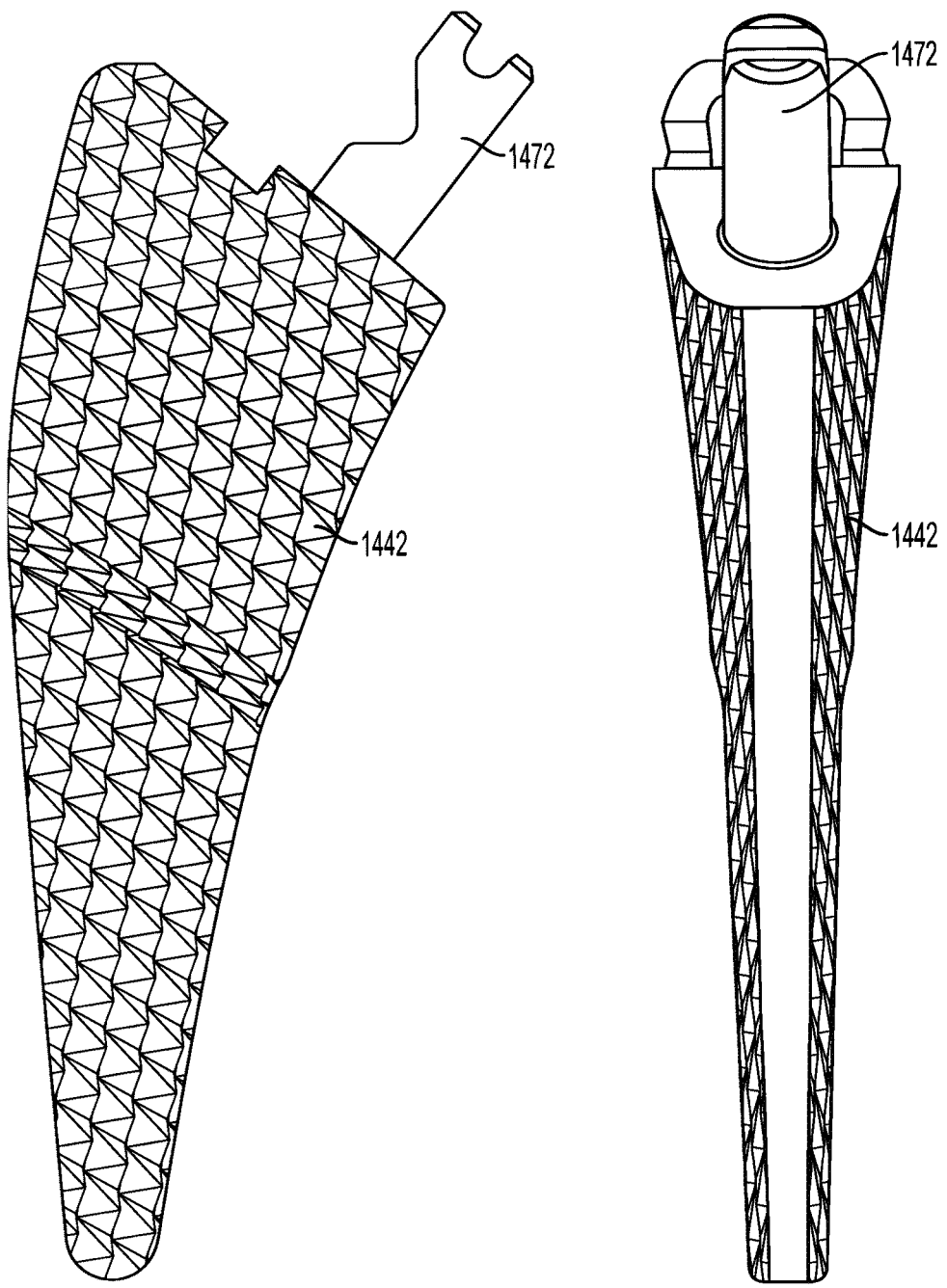
FIG. 50A shows a side view of another version of a shaping member.
FIG. 50B shows a frontal plane view of the shaping member of FIG. 50A.
Figure 50C:
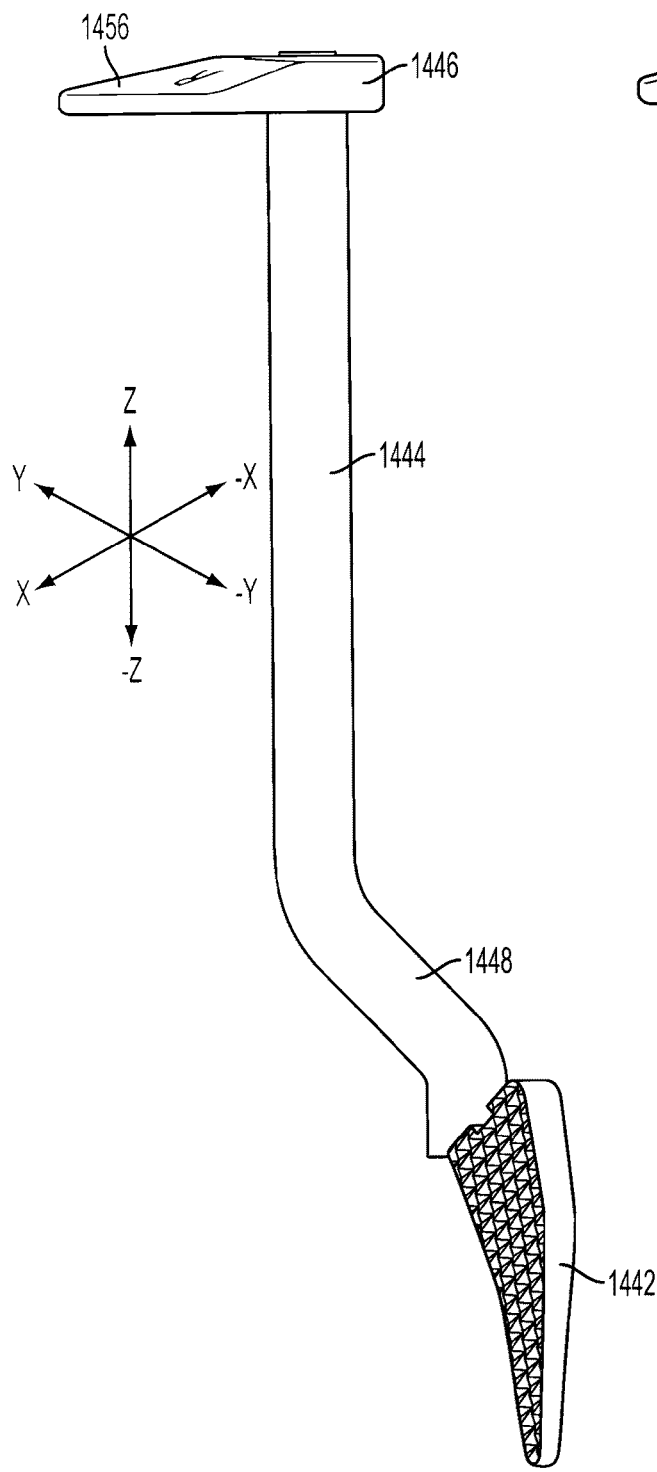
FIG. 50C shows a fourteenth embodiment of an instrument according to the present invention, the instrument including the shaping member of FIG. 50A and positioned for operating on the left femur.
Figure 50D:
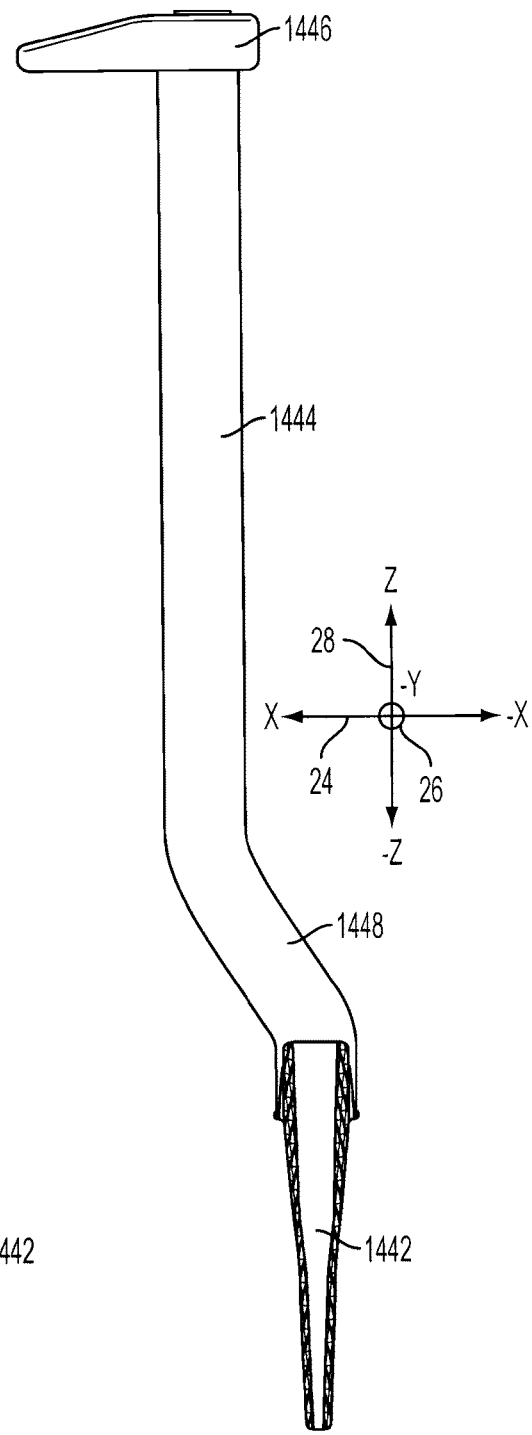
FIG. 50D shows a posterior perspective view of the instrument of FIG. 50C.
Figure 50E:
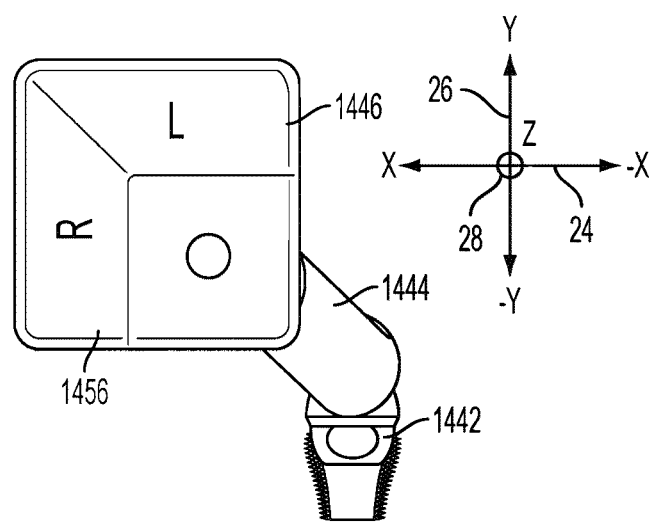
FIG. 50E shows an elevated view of the instrument of FIG. 50C.
Figure 50H:
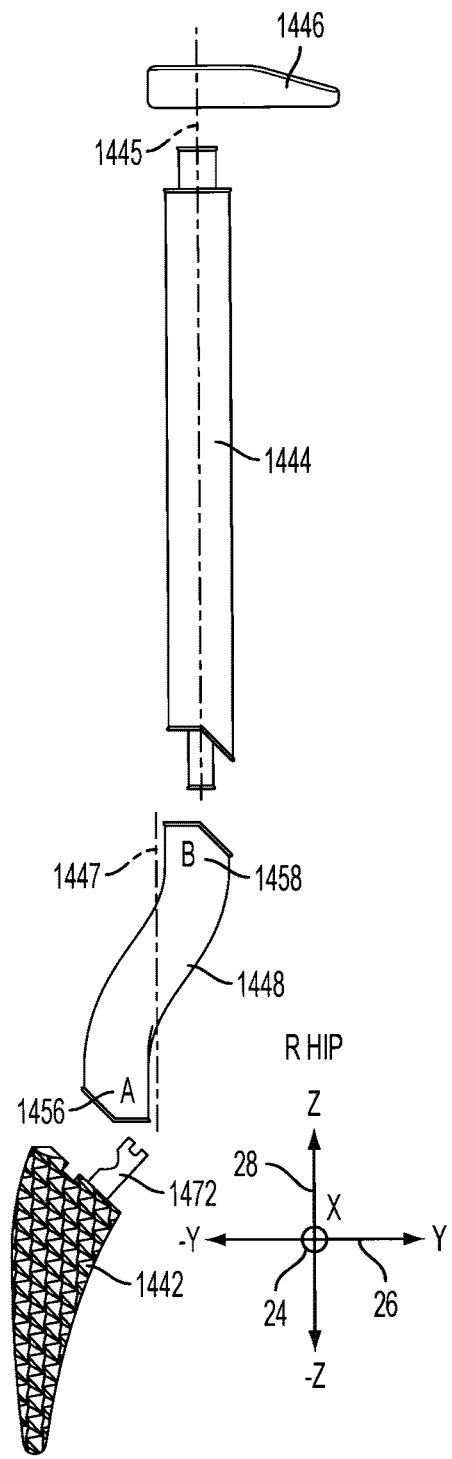
FIG. 50H shows an alternate view of the instrument of FIG. 50G after the offset component has been rotated for use with a right femur.
Figure 50I:
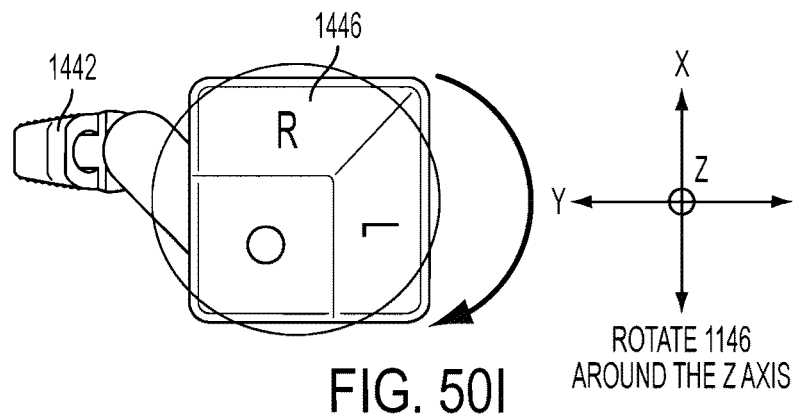
FIG. 50I shows an elevated perspective view of the instrument of FIG. 50H before the strike plate is rotated for use with a right femur.
Figure 50J:
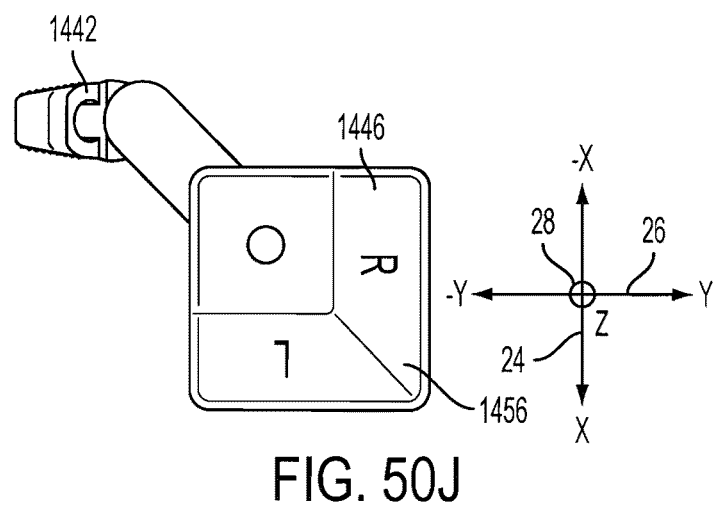
FIG. 50J shows another elevated perspective view of the instrument of FIG. 50I after the strike plate is rotated for operating on a right femur.
Figures 50K, 50L:
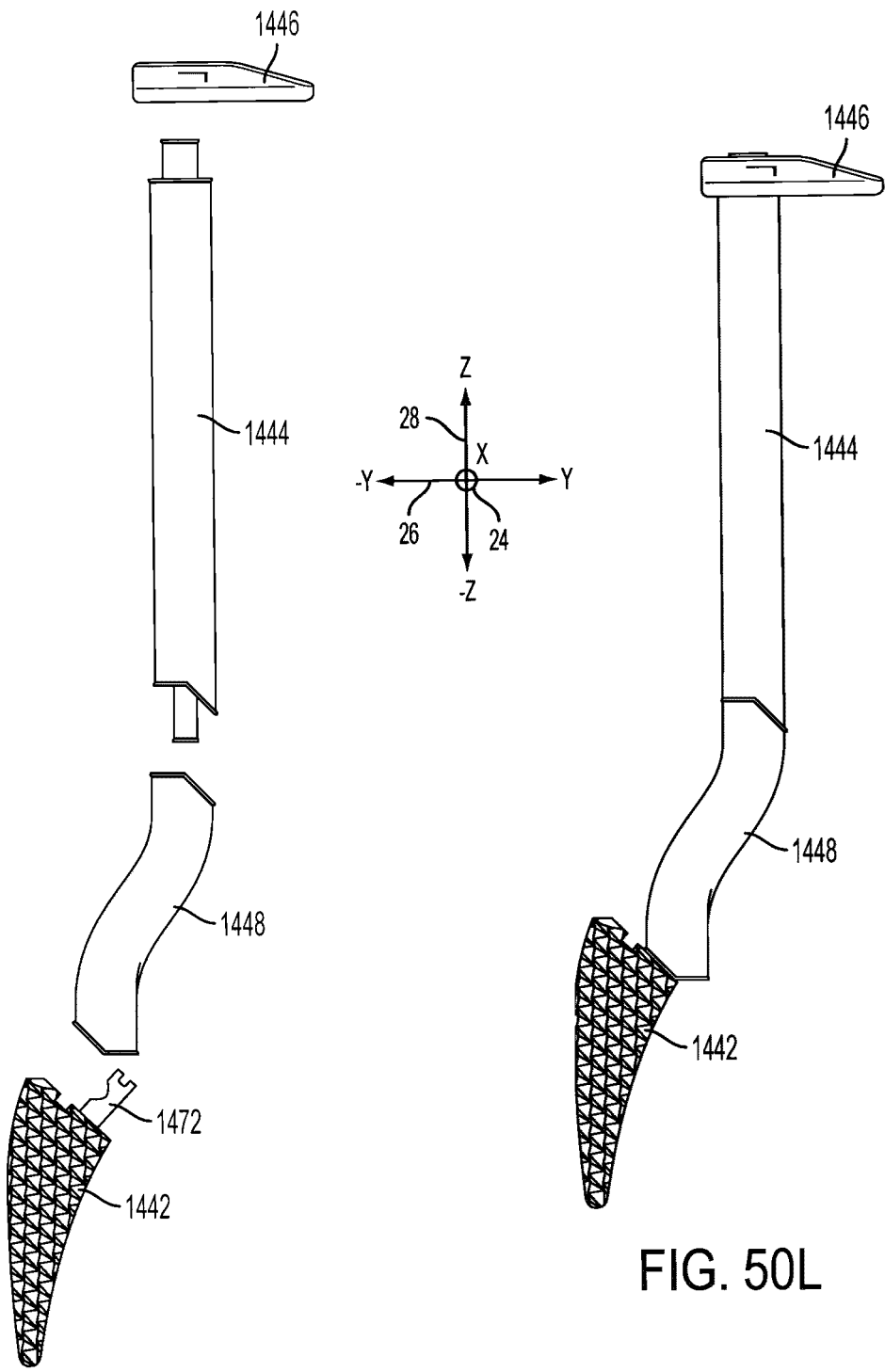
FIG. 50K shows an exploded view of the instrument of FIG. 50J from a lateral perspective.
FIG. 50L shows a lateral perspective view of the assembled instrument of FIG. 50K.
Figure 50M:
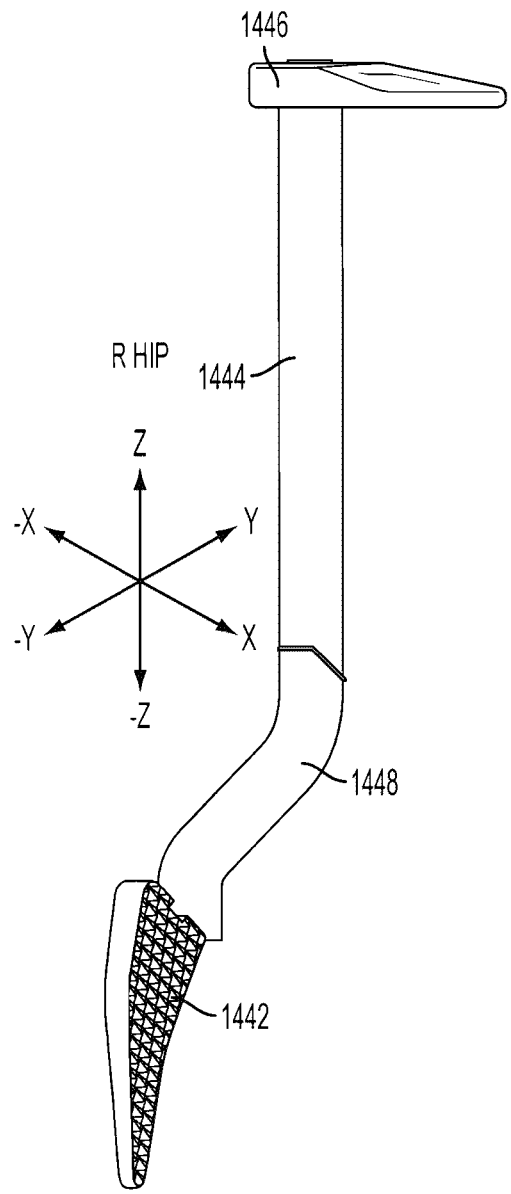
FIG. 50M shows another perspective view of the instrument of FIG. 50L, which is configured for operating on a right femur.
Figure 50N:
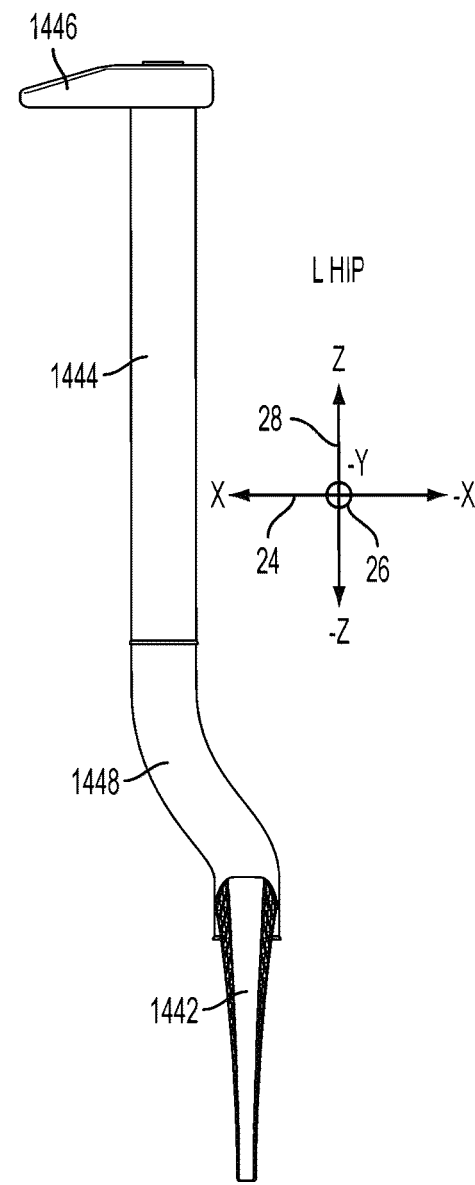
FIG. 50N shows another posterior view of the instrument of FIG. 50F assembled together.
Figure 50O:
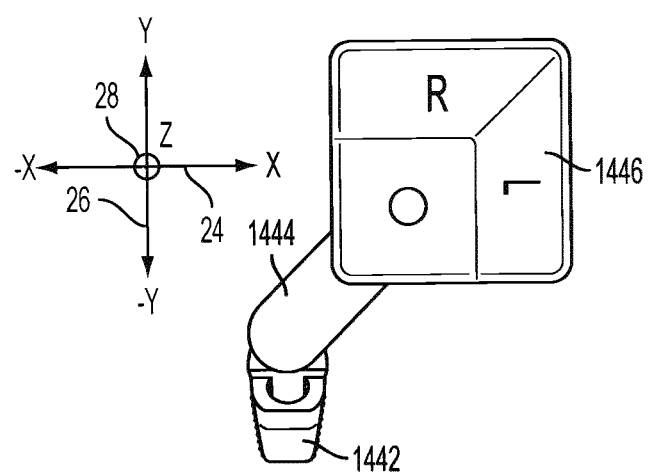
FIG. 50O shows an elevated view of the instrument of FIGS. 50J-M.

FIG. 50A-O shows a modular instrument 1440 according to another version of multiconfigurable instruments according to the present invention. In this embodiment, instrument 1440 includes a strike plate 1446, handle 1444, offset 1448, and shaping member 1442. Shaping member 1442 includes a post 1472 that is angled to be received within a corresponding opening 1441 in the distal end of offset 1448. As shown in FIGS. 50E-H, instrument 1440 is modular with respect to strike plate 1446 and handle 1444, with respect to handle 1444 and offset 1448, and with respect to offset 1448 and shaping member 1442. Offset 1448 includes an "A" end and a "B" end, 1456 and 1458 respectively, as shown in FIGS. 49F-H. When a first femur is the subject of surgery, one of the A and B ends of offset 1448 connects to shaping member 1442 and the other of the A and B ends of offset 1448 connects to handle 1444. FIGS. 50C-G show views of an instrument configured to operate on a left femur. When the right femur is the subject of surgery, offset 1448 is rotated 180 degrees about the X-axis, as shown in FIGS. 50G-H so that the other end of offset member 1448 connects to shaping member 1442 and the opposite end connects to handle 1444. To accommodate the other femur, the strike plate 1446 is also rotated around the Z-axis as shown in FIGS. 50I and 50J. FIGS. 50J-O show various views of the instrument 1440 configured to operate on the right femur.

The strike plate 1446 may contain beveled surfaces 1456, which can be similar to an accomplished function of beveled surfaces 56 of instrument 40 of the first embodiment.

FIGS. 51A-D show another mechanism for connecting a shaping member 1542 having an opening 1550 to posts 1574 of distal end of an offset member 1548, such as one described above. As shown in FIG. 51A-2, opening 1550 can have any suitable cross section, including but not limited to circular, oval, triangular, or rectangular. Post 1574 includes a projection 1572 that can be received within a locking recess 1548 of the shaping member 1542 (shown in FIG. 51D). When post 1574 is inserted into opening 1550, springs 1520 in the offset member 1548 cause projection 1572 to pivot about pivot 1560 until the projection 1572 is captured within recess 1548 to retain the shaping member 1542 to the offset member 1548.

Figures 1, 52A:
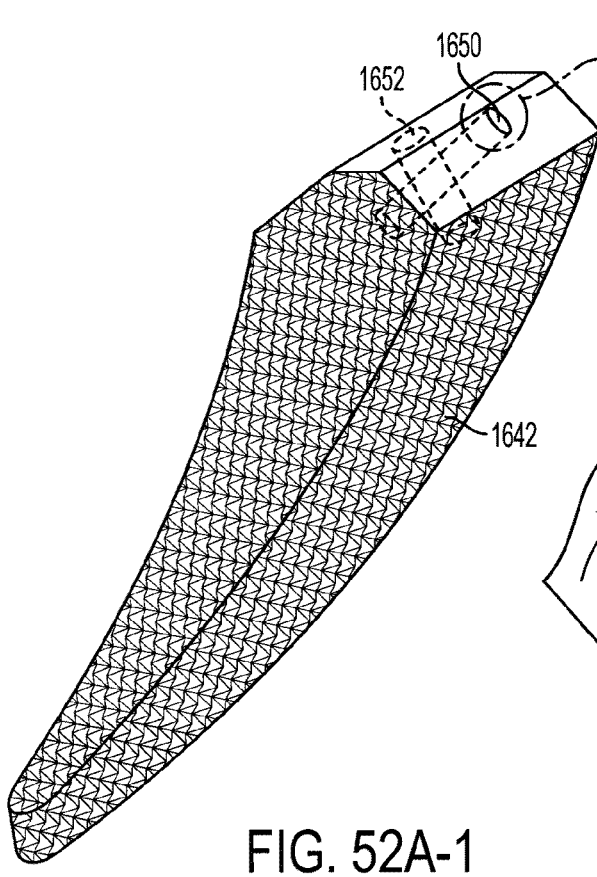
Figures 2, 52A:
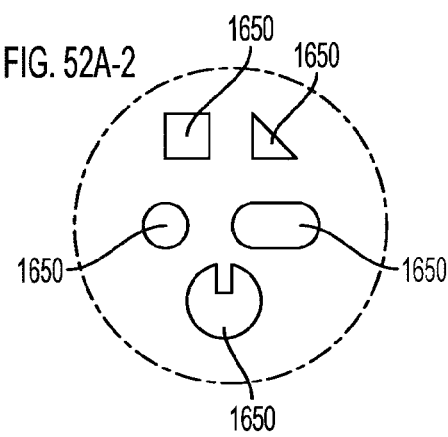
Figure 52B:
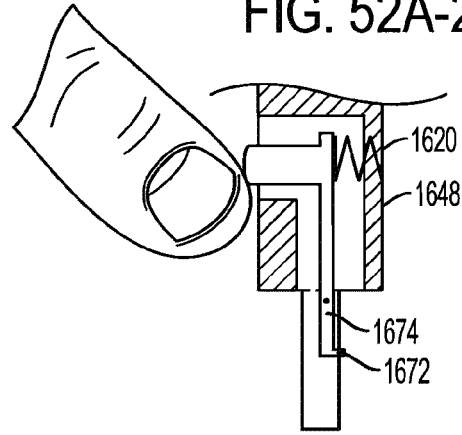
FIG. 52B shows the distal end of an instrument according to another embodiment of the present invention.
Figure 52C:
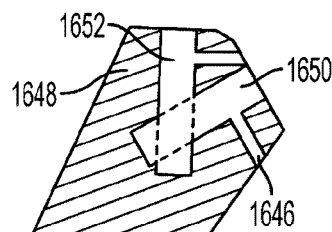
FIGS. 52C and 52D show cross-sectional views of the shaping member of FIG. 52A positioned for operating on left and right femurs, respectively.
Figure 52D:
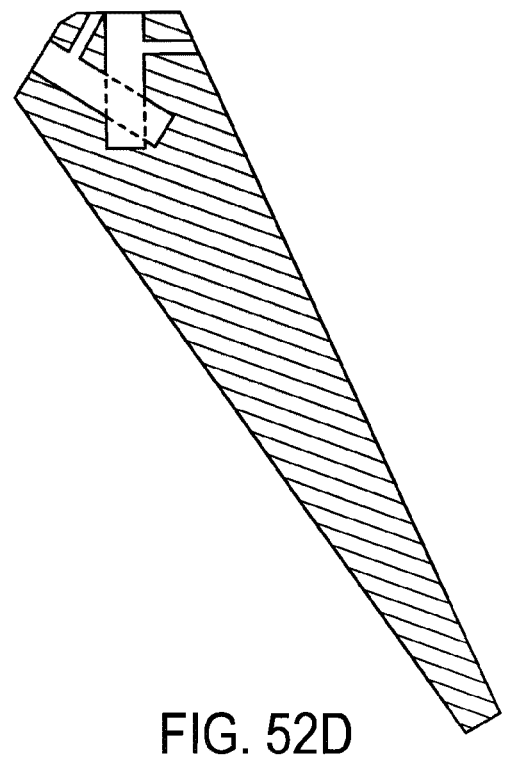

FIGS. 52A-D show another mechanism for connecting a shaping instrument 1642 having two openings 1650 and 1652 to a post 1674 of distal end of an offset member 1648 such as one described above. Openings 1650 and 1652 can have any suitable cross section, including but not limited to circular, oval, triangular, or rectangular as shown in FIG. 52A-2. Post 1674 includes a projection 1672 that can be received within either locking recess 1646 or 1648, depending on which opening post 1674 is received within (shown in FIG. 52 C-D). When post 1674 is inserted into one of the openings 1650 or 1652, a spring 1620 causes projection 1672 to pivot until projection 1674 is received within the appropriate recess 1646 or 1648. Spring 1620 may be provided as compression spring (as shown), a torsion spring, tension spring, or a leaf spring separate or integrally formed with any of the above.

Figure 53A:
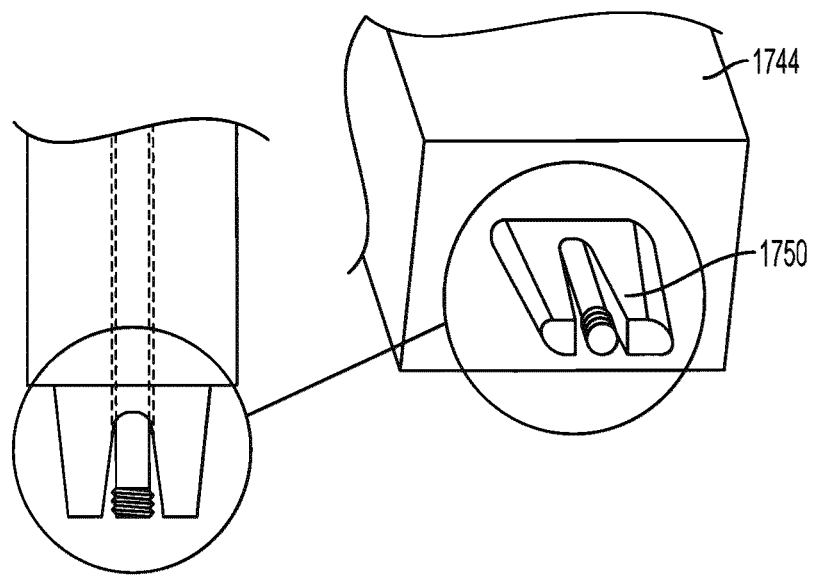
FIG. 53A shows the distal portion of an instrument according to another embodiment of the present invention.
Figures 53B, 53C:
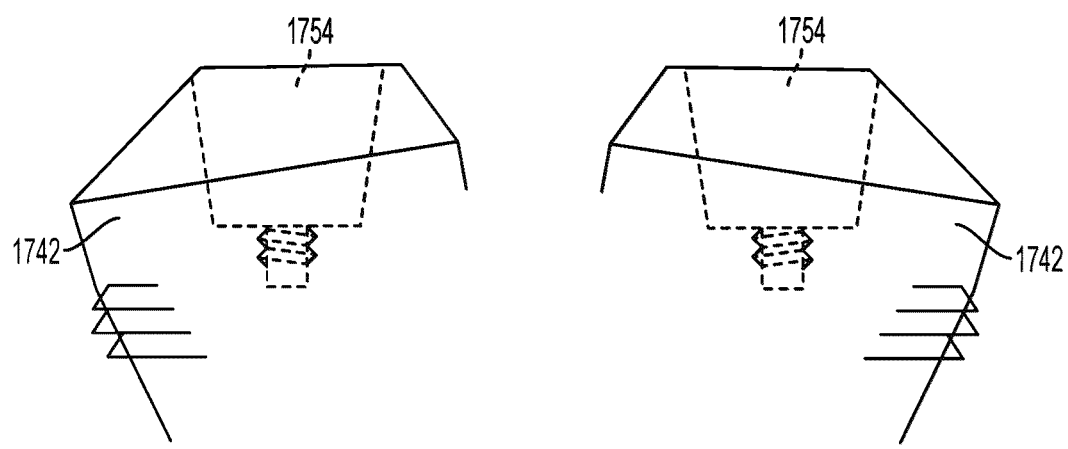
FIG. 53B shows a shaping member according to another embodiment of the present invention positioned for operating on left femur.
FIG. 53C shows a shaping member of FIG. 53B after it has been rotated 180 degrees for operating on right femur.

FIG. 53A shows a distal portion of a handle 1744 having a protrusion 1750. FIGS. 53B-C show a shaping member 1742 having a recess 1754 configured to receive protrusion 1750 of handle 1744 via a taper-locking connection such as a Morse taper. Recess 1754 and protrusion may have any suitable configuration, such as frustroconical or tapered with an oval cross-section. The instrumentation shown in FIGS. 53A-C is particularly useful if modular necks are used in conjunction with the shaping member in situ during trial reduction. Recess 1754 may be symmetrical as shown in FIGS. 53B-C, and the shaping member 1742 may be inserted into either a right or left femur and be able to receive modular trial necks for trialing a left or right implant. Moreover, if recess 1754 is symmetrical as shown in FIGS. 53B-C, then the position of the shaping member 1742 with respect to the handle 1744 may be rotated 180 degrees to accommodate left and right hips. Means for breaking a taper connection between the handle 1744 and the shaping member 1742 may also be provided (not shown). Such means may be, for instance, a spring-loaded plunger that creates an impact force to the taper connection. Moreover, means for removing the shaping member 1742 from the surgical site (e.g., intramedullary canal) may be provided to the offset 1744. Such means may be, for example, provided by a screw 1750(*b*) located on the handle 1744 which engages a thread hole 1754(*b*) in the shaping member 1742.

Figures 54A, 55A:
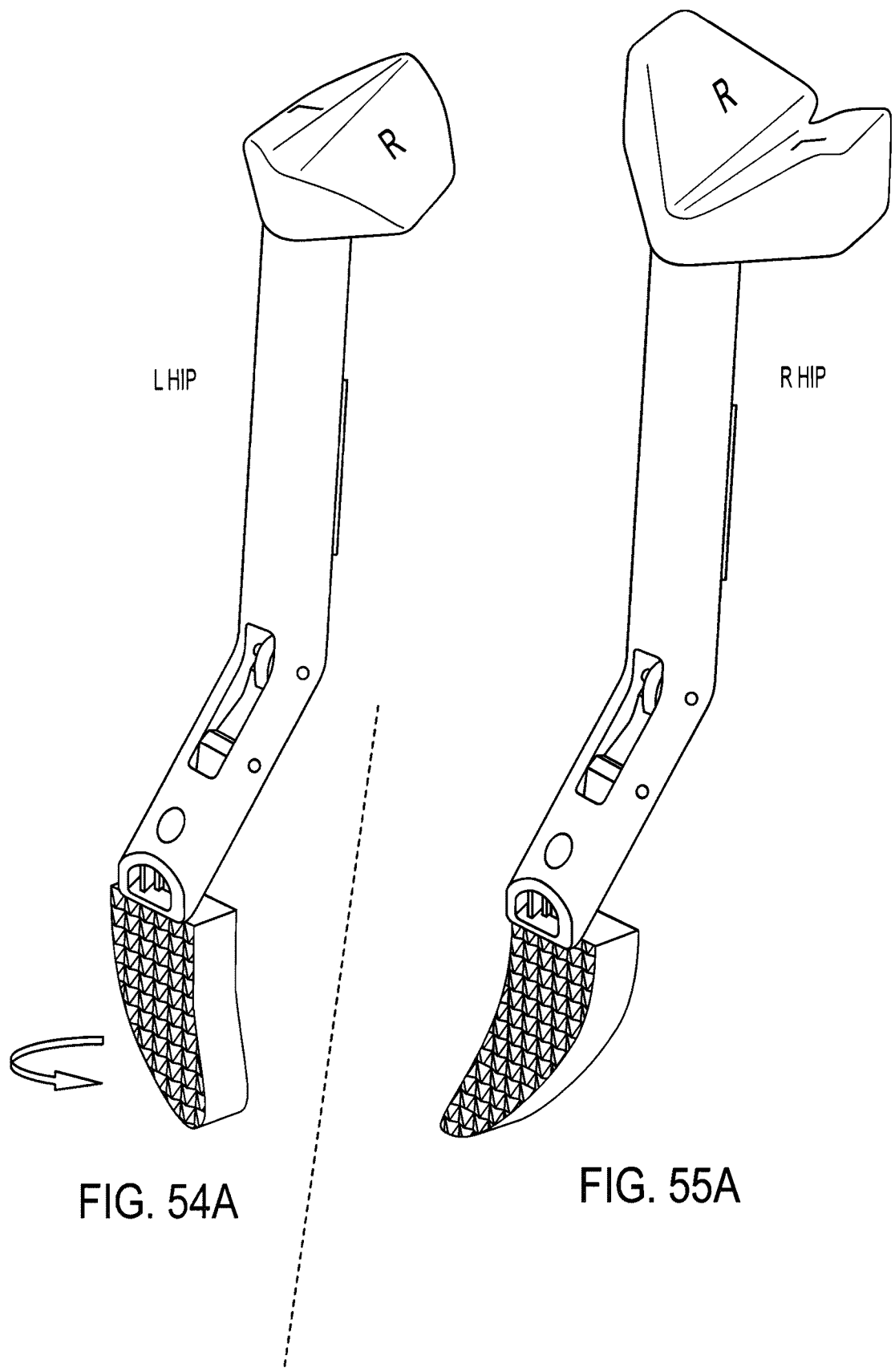
FIG. 54A shows an instrument assembly according to a fifteenth embodiment of the present invention configured for operating on a left femur.
FIG. 55A shows an instrument assembly according to a sixteenth embodiment of the present invention configured for operating on a right femur.
Figure 54B:
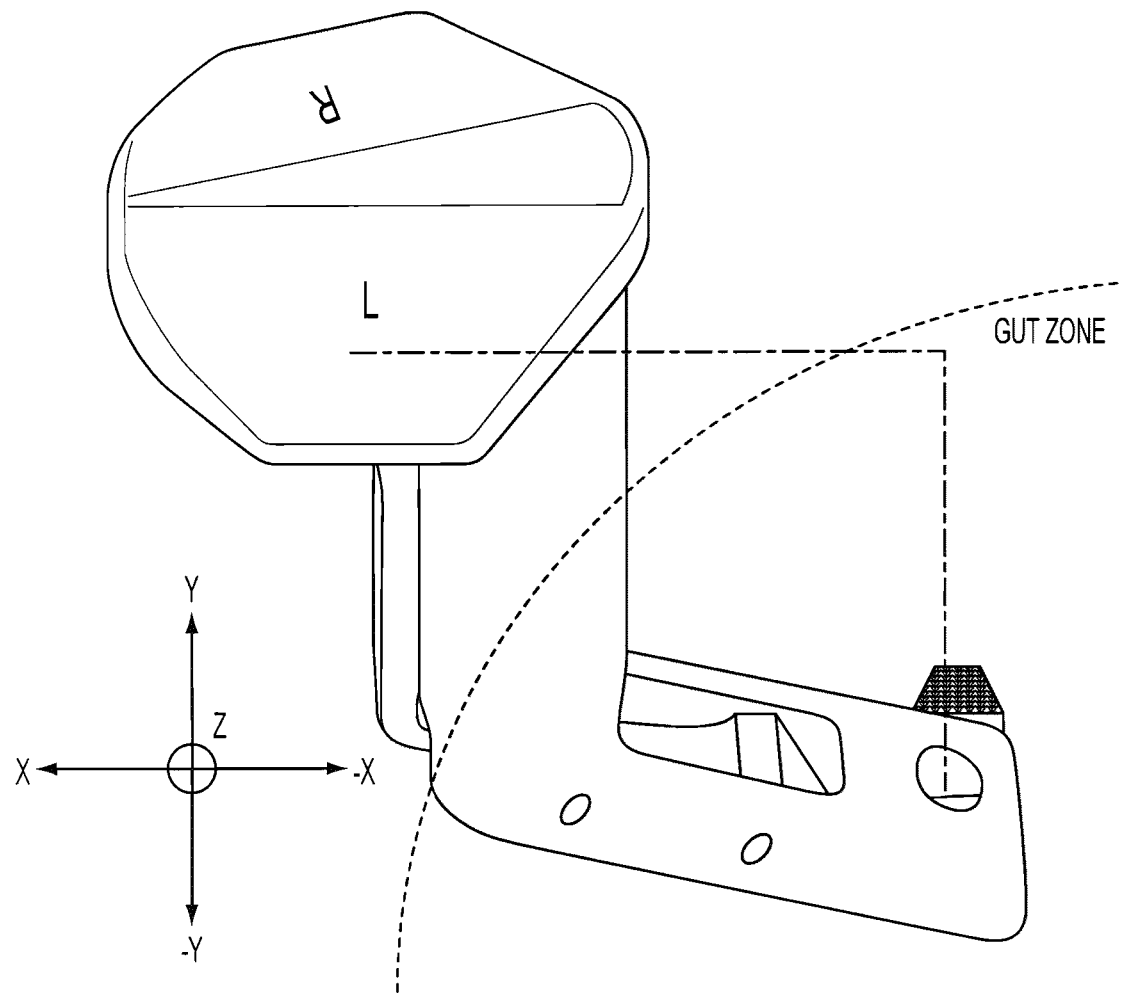
FIG. 54B shows a superior view of the assembly shown in FIG. 54A in use.

FIG. 54A shows an instrument assembly 1840 according to a fifteenth embodiment of the present invention configured for operating on a left femur. FIG. 54B shows a superior view of the assembly shown in FIG. 54A in use relative to a patient's left hip. It can be seen from FIG. 54B that the handle 1844 may comprise a linkage mechanism to secure an insertion member 1842 to a distal end of an offset 1848. The assembly 1840 provides both a lateral offset and anterior offset of the strike plate 1846 surface relative to the insertion member 1842. A normal to the strike plate 1846 surface used is generally parallel to the axis of the insertion member 1842. Shown in FIG. 54B, the axis 1868 of the insertion member 1842 and the normal to the "Left" surface of the strike plate 1846 are generally parallel to the Z-axis. However, in this embodiment, both the handle axis 1854 and offset 1848 are not generally parallel with the axis 1868 of the insertion member 1842.

Figure 55B:
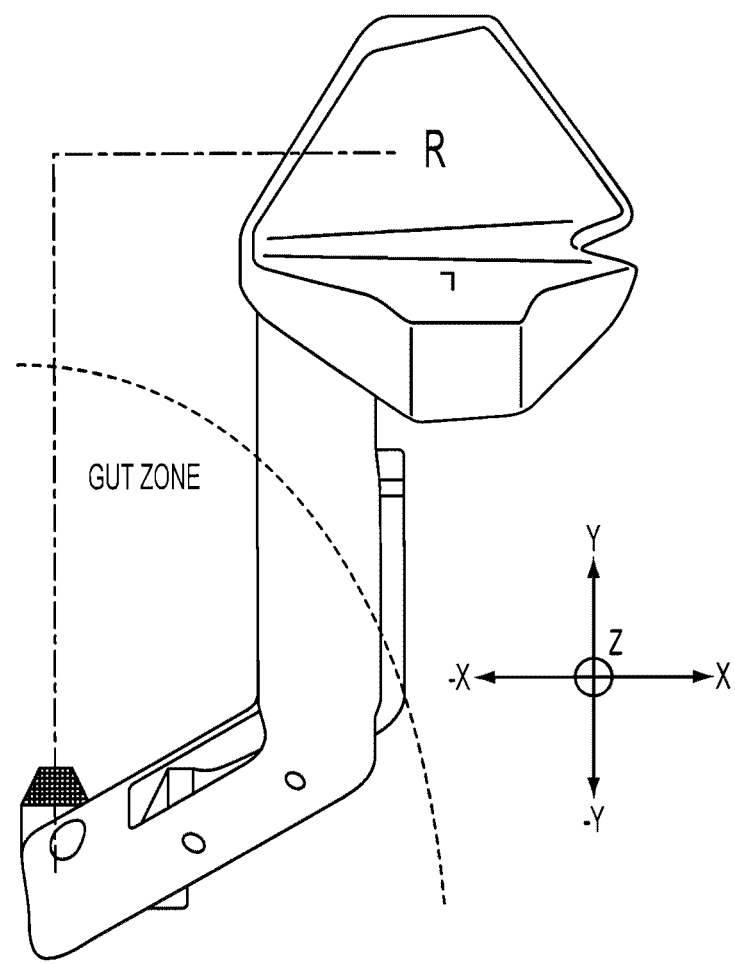
FIG. 55B shows a superior view of the assembly shown in FIG. 55A in use.

FIG. 55A shows an instrument assembly 1940 according to a sixteenth embodiment of the present invention configured for operating on a right femur. The instrument assembly 1940 shows an alternative embodiment of a strike plate 1946 having a V-shaped profile. FIG. 55B shows a superior view of the assembly shown in FIG. 55A in use. It can be seen from FIG. 55B that the handle 1944 may comprise a linkage mechanism to secure an insertion member 1942 to a distal end of an offset 1948. The assembly 1940 provides both a lateral offset and anterior offset of the strike plate 1946 relative to the insertion member 1942. A normal to the "Right" strike plate 1946 surface used is generally parallel to the axis 1968 of the insertion member 1942 and to the Z-axis. However, as with the embodiment shown in FIGS. 54A and 54B, the handle axis 1954 and the axis 1958 of the offset 1948 are generally not parallel with the axis 1968 of the insertion member 1942.

Figures 56A, 56B:
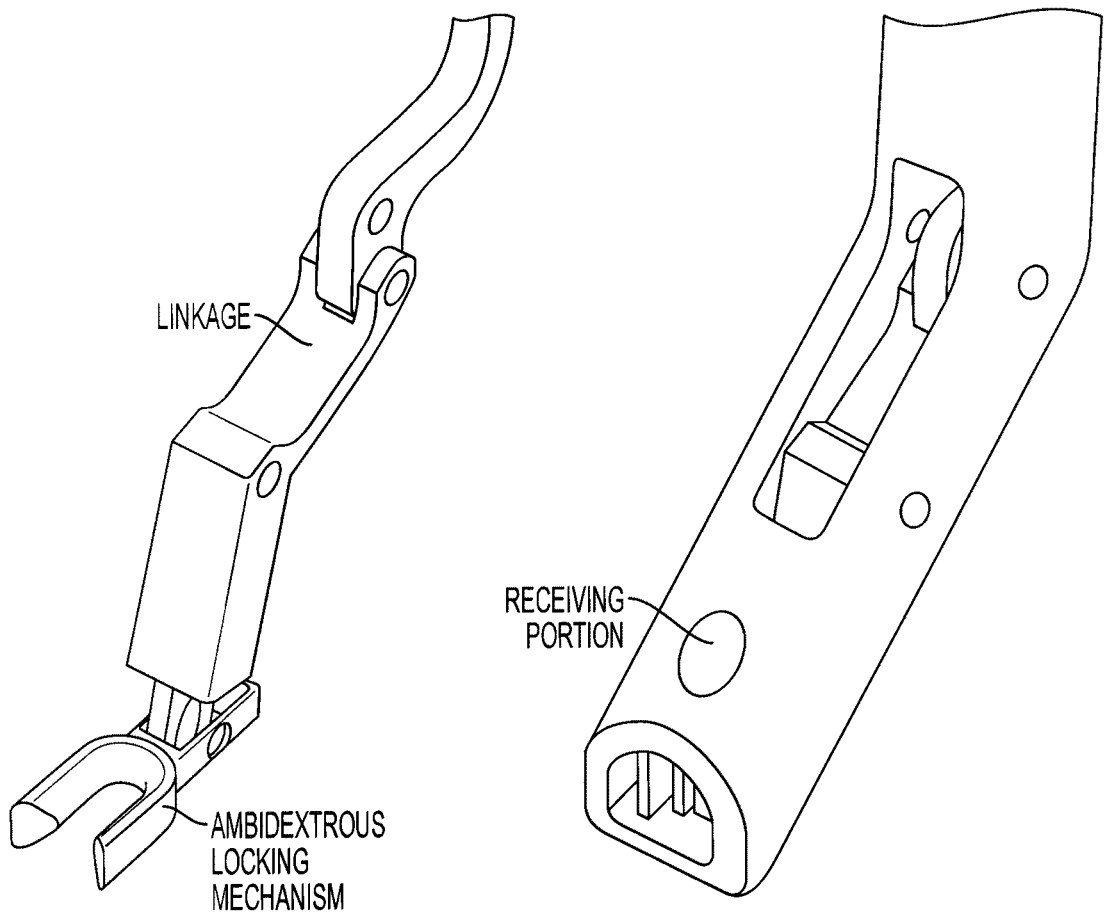
FIGS. 56A and 56B show a locking mechanism for a shaping member according to some embodiments.
Figure 57F:
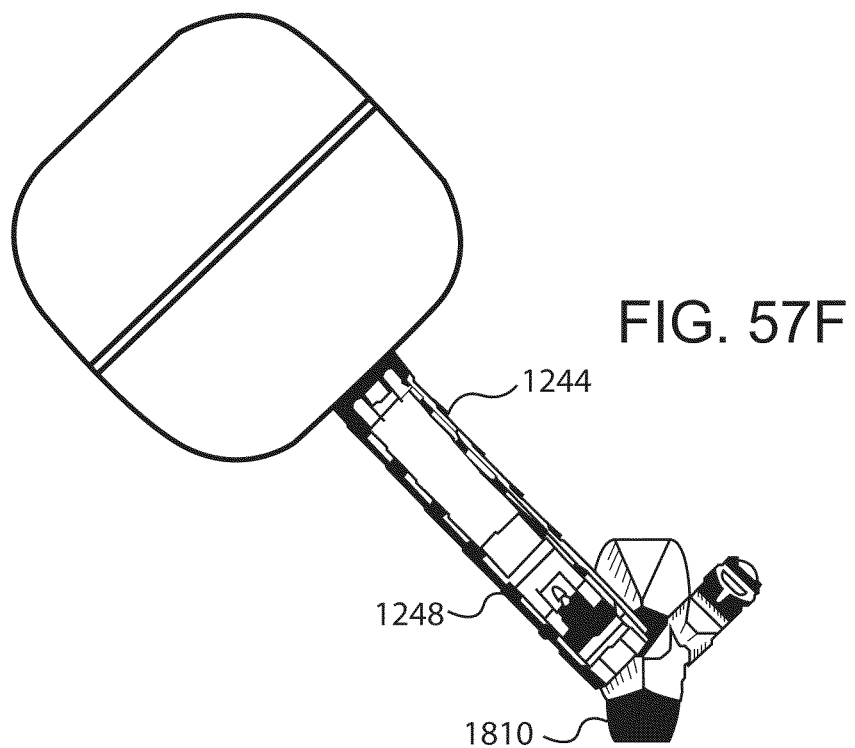
FIG. 57F shows the assembly of FIG. 57E, alternatively configured for use on a left femur.
Figure 57G:
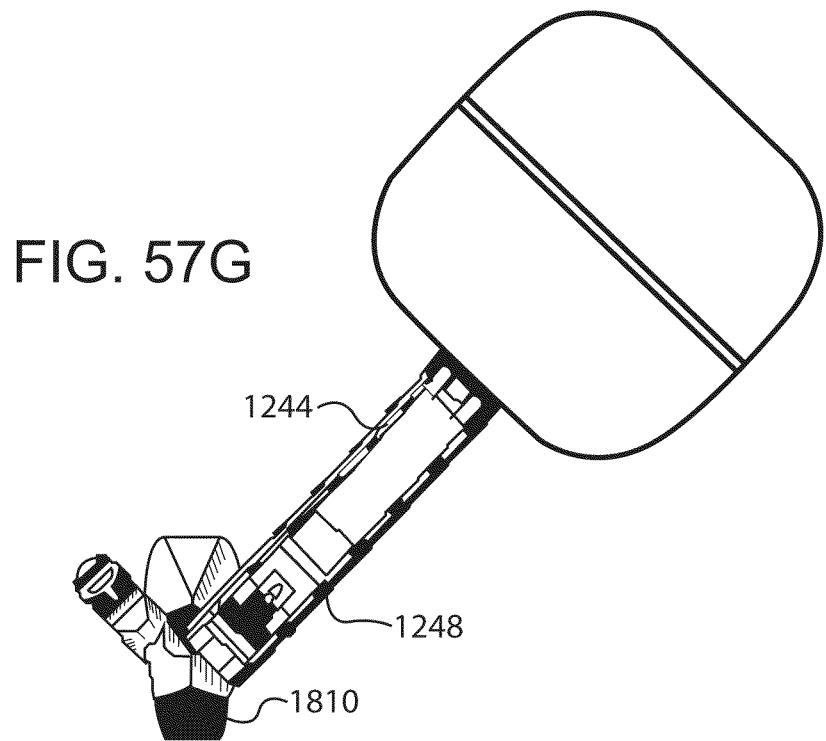
FIG. 57G is a top view of the assembly shown in FIG. 57E, configured for use on a right femur.

FIGS. 56A and 56B show a locking mechanism for an insertion member according to some embodiments. In the embodiment shown, an ambidextrous fork-shaped yoke slides transversely across a receiving portion configured to receive a post portion of an insertion member (e.g., a broach post). A moveable linkage controls the transverse movement of the yoke to either lock or unlock the insertion member to the handle. Locking may be facilitated by a separate leaf spring or a link which is designed with an integral leaf spring. Yoke fingers may be prismatic and have a cross-section that is generally triangular in order to compliment the notches typically provided on conventional insertion member post portions.

FIGS. 57A-57G illustrate an adapter 1810 that provides a dual offset when assembled with a conventional single offset handle and conventional insertion member 1442 (e.g., broach) used for operating on a patient's medullary canal. In some embodiments, the adapter 1810 includes a body 1812 and a recess 2002 for receiving post 1472 of insertion member 1442. In other embodiments, the adapter 2000 has a protrusion for insertion into a cavity of a conventional post-less insertion member (not shown).

As shown in FIG. 57D, the adapter 1810 in some embodiments includes two posts 2072 and 2074 that are configured to connect with a receiving portion of a conventional handle used for operating on a patient's medullary canal. Post 2072 connects to the handle when operating on the right femur, and post 2074 connects to the handle when operating on the left femur.

In use, as shown in FIG. 57C, adapter 1810 is secured to insertion member 1442 using, for example, set screw 2010 (FIG. 57A) or any other suitable means of connection. Other means of connection include, but are not limited to, clamps, cams, spring-loaded pins, and/or latches. The axes of the handle 1244 and insertion member 2042 are as described above. The adapter is configured to fit with a customary handle (such as handle 1244 shown in FIG. 57E) and a customary insertion member (such as broach 1442). The alignment and angulation of the post 2072 of adapter 1810 relative to the cavity 2002 achieves the dual offset between the handle and the insertion member detailed above. Thus, depending on which leg is being operated, a surgeon may connect the respective post 2072 or 2074 of the adapter 1810 to the conventional single offset handle. Use of adapter 1810 offsets the axis of the handle 1244 both anteriorly and laterally from the axis of the insertion member 1442. As described in detail above, this anterior and lateral offset provides a clearance of the handle with respect to the patient's gut zone and other musculature.

Figures 58A, 59A:
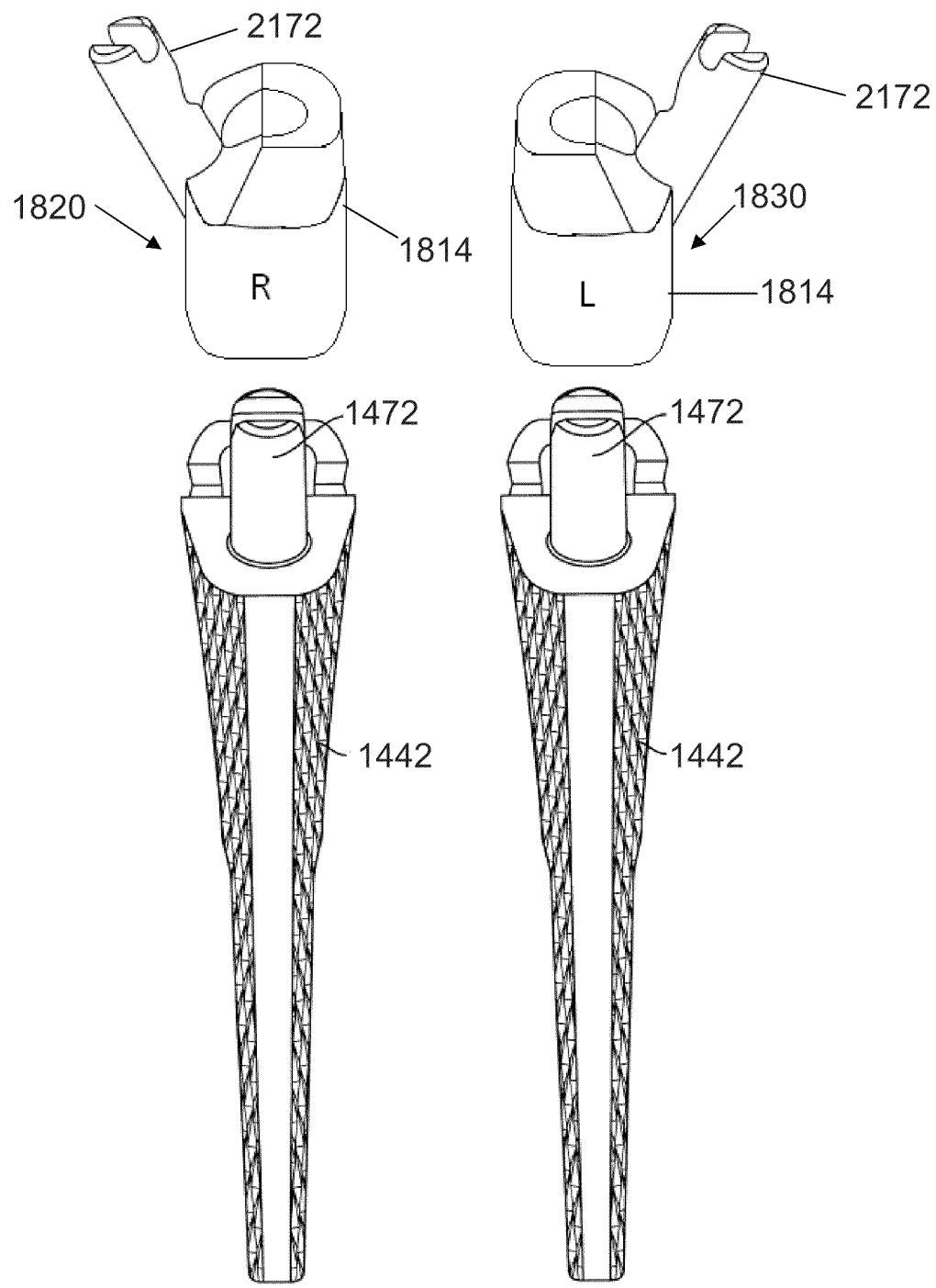
FIG. 58A shows an adapter according to another embodiment of the present invention configured for operating on a right femur.
FIG. 59A shows an adapter according to yet another embodiment of the present invention configured for operating on a left femur.

FIGS. 58A and 59A illustrate alternate adapters 1820 and 1830. Like adapter 1810, adapters 1820 and 1830 may be used with a conventional single offset handle (such as handle 1244 shown in FIG. 59B) and conventional insertion member (such as broach 1442) for operating on a patient's medullary canal to achieve the dual offset described above. Adapters 1820 and 1830 may include a body 1814 and a recess for receiving post 1472 of a conventional insertion member 1442. Alternatively, in certain embodiments, adapters 1820 and 1830 may include a protrusion for insertion into the cavity of a post-less insertion member (not shown).

Figures 58B, 58C:
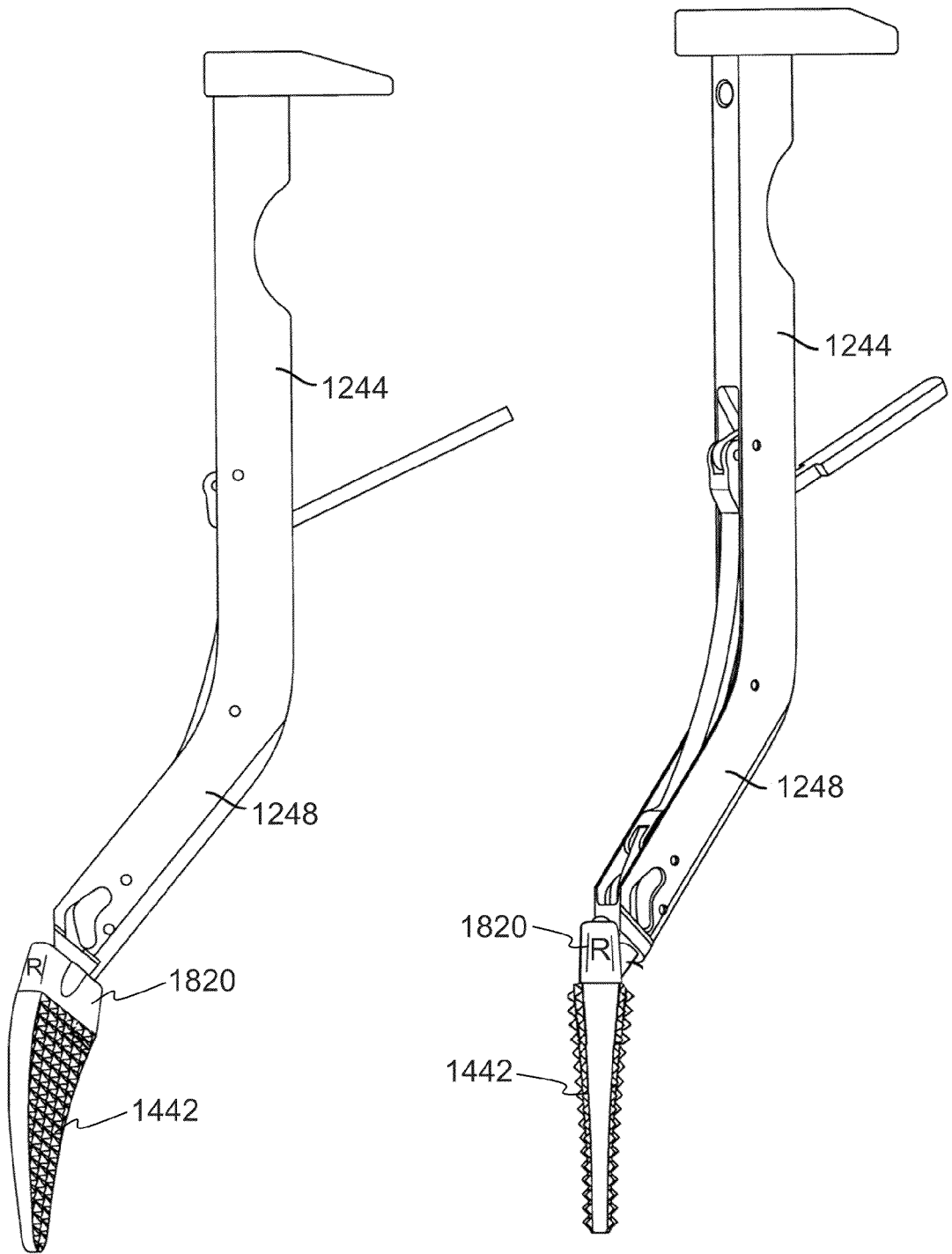
FIGS. 58B-C show various view of the adapter of FIG. 58A connected to a handle and a shaping member.

In some embodiments, adapters 1820 and 1830 include a single angled post 2172 that is configured to connect with a receiving portion of a conventional single offset handle used for operating on a patient's medullary canal, as shown in FIGS. 58B-C and FIG. 59B.

Adapter 1820 illustrated in FIG. 58A is configured for use when operating on a right femur, and adapter 1830 illustrated in FIG. 59B is configured for use when operating on a left femur. In use, either adapter 1820 or 1830 is secured to insertion member 1442 using, for example, a set screw as described above or any other suitable means of connection. Other means of connection include, but are not limited to, clamps, cams, spring-loaded pins, and/or latches.

Adapters 1820 and 1830 are configured to fit with a customary handle (such as handle 1244 shown in FIGS. 58B-C and FIG. 59B) and a customary insertion member (such as broach 1442). The alignment and angulation of the post 2172 of adapters 1820 or 1830 relative to the post 1472 achieves the dual offset between the handle and the insertion member detailed above. Thus, depending on which leg is being operated, a surgeon may connect either adapter 1820 or 1830 to the conventional single offset handle, as illustrated in FIGS. 58B-58C and 59B. Use of either adapter 1820 or 1830 offsets the axis of the handle 1244 both anteriorly and laterally from the axis of the insertion member 1442. As described in detail above, this anterior and lateral offset provides a clearance of the handle with respect to the patient's gut zone and other musculature.

In use, the desired embodiment of the instrument is selected and either the left or right femur of the patient is selected for installation of a prosthetic stem component. The instrument is configured to operate on the selected femur by causing the handle to be offset from the surgical member in the direction that includes an X directional component and also a Y directional component to provide the desired lateral and anterior offset of the handle relative to the shaping member. The shaping member portion of the instrument, or the instrument, is then inserted into the medullary canal of the selected femur through a surgical incision using an anterior approach. The medullary canal is then operated on using the instrument. The instrument is then removed and a prosthetic stem component is installed in the medullary canal and the surgery completed.

While the instruments described herein have been described for use with femoral intramedullary canal preparation, they may be advantageously utilized with any surgical procedure. For example, the instruments according to various embodiments of the invention may be utilized to prepare a humerus during shoulder surgery, prepare a femoral head for femoral head resurfacing, or to prepare an acetabulum (e.g., offsetting an acetabular shaping member in a negative X direction and a negative Y direction for acceptance of an acetabular implant). In such latter cases, as for use in acetabular preparation with a direct anterior approach, a distal end of the instrument can generally be configured to extend in the Z direction (towards the head of the patient), and an opposite configuration can be used. For instance, the instrument configuration shown in FIG. 6 for use on a left femur may correspond to the configuration used for a right acetabulum when accessing the acetabulum from a distal perspective relative to a patient. Conversely, the instrument configuration shown in FIG. 7 for use on a right femur could correspond to the configuration used for a left acetabulum when accessing the acetabulum from a distal perspective relative to a patient. In yet other examples, the shaping member may be provided as a reamer, in which cases the instrument body may contain a universal joint, coupling, or other mechanism which can be attached to a drill member for transferring a torque to said reamer. In yet even other examples, the shaping member may be configured as an insertion member adapted to at least temporarily mate with a prosthetic implant such as a femoral stem or acetabular cup and guide and place it within a surgical site.

In use, the desired embodiment of the instrument is selected and either the left or right hip of the patient is selected for installation of a prosthetic stem component. The instrument is configured to operate on femur of the selected leg by causing the handle to be offset from the shaping member in the direction that includes a lateral and an anterior directional component to provide the desired lateral and anterior offset of the handle relative to the shaping member. The shaping member portion of the instrument is then inserted into the intramedullary canal of the selected leg through a surgical incision using an anterior approach. The intramedullary canal is operated on using the instrument. The instrument is then removed and a prosthetic stem component is installed in the intramedullary canal, an acetabular cup can be installed in the acetabulum of the patient, and the surgery completed.

The embodiments disclosed above were chosen and described in order best to explain the principles of the invention and its practical application thereby to enable others skilled in the art best to make and utilize the invention and various embodiments and with various modifications as are suited to the particular manufacture or use contemplated. As various modifications could be made in the constructions and methods herein described and illustrated without departing from the scope of the invention, it is intended that all matter contained in the foregoing description or appended claims, or shown in the accompanying drawings shall be interpreted as illustrative rather than limiting. Thus, breadth and scope of the present invention should not be limited by any of the above-described embodiments, but should be defined only in accordance with the following claims appended hereto and their equivalents.

What is claimed is:

1. A device for preparing a medullary canal of a femur for installation of a stem of a femoral component of a prosthetic hip along a long axis of the femur, comprising:
   a handle having a longitudinal axis and an anterior facing surface;
   a shaping member having a longitudinal axis and an anterior facing surface; and
   a coupling member joining the handle and the shaping member such that the handle and shaping member longitudinal axes are offset and parallel, wherein the handle is double-offset relative to the shaping member such that in use the anterior facing surface of the handle is offset in the lateral direction relative to the anterior facing surface of the shaping member while the shaping member is axially aligned with the long axis of the femur, wherein the handle, shaping member and coupling member are configured such that by manipulating the handle, the shaping member can be positioned into the medullary canal through an incision by a non-vertical approach to the femur, the device being configurable between a first configuration for use on a left femur when the shaping member is coupled to the coupling member at a first location and a second configuration for use on a right femur when the shaping member is coupled to the coupling member at a second location.

2. The device of claim 1 wherein the handle is offset laterally and anteriorly from the shaping member when configured for use on a left femur and when configured for use on a right femur.

3. A kit of hip arthroplasty components, comprising:
   a stem of a femoral component of a prosthetic hip;
   a device for preparing a medullary canal of a femur for installation of the stem along a long axis of the femur, comprising:
      a handle having a longitudinal axis and an anterior facing surface;
      a shaping member having a longitudinal axis and an anterior facing surface; and
      a coupling member joining the handle and the shaping member such that the handle and shaping member longitudinal axes are offset and parallel, wherein the handle is double-offset relative to the shaping member such that in use the anterior facing surface of the handle is offset in the medial-lateral direction relative to the anterior facing surface of the shaping member while the shaping member is axially aligned with the long axis of the femur, and wherein the handle, shaping member and coupling member are configured such that by manipulating the handle, the shaping member can be positioned into the medullary canal through an incision by a non-vertical approach to the femur, the device being configurable for use on both a left femur and a right femur.

4. The kit of claim 3 wherein the handle is offset laterally and anteriorly from the shaping member when configured for use on a left femur and when configured for use on a right femur.

5. An instrument for shaping a medullary canal of both a patient's left leg and right leg, comprising:
   (a) a handle that includes a handle longitudinal axis;
   (b) a shaping member including:
      structure configured to shape bone;
      a shaping member longitudinal axis, and
      a connecting structure that includes an interpositional cooperation structure;
   (c) an offset member that physically connects the handle to the shaping member, the offset member extending in an offset direction that includes a first directional component in a first direction orthogonal to the longitudinal axis of the shaping member, and a second directional component in the direction of the shaping member longitudinal axis;
   (d) the offset member including:
      (i) a first opening adapted to receive the shaping member connecting structure, the first opening configured to receive the shaping member connecting structure in a manner whereby the shaping member longitudinal axis is substantially parallel to the handle longitudinal axis;
      (ii) a second opening adapted to receive the shaping member connecting structure, the second opening configured to receive the shaping member connecting structure in a manner whereby the shaping member longitudinal axis is substantially parallel to the handle longitudinal axis; and
   (e) a retention device or member comprising an actuator and at last one interpositional structure, the retention device or member configured to interpose the at least one interpositional structure relative to the interpositional cooperation structure of the shaping member connecting structure when the actuator is actuated.

6. The instrument of claim 1, wherein the shaping member comprises a reference plane and the first and second openings are configured to receive the shaping member connecting structure in a manner such that the first direction orthogonal to the longitudinal axis of the shaping member bisects the angle formed by the shaping member reference plane when the shaping member is connected to the first opening and the shaping member reference plane when the shaping member is connected to the second opening.

7. The instrument of claim 1, wherein the shaping member comprises a reference plane and the first and second openings are configured to receive the shaping member connecting structure in a manner such that when the shaping member is connected to the first opening, the shaping member reference plane is substantially orthogonal to the shaping member reference plane when the shaping member is connected to the second opening.

8. The instrument of claim 1, wherein the shaping member is a broach.

9. The instrument of claim 1, wherein the shaping member is a femoral shaping member for preparation of a central femoral cavity for receiving a stem of a femoral component of a prosthetic hip.

10. The instrument of claim 1, further comprising a strike plate with a first beveled surface that corresponds to the first opening on the offset member and a second beveled surface that corresponds to the second opening on the offset member.

11. The instrument of claim 1, wherein the offset member extends in at least two offset directions.

12. The instrument of claim 1, wherein the offset direction includes a third directional component that is orthogonal to the first directional component, the second directional component, and the longitudinal axis of the shaping member.

13. The instrument of claim 1, wherein the offset member includes a first abutment surface and a second abutment surface, the first abutment surface corresponding to the first opening and configured to abut a proximal surface of the shaping member, the second abutment surface corresponding to the second opening and configured to abut a proximal surface of the shaping member.

14. The instrument of claim 1, wherein the actuator of the retention device or member includes an over-center linkage configured to lock the interpositional structure in place when interposed with the interpositional cooperation structure of the shaping member connecting structure, and wherein the interpositional structure comprises at least one pawl.

15. The instrument of claim 1, wherein the actuator of the retention device or member includes a wedge, the interpositional structure includes at least one claw, and the wedge is configured to urge the at least one claw into interposed position with the interpositional cooperation structure of the shaping member connecting structure.

16. An instrument for operating on a medullary canal for installation of a prosthetic stem component in a patient, comprising:
a handle including an elongated shaft extending approximately in a negative z-direction;
a first offset capable of extending in a first direction that includes an x-directional component or a negative x-directional component;
a second offset extending in a second direction that includes a negative y-directional component;
the handle connected to either the first or second offset;
an insertion member extending from either the first offset or the second offset in an insertion member direction that includes a negative z-directional component;
wherein the negative y-directional component and negative z-directional components are orthogonal to each other and orthogonal to the x-directional component and the negative x-directional component, and
wherein the handle and the insertion member are positioned with respect to one another in a non-planar relationship.

17. The instrument of claim 16, wherein one of the offsets is connected to the handle via a pivot capable of rotating relative to the handle such that one of the offsets extends in approximately an x-direction or a negative x-direction in order to configure the instrument for use with a right leg or a left leg of the patient.

18. The instrument of claim 16, wherein the handle is configured to connect to the second offset on either a first side of the handle that faces the x direction or a second side of the handle that faces the negative x direction in order to form the first offset.

19. The instrument of claim 16, wherein the insertion member further comprises cutting elements.

20. An instrument for operating on a medullary canal for installation of a prosthetic stem component in a patient, comprising:
a handle including an elongated shaft extending in an approximately negative z-direction;
an offset connected to the handle, the offset extending in a first direction that includes a negative y-directional component and capable of extending in a second direction that includes an x-directional component or a negative x-directional component;
a shaping member extending from the offset in a shaping member direction that includes a negative z-directional component,
wherein the negative y-directional component and negative z-directional components are orthogonal to each other and orthogonal to the x-directional component and the negative x-directional component,
wherein the handle and the shaping member are positioned with respect to one another in a non-coplanar relationship, and
wherein the shaping member further comprises cutting elements.

21. The instrument of claim 20, wherein the offset is connected to the handle via a pivot, and the handle and pivot are capable of rotating relative to each other such that the offset extends in a direction that includes an x-directional component or a negative x-directional component in order to configure the instrument for use with a right leg or a left leg of the patient.

22. A method of installing a prosthetic stem component into the medullary canal of a right leg or a left leg of a patient, comprising the steps of:
obtaining an instrument capable of shaping a medullary canal of both a patient's left leg and right leg, comprising:
(a) a handle that includes a handle longitudinal axis;
(b) a shaping member including:
structure configured to shape bone;
a shaping member longitudinal axis, and
a connecting structure that includes an interpositional cooperation structure;
(c) an offset member that physically connects the handle to the shaping member, the offset member extending in an offset direction that includes a first directional component in a first direction orthogonal to the longitudinal axis of the shaping member, and a second directional component in the direction of the shaping member longitudinal axis;
(d) the offset member including:
(i) a first opening adapted to receive the shaping member connecting structure, the first opening configured to receive the shaping member connecting structure in a manner whereby the shaping member longitudinal axis is substantially parallel to the handle longitudinal axis;
(ii) a second opening adapted to receive the shaping member connecting structure, the second opening configured to receive the shaping member connecting structure in a manner whereby the shaping member longitudinal axis is substantially parallel to the handle longitudinal axis; and (e) a retention device or member comprising an actuator and at last one interpositional structure, the retention device or member configured to interpose the at least one interpositional structure relative to the interpositional cooperation structure of the shaping member connecting structure when the actuator is actuated;

selecting either the left leg or the right leg of the patient as the leg for installation of the prosthetic stem component;

configuring the instrument to operate on the selected leg by connecting the shaping member to the first opening or the second opening;

inserting the instrument into the medullary canal of the selected leg through a surgical incision;

operating on the medullary canal of the selected leg with the instrument;

removing the instrument from the medullary canal of the selected leg;

installing the prosthetic stem component in the medullary canal of the selected leg; and completing the surgery.

23. The method of claim 22, wherein:

the step of obtaining an instrument capable of shaping a medullary canal of both a patient's left leg or a right leg includes obtaining an instrument that includes a strike plate connected to the handle, the strike plate including a first beveled surface that corresponds to the first opening on the offset member and a second beveled surface that corresponds to the second opening on the offset member; and the step of operating on the medullary canal of the selected leg with the instrument includes striking the instrument on a predetermined one of the first beveled surface and the second beveled surface.

24. A method of installing a prosthetic stem component into the medullary canal of a right leg or a left leg of a patient, comprising the steps of:

obtaining an instrument capable of operating on the medullary canal of the right leg or the left leg of the patient for installation of a prosthetic stem component, comprising a handle including a shaft extending downward approximately in a negative z-direction, a first offset configured to extend from a bottom of the elongated shaft in a first direction that includes an x-directional component or a negative x-directional component, a second offset extending from the first offset in a second direction that includes a negative y-directional component, and a shaping member including structure configured to shape bone, the shaping member extending downward from the second offset in a shaping member direction that includes a negative z-directional component, wherein the negative y-directional component and the negative z-directional component are orthogonal to each other, and the negative y-directional component and the negative z-directional component are orthogonal to the x-directional component and the negative x-directional component, and wherein the handle and the shaping member are positioned with respect to one another in a non-planar relationship;

selecting either the left leg or the right leg of the patient as the leg for installation of the prosthetic stem component;

configuring the instrument to operate on the selected leg by causing the first offset to extend from the handle in either the direction that includes the x-directional component or the direction that includes the negative-x directional component;

inserting the instrument into the medullary canal of the selected leg through a surgical incision;

operating on the medullary canal of the selected leg with the instrument;

removing the instrument from the medullary canal of the selected leg;

installing the prosthetic stem component in the medullary canal of the selected leg; and completing the surgery.

25. The method of claim 24, wherein:

the step of obtaining an instrument capable of operating on the medullary canal of the right leg or the left leg of the patient includes obtaining an instrument that includes a strike plate connected to the handle, the strike plate including a first beveled surface that corresponds to the first opening on the offset member and a second beveled surface that corresponds to the second opening on the offset member; and the step of operating on the medullary canal of the selected leg with the instrument includes striking the instrument on a predetermined one of the first beveled surface and the second beveled surface.

26. The method of claim 24, wherein the step of inserting the instrument into the medullary canal of the selected leg comprises inserting the instrument into an anterior surgical incision.

27. The method of claim 24, wherein the step of inserting the instrument into the medullary canal of the selected leg comprises inserting the instrument into a minimally invasive surgical incision.

28. The method of claim 24, wherein the step of inserting the instrument into the medullary canal of the selected leg comprises inserting the instrument into a surgical incision that is from approximately 4 cm to approximately 16 cm in length.

29. The method of claim 24, wherein the step of inserting the instrument into the medullary canal of the selected leg comprises inserting a femoral shaping member.

30. The method of claim 24, wherein the step of inserting the instrument into the medullary canal of the selected leg comprises inserting a broach.

31. A method of installing a prosthetic stem component into the medullary canal of a right leg or a left leg of a patient, comprising the steps of:

obtaining an instrument capable of operating on the medullary canal of the right leg or the left leg of the patient for installation of a prosthetic stem component, the instrument comprising:

a handle including an elongated shaft extending approximately in a negative z-direction;

an offset connected to the handle, the offset extending in a first direction that includes a negative y-directional component and capable of extending in a second direction that includes an x-directional component or a negative x-directional component;

a shaping member extending downward the offset in a shaping member direction that includes a negative z-directional component, wherein the negative y-directional component and negative z-directional components are orthogonal to each other and orthogonal to the x-directional component and the negative x-directional component, wherein the handle and the shaping member are positioned with respect to one another in a non-planar relationship, and
wherein the shaping member further comprises cutting elements;
selecting either the left leg or the right leg of the patient as the leg for installation of the prosthetic stem component;
configuring the instrument to operate on the selected leg by causing the first offset to extend from the handle in either the direction that includes the x-directional component or the direction that includes the negative-x directional component;
inserting the instrument into the medullary canal of the selected leg through a surgical incision;
operating on the medullary canal of the selected leg with the instrument;
removing the instrument from the medullary canal of the selected leg;
installing the prosthetic stem component in the medullary canal of the selected leg; and
completing the surgery.

32. The method of claim 31, wherein:
the step of obtaining an instrument capable of operating on the medullary canal of the right leg or the left leg of the patient includes obtaining an instrument that includes a strike plate connected to the handle, the strike plate including a first beveled surface that corresponds to the first opening on the offset member and a second beveled surface that corresponds to the second opening on the offset member; and
the step of operating on the medullary canal of the selected leg with the instrument includes striking the instrument on a predetermined one of the first beveled surface and the second beveled surface.

33. The method of claim 32, wherein the step of inserting the instrument into the medullary canal of the selected leg comprises inserting a femoral shaping member.

34. The method of claim 32, wherein the step of inserting the instrument into the medullary canal of the selected leg comprises inserting a broach.

* * * * *